US010415062B2

(12) United States Patent
Soucaille et al.

(10) Patent No.: US 10,415,062 B2
(45) Date of Patent: Sep. 17, 2019

(54) MODIFIED MICROORGANISM FOR THE OPTIMIZED PRODUCTION OF 2,4-DIHYDROXYBUTYRATE

(71) Applicant: METABOLIC EXPLORER, Saint Beauzire (FR)

(72) Inventors: Philippe Soucaille, Deyme (FR); Gwénaëlle Bestel-Corre, Saint Beauzire (FR); Laurence Dumon-Seignovert, Pont du Chateau (FR)

(73) Assignee: METABOLIC EXPLORER, Saint Beauzire (FR)

( * ) Notice: Subject to any disclaimer, the term of this patent is extended or adjusted under 35 U.S.C. 154(b) by 128 days.

(21) Appl. No.: 15/564,919

(22) PCT Filed: Apr. 7, 2015

(86) PCT No.: PCT/IB2015/000618
§ 371 (c)(1),
(2) Date: Oct. 6, 2017

(87) PCT Pub. No.: WO2016/162712
PCT Pub. Date: Oct. 13, 2016

(65) Prior Publication Data
US 2018/0100169 A1 Apr. 12, 2018

(51) Int. Cl.
| | | |
|---|---|---|
| *C12P 7/42* | (2006.01) |
| *C07C 31/22* | (2006.01) |
| *C07C 47/19* | (2006.01) |
| *C07C 59/10* | (2006.01) |
| *C12N 9/04* | (2006.01) |
| *C12P 7/18* | (2006.01) |
| *C12N 9/02* | (2006.01) |
| *C12N 15/00* | (2006.01) |
| *C12N 1/00* | (2006.01) |
| *C12N 15/63* | (2006.01) |
| *C12R 1/19* | (2006.01) |
| *C12R 1/07* | (2006.01) |
| *C12R 1/145* | (2006.01) |

(52) U.S. Cl.
CPC .............. *C12P 7/42* (2013.01); *C07C 31/22* (2013.01); *C07C 47/19* (2013.01); *C07C 59/10* (2013.01); *C12N 9/0004* (2013.01); *C12N 9/0006* (2013.01); *C12P 7/18* (2013.01); *C12R 1/19* (2013.01); *C12Y 101/01001* (2013.01); *C12Y 102/01003* (2013.01); *C12Y 102/01004* (2013.01); *C12Y 102/03001* (2013.01); *C12R 1/07* (2013.01); *C12R 1/145* (2013.01)

(58) Field of Classification Search
None
See application file for complete search history.

(56) References Cited

U.S. PATENT DOCUMENTS

2009/0318715 A1  12/2009  Deck et al.
2013/0204016 A1  8/2013  Henryon et al.

FOREIGN PATENT DOCUMENTS

| AU | 2004200948 A1 | 4/2004 |
| DE | 19735575 A1 | 2/1999 |
| EP | 1167534 A2 | 1/2002 |
| KR | 10-2012-0041827 A | 5/2012 |
| WO | WO 2008/022953 A1 | 2/2008 |
| WO | WO 2008/091288 A2 | 7/2008 |
| WO | WO 2012/056318 A1 | 5/2012 |
| WO | WO 2013/160762 A2 | 10/2013 |
| WO | WO 2014/009435 A1 | 1/2014 |
| WO | WO 2014/074895 A2 | 5/2014 |
| WO | WO 2015/065485 A1 | 5/2015 |

OTHER PUBLICATIONS

Altschul et al., "Basic Local Alignment Search Tool," J. Mol. Biol., vol. 215, No. 3, 1990, pp. 403-410.
Anderson, "Growth Requirements of Virus-Resistant Mutants of *Escherichia coli* Strain "B"," Proc. N. A. S., vol. 32, 1946, pp. 120-128.
Bocanegra et al., "Creation of an NADP-Dependent Pyruvate Dehydrogenase Multienzyme Complex by Protein Engineering," Biochemistry, vol. 32, No. 11, Mar. 23, 1993, pp. 2737-2740.
Carrier et al., "Library of Synthetic 5' Secondary Structures to Manipulate mRNA Stability in *Escherichia coli*," Biotechnol. Prog., vol. 15, No. 1, 1999 (published on web Jan. 9, 1999), pp. 58-64.
Centeno-Leija et al., "Metabolic and Transcriptional Response of *Escherichia coli* with a $NADP^+$-dependent Glyceraldehyde 3-phosphate dehydrogenase from *Streptococcus* mutans," Antonie van Leeuwenhoek, vol. 104, No. 6, 2013 (published online Aug. 29, 2013), pp. 913-924.
Datsenko et al., "One-Step Inactivation of Chromosomal Genes in *Escherichia coli* K-12 Using PCR Products," Proc. N. A. S., vol. 97, No. 12, Jun. 6, 2000, pp. 6640-6645.
Davis et al., "Characterizing the Native Codon Usages of a Genome: An Axis Projection Approach," Mol. Biol. Evol., vol. 28, No. 1, 2011 (Advanced Access Publication Aug. 2, 2010), pp. 211-221.
Deml et al., "Multiple Effects of Codon Usage Optimization on Expression and Immunogenicity of DNA Candidate Vaccines Encoding the Human Immunodeficiency Virus Type 1 Gag Protein," Journal of Virology, vol. 75, No. 22, Nov. 2001, pp. 10991-11001.
European Application No. 14306564.7, filed Oct. 3, 2014, by Metabolic Explorer, 51 pages.

(Continued)

*Primary Examiner* — Suzanne M Noakes
*Assistant Examiner* — Jae W Lee
(74) *Attorney, Agent, or Firm* — Birch, Stewart, Kolasch & Birch, LLP

(57) ABSTRACT

The present invention relates to a genetically modified microorganism for the production of 2,4-dihydroxybutyrate, by metabolic transformation of xylose via the 1,2,4-butanetriol intermediate. The invention also relates to a method for the production of 2,4-dihydroxybutyrate by culturing said genetically modified microorganism in a fermentation medium and recovering 2,4-DHB from said medium.

10 Claims, 1 Drawing Sheet

Specification includes a Sequence Listing.

(56) References Cited

OTHER PUBLICATIONS

Graf et al., "Concerted Action of Multiple cis-Acting Sequences is Required for Rev Dependence of Late Human Immunodeficiency Virus Type 1 Gene Expression," Journal of Virology, vol. 74, No. 22, Nov. 2000, pp. 10822-10826.

Hogema et al., "Catabolite Repression by Glucose 6-phosphate, Gluconate and Lactose in *Escherichia coli*," Molecular Microbiology, vol. 24, No. 4, 1997, pp. 857-867.

International Preliminary Report on Patentability and Written Opinion of the International Searching Authority (Forms PCT/IB/373 and PCT/ISA/237) for International Application No. PCT/IB2015/000618, dated Oct. 10, 2017.

International Search Report (Form PCT/ISA/210) for International Application No. PCT/IB2015/000618, dated Oct. 30, 2015.

Kim et al., "Simultaneous Consumption of Pentose and Hexose Sugars: An Optimal Microbial Phenotype for Efficient Fermentation of Lignocellulosic Biomass," Appl Microbiol Biotechnol, vol. 88, 2010 (published online Sep. 14, 2010), pp. 1077-1085.

Kovach et al., "Four New Derivatives of the Broad-Host-Range Cloning Vector pBBR1MCS, Carrying Different Antibiotic-Resistance Cassettes," Gene, vol. 166, No. 1, 1995, pp. 175-176.

Lee et al., "Control of Substrate Access to the Active Site in Methane Monooxygenase," Nature, vol. 494, No. 7437, Feb. 21, 2013, pp. 380-384 (12 pages total).

Lerner et al., "Low Copy Number Plasmids for Regulated Low-Level Expression of Cloned Genes in *Escherichia coli* with Blue/White Insert Screening Capability," Nucleic Acids Research, vol. 18, No. 15, 1990, p. 4631.

Lim et al., "Amplification of the NADPH-Related Genes zwf and gnd for the Oddball Biosynthesis of PHB in an *E. coli* Transformant Harboring a Cloned phbCAB Operon," Journal of Bioscience and Bioengineering, vol. 93, No. 6, 2002 pp. 543-549.

Marbaix et al., "Extremely Conserved ATP- or ADP-dependent Enzymatic System for Nicotinamide Nucleotide Repair," The Journal of Biological Chemistry, vol. 286, No. 48, Dec. 2, 2011 (published on web Oct. 12, 2011), pp. 41246-41252 (8 pages total).

Salis, "The Ribosome Binding Site Calculator," Methods in Enzymology, vol. 498, 2011, pp. 19-42.

Sambrook et al., "Molecular Cloning: A Laboratory Manual," Cold Spring Harbor Laboratory Press, 4th Edition, vol. 1, 2012, 34 pages (Table of Contents, List of Tables and Preface provided).

Schmid et al., "Plasmid-Mediated Uptake and Metabolism of Sucrose by *Escherichia coli* K-12," Journal of Bacteriology, vol. 151, No. 1, Jul. 1982, pp. 68-76.

Segel, "Enzyme Kinetics," John Wiley & Sons, 1993, pp. 44-54 and 100-112 (13 pages total).

Valdehuesa et al., "Direct Bioconversion of D -xylose to 1,2,4-butanetriol in an engineered *Escherichia coli*," Process Biochemistry, vol. 49, No. 1, 2014 (published on web Oct. 12, 2013), pp. 25-32.

Extract from Uniprot, ID No. A0A1D3KE64_ECOLX, Nov. 30, 2016 https://www.uniprot.org/uniprot/AoA1D3KE64.txt.

Jacqueline E. Gonzalez, "Comprehensive analysis of glucose and xylose metabolism in *Escherichia coli* under aerobic and anaerobic conditions by 13C metabolic flux analysis" Metabolic Engineering, 39 (2017), pp. 9-18.

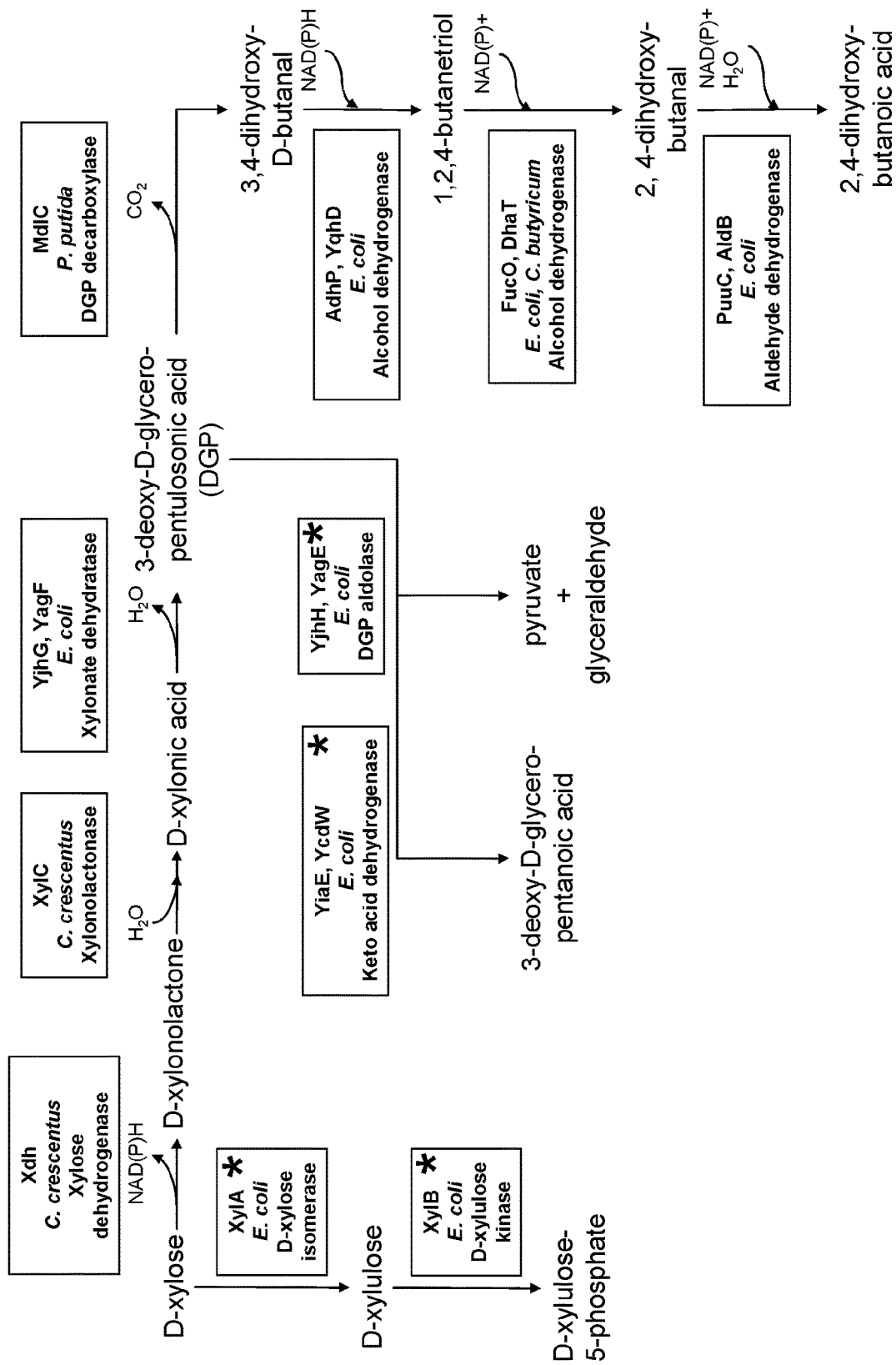

SEQUENCE LISTING

<160> NUMBER OF SEQ ID NOS: 128

<210> SEQ ID NO 1
<211> LENGTH: 369
<212> TYPE: PRT
<213> ORGANISM: Escherichia coli

<400> SEQUENCE: 1

```
Met Lys Ser Arg Ala Ala Val Ala Phe Ala Pro Gly Lys Pro Leu Glu
1               5                   10                  15

Ile Val Glu Ile Asp Val Ala Pro Pro Lys Lys Gly Glu Val Leu Ile
            20                  25                  30

Lys Val Thr His Thr Gly Val Cys His Thr Asp Ala Phe Thr Leu Ser
        35                  40                  45

Gly Asp Asp Pro Glu Gly Val Phe Pro Val Val Leu Gly His Glu Gly
    50                  55                  60

Ala Gly Val Val Glu Val Gly Gly Val Thr Ser Val Lys Pro
65                  70                  75                  80

Gly Asp His Val Ile Pro Leu Tyr Thr Ala Glu Cys Gly Glu Cys Glu
                85                  90                  95

Phe Cys Arg Ser Gly Lys Thr Asn Leu Cys Val Ala Val Arg Glu Thr
            100                 105                 110

Gln Gly Lys Gly Leu Met Pro Asp Gly Thr Thr Arg Phe Ser Tyr Asn
        115                 120                 125

Gly Gln Pro Leu Tyr His Tyr Met Gly Cys Ser Thr Phe Ser Glu Tyr
    130                 135                 140

Thr Val Val Ala Glu Val Ser Leu Ala Lys Ile Asn Pro Glu Ala Asn
145                 150                 155                 160

His Glu His Val Cys Leu Leu Gly Cys Gly Val Thr Thr Gly Ile Gly
                165                 170                 175

Ala Val His Asn Thr Ala Lys Val Gln Pro Gly Asp Ser Val Ala Val
            180                 185                 190

Phe Gly Leu Gly Ala Ile Gly Leu Ala Val Val Gln Gly Ala Arg Gln
        195                 200                 205

Ala Lys Ala Gly Arg Ile Ile Ala Ile Asp Thr Asn Pro Lys Lys Phe
    210                 215                 220

Asp Leu Ala Arg Arg Phe Gly Ala Thr Asp Cys Ile Asn Pro Asn Asp
225                 230                 235                 240

Tyr Asp Lys Pro Ile Lys Asp Val Leu Leu Asp Ile Asn Lys Trp Gly
                245                 250                 255
```

-continued

```
Ile Asp His Thr Phe Glu Cys Ile Gly Asn Val Asn Val Met Arg Ala
        260                 265                 270

Ala Leu Glu Ser Ala His Arg Gly Trp Gly Gln Ser Val Ile Ile Gly
        275                 280                 285

Val Ala Val Ala Gly Gln Glu Ile Ser Thr Arg Pro Phe Gln Leu Val
        290                 295                 300

Thr Gly Arg Val Trp Lys Gly Ser Ala Phe Gly Val Lys Gly Arg
305                 310                 315                 320

Ser Gln Leu Pro Gly Met Val Glu Asp Ala Met Lys Gly Asp Ile Asp
                    325                 330                 335

Leu Glu Pro Phe Val Thr His Thr Met Ser Leu Asp Glu Ile Asn Asp
        340                 345                 350

Ala Phe Asp Leu Met His Glu Gly Lys Ser Ile Arg Thr Val Ile Arg
        355                 360                 365

Tyr

<210> SEQ ID NO 2
<211> LENGTH: 336
<212> TYPE: PRT
<213> ORGANISM: Escherichia coli

<400> SEQUENCE: 2

Met Lys Ala Ala Val Val Thr Lys Asp His His Val Asp Val Thr Tyr
1               5                   10                  15

Lys Thr Leu Arg Ser Leu Lys His Gly Glu Ala Leu Leu Lys Met Glu
                20                  25                  30

Cys Cys Gly Val Cys His Thr Asp Leu His Val Lys Asn Gly Asp Phe
            35                  40                  45

Gly Asp Lys Thr Gly Val Ile Leu Gly His Glu Gly Ile Gly Val Val
        50                  55                  60

Ala Glu Val Gly Pro Gly Val Thr Ser Leu Lys Pro Gly Asp Arg Ala
65                  70                  75                  80

Ser Val Ala Trp Phe Tyr Glu Gly Cys Gly His Cys Glu Tyr Cys Asn
                    85                  90                  95

Ser Gly Asn Glu Thr Leu Cys Arg Ser Val Lys Asn Ala Gly Tyr Ser
                100                 105                 110

Val Asp Gly Gly Met Ala Glu Glu Cys Ile Val Val Ala Asp Tyr Ala
            115                 120                 125

Val Lys Val Pro Asp Gly Leu Asp Ser Ala Ala Ala Ser Ser Ile Thr
        130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                    165                 170                 175

Ala Leu Gln Tyr Ala Lys Asn Val Phe Asn Ala Lys Val Ile Ala Ile
                180                 185                 190

Asp Val Asn Asp Glu Gln Leu Lys Leu Ala Thr Glu Met Gly Ala Asp
            195                 200                 205

Leu Ala Ile Asn Ser His Thr Glu Asp Ala Ala Lys Ile Val Gln Glu
        210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                    245                 250                 255
```

-continued

```
Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335

<210> SEQ ID NO 3
<211> LENGTH: 383
<212> TYPE: PRT
<213> ORGANISM: Escherichia coli

<400> SEQUENCE: 3

Met Ala Ala Ser Thr Phe Phe Ile Pro Ser Val Asn Val Ile Gly Ala
1               5                   10                  15

Asp Ser Leu Thr Asp Ala Met Asn Met Met Ala Asp Tyr Gly Phe Thr
            20                  25                  30

Arg Thr Leu Ile Val Thr Asp Asn Met Leu Thr Lys Leu Gly Met Ala
        35                  40                  45

Gly Asp Val Gln Lys Ala Leu Glu Glu Arg Asn Ile Phe Ser Val Ile
    50                  55                  60

Tyr Asp Gly Thr Gln Pro Asn Pro Thr Thr Glu Asn Val Ala Ala Gly
65                  70                  75                  80

Leu Lys Leu Leu Lys Glu Asn Asn Cys Asp Ser Val Ile Ser Leu Gly
                85                  90                  95

Gly Gly Ser Pro His Asp Cys Ala Lys Gly Ile Ala Leu Val Ala Ala
            100                 105                 110

Asn Gly Gly Asp Ile Arg Asp Tyr Glu Gly Val Asp Arg Ser Ala Lys
        115                 120                 125

Pro Gln Leu Pro Met Ile Ala Ile Asn Thr Thr Ala Gly Thr Ala Ser
    130                 135                 140

Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
            180                 185                 190

Met Asp Ala Leu Thr His Ala Ile Glu Ala Tyr Val Ser Ile Ala Ala
        195                 200                 205

Thr Pro Ile Thr Asp Ala Cys Ala Leu Lys Ala Val Thr Met Ile Ala
    210                 215                 220

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Phe
            260                 265                 270

Tyr Asn Leu Pro His Gly Val Cys Asn Ala Val Leu Leu Pro His Val
        275                 280                 285

Gln Val Phe Asn Ser Lys Val Ala Ala Ala Arg Leu Arg Asp Cys Ala
    290                 295                 300
```

```
Ala Ala Met Gly Val Asn Val Thr Gly Lys Asn Asp Ala Glu Gly Ala
305                 310                 315                 320

Glu Ala Cys Ile Asn Ala Ile Arg Glu Leu Ala Lys Lys Val Asp Ile
            325                 330                 335

Pro Ala Gly Leu Arg Asp Leu Asn Val Lys Glu Glu Asp Phe Ala Val
        340                 345                 350

Leu Ala Thr Asn Ala Leu Lys Asp Ala Cys Gly Phe Thr Asn Pro Ile
    355                 360                 365

Gln Ala Thr His Glu Glu Ile Val Ala Ile Tyr Arg Ala Ala Met
370                 375                 380

<210> SEQ ID NO 4
<211> LENGTH: 395
<212> TYPE: PRT
<213> ORGANISM: Escherichia coli

<400> SEQUENCE: 4

Met Gln Asn Glu Leu Gln Thr Ala Leu Phe Gln Ala Phe Asp Thr Leu
1               5                   10                  15

Asn Leu Gln Arg Val Lys Thr Phe Ser Val Pro Pro Val Thr Leu Cys
            20                  25                  30

Gly Pro Gly Ser Val Ser Ser Cys Gly Gln Gln Ala Gln Thr Arg Gly
        35                  40                  45

Leu Lys His Leu Phe Val Met Ala Asp Ser Phe His Gln Ala Gly
    50                  55                  60

Met Thr Ala Gly Leu Thr Arg Ser Leu Thr Val Lys Gly Ile Ala Met
65                  70                  75                  80

Thr Leu Trp Pro Cys Pro Val Gly Glu Pro Cys Ile Thr Asp Val Cys
                85                  90                  95

Ala Ala Val Ala Gln Leu Arg Glu Ser Gly Cys Asp Gly Val Ile Ala
            100                 105                 110

Phe Gly Gly Gly Ser Val Leu Asp Ala Ala Lys Ala Val Thr Leu Leu
        115                 120                 125

Val Thr Asn Pro Asp Ser Thr Leu Ala Glu Met Ser Glu Thr Ser Val
    130                 135                 140

Leu Gln Pro Arg Leu Pro Leu Ile Ala Ile Pro Thr Thr Ala Gly Thr
145                 150                 155                 160

Gly Ser Glu Thr Thr Asn Val Thr Val Ile Ile Asp Ala Val Ser Gly
                165                 170                 175

Arg Lys Gln Val Leu Ala His Ala Ser Leu Met Pro Asp Val Ala Ile
            180                 185                 190

Leu Asp Ala Ala Leu Thr Glu Gly Val Pro Ser His Val Thr Ala Met
    195                 200                 205

Thr Gly Ile Asp Ala Leu Thr His Ala Ile Glu Ala Tyr Ser Ala Leu
210                 215                 220

Asn Ala Thr Pro Phe Thr Asp Ser Leu Ala Ile Gly Ala Ile Ala Met
225                 230                 235                 240

Ile Gly Lys Ser Leu Pro Lys Ala Val Gly Tyr Gly His Asp Leu Ala
                245                 250                 255

Ala Arg Glu Ser Met Leu Leu Ala Ser Cys Met Ala Gly Met Ala Phe
            260                 265                 270

Ser Ser Ala Gly Leu Gly Leu Cys His Ala Met Ala His Gln Pro Gly
        275                 280                 285

Ala Ala Leu His Ile Pro His Gly Leu Ala Asn Ala Met Leu Leu Pro
```

|  |  |  | 290 |  |  |  |  | 295 |  |  |  |  | 300 |  |

Thr Val Met Glu Phe Asn Arg Met Val Cys Arg Glu Arg Phe Ser Gln
305                     310                     315                     320

Ile Gly Arg Ala Leu Arg Thr Lys Lys Ser Asp Asp Arg Asp Ala Ile
                    325                     330                     335

Asn Ala Val Ser Glu Leu Ile Ala Glu Val Gly Ile Gly Lys Arg Leu
                340                     345                     350

Gly Asp Val Gly Ala Thr Ser Ala His Tyr Gly Ala Trp Ala Gln Ala
            355                     360                     365

Ala Leu Glu Asp Ile Cys Leu Arg Ser Asn Pro Arg Thr Ala Ser Leu
370                     375                     380

Glu Gln Ile Val Gly Leu Tyr Ala Ala Ala Gln
385                     390                     395

<210> SEQ ID NO 5
<211> LENGTH: 387
<212> TYPE: PRT
<213> ORGANISM: Escherichia coli

<400> SEQUENCE: 5

Met Asn Asn Phe Asn Leu His Thr Pro Thr Arg Ile Leu Phe Gly Lys
1                   5                       10                      15

Gly Ala Ile Ala Gly Leu Arg Glu Gln Ile Pro His Asp Ala Arg Val
                20                      25                      30

Leu Ile Thr Tyr Gly Gly Gly Ser Val Lys Lys Thr Gly Val Leu Asp
            35                      40                      45

Gln Val Leu Asp Ala Leu Lys Gly Met Asp Val Leu Glu Phe Gly Gly
        50                      55                      60

Ile Glu Pro Asn Pro Ala Tyr Glu Thr Leu Met Asn Ala Val Lys Leu
65                      70                      75                      80

Val Arg Glu Gln Lys Val Thr Phe Leu Leu Ala Val Gly Gly Gly Ser
                85                      90                      95

Val Leu Asp Gly Thr Lys Phe Ile Ala Ala Ala Ala Asn Tyr Pro Glu
                100                     105                     110

Asn Ile Asp Pro Trp His Ile Leu Gln Thr Gly Gly Lys Glu Ile Lys
            115                     120                     125

Ser Ala Ile Pro Met Gly Cys Val Leu Thr Leu Pro Ala Thr Gly Ser
130                     135                     140

Glu Ser Asn Ala Gly Ala Val Ile Ser Arg Lys Thr Thr Gly Asp Lys
145                     150                     155                     160

Gln Ala Phe His Ser Ala His Val Gln Pro Val Phe Ala Val Leu Asp
                165                     170                     175

Pro Val Tyr Thr Tyr Thr Leu Pro Pro Arg Gln Val Ala Asn Gly Val
            180                     185                     190

Val Asp Ala Phe Val His Thr Val Glu Gln Tyr Val Thr Lys Pro Val
        195                     200                     205

Asp Ala Lys Ile Gln Asp Arg Phe Ala Glu Gly Ile Leu Leu Thr Leu
210                     215                     220

Ile Glu Asp Gly Pro Lys Ala Leu Lys Glu Pro Glu Asn Tyr Asp Val
225                     230                     235                     240

Arg Ala Asn Val Met Trp Ala Ala Thr Gln Ala Leu Asn Gly Leu Ile
                245                     250                     255

Gly Ala Gly Val Pro Gln Asp Trp Ala Thr His Met Leu Gly His Glu
            260                     265                     270

```
Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
370                 375                 380

Ala Ala Arg
385

<210> SEQ ID NO 6
<211> LENGTH: 284
<212> TYPE: PRT
<213> ORGANISM: Escherichia coli

<400> SEQUENCE: 6

Met Gln Gln Lys Met Ile Gln Phe Ser Gly Asp Val Ser Leu Pro Ala
1               5                   10                  15

Val Gly Gln Gly Thr Trp Tyr Met Gly Glu Asp Ala Ser Gln Arg Lys
            20                  25                  30

Thr Glu Val Ala Ala Leu Arg Ala Gly Ile Glu Leu Gly Leu Thr Leu
        35                  40                  45

Ile Asp Thr Ala Glu Met Tyr Ala Asp Gly Gly Ala Glu Lys Val Val
    50                  55                  60

Gly Glu Ala Leu Thr Gly Leu Arg Glu Lys Val Phe Leu Val Ser Lys
65                  70                  75                  80

Val Tyr Pro Trp Asn Ala Gly Gly Gln Lys Ala Ile Asn Ala Cys Glu
                85                  90                  95

Ala Ser Leu Arg Arg Leu Asn Thr Asp Tyr Leu Asp Leu Tyr Leu Leu
            100                 105                 110

His Trp Ser Gly Ser Phe Ala Phe Glu Glu Thr Val Ala Ala Met Glu
        115                 120                 125

Lys Leu Ile Ala Gln Gly Lys Ile Arg Arg Trp Gly Val Ser Asn Leu
    130                 135                 140

Asp Tyr Ala Asp Met Gln Glu Leu Trp Gln Leu Pro Gly Gly Asn Gln
145                 150                 155                 160

Cys Ala Thr Asn Gln Val Leu Tyr His Leu Gly Ser Arg Gly Ile Glu
                165                 170                 175

Tyr Asp Leu Leu Pro Trp Cys Gln Gln Gln Met Pro Val Met Ala
            180                 185                 190

Tyr Ser Pro Leu Ala Gln Ala Gly Arg Leu Arg Asn Gly Leu Leu Lys
        195                 200                 205

Asn Ala Val Val Asn Glu Ile Ala His Ala His Asn Ile Ser Ala Ala
    210                 215                 220

Gln Val Leu Leu Ala Trp Val Ile Ser His Gln Gly Val Met Ala Ile
225                 230                 235                 240

Pro Lys Ala Ala Thr Ile Ala His Val Gln Gln Asn Ala Ala Val Leu
                245                 250                 255
```

```
Glu Val Glu Leu Ser Ser Ala Glu Leu Ala Met Leu Asp Lys Ala Tyr
            260                 265                 270

Pro Ala Pro Lys Gly Lys Thr Ala Leu Asp Met Val
            275                 280

<210> SEQ ID NO 7
<211> LENGTH: 298
<212> TYPE: PRT
<213> ORGANISM: Escherichia coli

<400> SEQUENCE: 7

Met Val Gln Arg Ile Thr Ile Ala Pro Gln Gly Pro Glu Phe Ser Arg
1               5                   10                  15

Phe Val Met Gly Tyr Trp Arg Leu Met Asp Trp Asn Met Ser Ala Arg
            20                  25                  30

Gln Leu Val Ser Phe Ile Glu Glu His Leu Asp Leu Gly Val Thr Thr
        35                  40                  45

Val Asp His Ala Asp Ile Tyr Gly Gly Tyr Gln Cys Glu Ala Ala Phe
    50                  55                  60

Gly Glu Ala Leu Lys Leu Ala Pro His Leu Arg Glu Arg Met Glu Ile
65                  70                  75                  80

Val Ser Lys Cys Gly Ile Ala Thr Thr Ala Arg Glu Glu Asn Val Ile
                85                  90                  95

Gly His Tyr Ile Thr Asp Arg Asp His Ile Ile Lys Ser Ala Glu Gln
            100                 105                 110

Ser Leu Ile Asn Leu Ala Thr Asp His Leu Asp Leu Leu Leu Ile His
        115                 120                 125

Arg Pro Asp Pro Leu Met Asp Ala Asp Glu Val Ala Asp Ala Phe Lys
    130                 135                 140

His Leu His Gln Ser Gly Lys Val Arg His Phe Gly Val Ser Asn Phe
145                 150                 155                 160

Thr Pro Ala Gln Phe Ala Leu Leu Gln Ser Arg Leu Pro Phe Thr Leu
                165                 170                 175

Ala Thr Asn Gln Val Glu Ile Ser Pro Val His Gln Pro Leu Leu Leu
            180                 185                 190

Asp Gly Thr Leu Asp Gln Leu Gln Gln Leu Arg Val Arg Pro Met Ala
        195                 200                 205

Trp Ser Cys Leu Gly Gly Gly Arg Leu Phe Asn Asp Asp Tyr Phe Gln
    210                 215                 220

Pro Leu Arg Asp Glu Leu Ala Val Val Ala Glu Glu Leu Asn Ala Gly
225                 230                 235                 240

Ser Ile Glu Gln Val Val Tyr Ala Trp Val Leu Arg Leu Pro Ser Gln
                245                 250                 255

Pro Leu Pro Ile Ile Gly Ser Gly Lys Ile Glu Arg Val Arg Ala Ala
            260                 265                 270

Val Glu Ala Glu Thr Leu Lys Met Thr Arg Gln Gln Trp Phe Arg Ile
        275                 280                 285

Arg Lys Ala Ala Leu Gly Tyr Asp Val Pro
    290                 295

<210> SEQ ID NO 8
<211> LENGTH: 122
<212> TYPE: PRT
<213> ORGANISM: Escherichia coli

<400> SEQUENCE: 8
```

```
Met Trp Leu Leu Asp Gln Trp Ala Glu Arg His Ile Ala Glu Ala Gln
1               5                   10                  15

Ala Lys Gly Glu Phe Asp Asn Leu Ala Gly Ser Gly Glu Pro Leu Ile
            20                  25                  30

Leu Asp Asp Ser His Val Pro Pro Glu Leu Arg Ala Gly Tyr Arg
        35                  40                  45

Leu Leu Lys Asn Ala Gly Cys Leu Pro Pro Glu Leu Glu Gln Arg Arg
50                  55                  60

Glu Ala Ile Gln Leu Leu Asp Ile Leu Lys Gly Ile Arg His Asp Asp
65                  70                  75                  80

Pro Gln Tyr Gln Glu Val Ser Arg Arg Leu Ser Leu Leu Glu Leu Lys
                85                  90                  95

Leu Arg Gln Ala Gly Leu Ser Thr Asp Phe Leu Arg Gly Asp Tyr Ala
            100                 105                 110

Asp Lys Leu Leu Asp Lys Ile Asn Asp Asn
        115                 120
```

<210> SEQ ID NO 9
<211> LENGTH: 412
<212> TYPE: PRT
<213> ORGANISM: Escherichia coli

<400> SEQUENCE: 9

```
Met Lys Ala Leu Thr Tyr His Gly Pro His His Val Gln Val Glu Asn
1               5                   10                  15

Val Pro Asp Pro Gly Val Glu Gln Ala Asp Asp Ile Ile Leu Arg Ile
            20                  25                  30

Thr Ala Thr Ala Ile Cys Gly Ser Asp Leu His Leu Tyr Arg Gly Lys
        35                  40                  45

Ile Pro Gln Val Lys His Gly Asp Ile Phe Gly His Glu Phe Met Gly
    50                  55                  60

Glu Val Val Glu Thr Gly Lys Asp Val Lys Asn Leu Gln Lys Gly Asp
65                  70                  75                  80

Arg Val Val Ile Pro Phe Val Ile Ala Cys Gly Asp Cys Phe Phe Cys
                85                  90                  95

Arg Leu Gln Gln Tyr Ala Ala Cys Glu Asn Thr Asn Ala Gly Lys Gly
            100                 105                 110

Ala Ala Leu Asn Lys Lys Gln Ile Pro Ala Pro Ala Ala Leu Phe Gly
        115                 120                 125

Tyr Ser His Leu Tyr Gly Gly Val Pro Gly Gly Gln Ala Glu Tyr Val
    130                 135                 140

Arg Val Pro Lys Gly Asn Val Gly Pro Phe Lys Val Pro Pro Leu Leu
145                 150                 155                 160

Ser Asp Asp Lys Ala Leu Phe Leu Ser Asp Ile Leu Pro Thr Ala Trp
                165                 170                 175

Gln Ala Ala Lys Asn Ala Gln Ile Gln Gln Gly Ser Ser Val Ala Val
            180                 185                 190

Tyr Gly Ala Gly Pro Val Gly Leu Leu Thr Ile Ala Cys Ala Arg Leu
        195                 200                 205

Leu Gly Ala Glu Gln Ile Phe Val Val Asp His Pro Tyr Arg Leu
    210                 215                 220

His Phe Ala Ala Asp Arg Tyr Gly Ala Ile Pro Ile Asn Phe Asp Glu
225                 230                 235                 240

Asp Ser Asp Pro Ala Gln Ser Ile Ile Glu Gln Thr Ala Gly His Arg
```

```
                    245                 250                 255
Gly Val Asp Ala Val Ile Asp Ala Val Gly Phe Glu Ala Lys Gly Ser
                260                 265                 270

Thr Thr Glu Thr Val Leu Thr Asn Leu Lys Leu Glu Gly Ser Ser Gly
            275                 280                 285

Lys Ala Leu Arg Gln Cys Ile Ala Ala Val Arg Arg Gly Gly Ile Val
        290                 295                 300

Ser Val Pro Gly Val Tyr Ala Gly Phe Ile His Gly Phe Leu Phe Gly
305                 310                 315                 320

Asp Ala Phe Asp Lys Gly Leu Ser Phe Lys Met Gly Gln Thr His Val
                325                 330                 335

His Ala Trp Leu Gly Glu Leu Leu Pro Leu Ile Glu Lys Gly Leu Leu
            340                 345                 350

Lys Pro Glu Glu Ile Val Thr His Tyr Met Pro Phe Glu Glu Ala Ala
        355                 360                 365

Arg Gly Tyr Glu Ile Phe Glu Lys Arg Glu Glu Cys Arg Lys Val
    370                 375                 380

Ile Leu Val Pro Gly Ala Gln Ser Ala Glu Ala Ala Gln Lys Ala Val
385                 390                 395                 400

Ser Gly Leu Val Asn Ala Met Pro Gly Gly Thr Ile
                405                 410

<210> SEQ ID NO 10
<211> LENGTH: 362
<212> TYPE: PRT
<213> ORGANISM: Escherichia coli

<400> SEQUENCE: 10

Met Pro His Asn Pro Ile Arg Val Val Gly Pro Ala Asn Tyr Phe
1               5                   10                  15

Ser His Pro Gly Ser Phe Asn His Leu His Asp Phe Phe Thr Asp Glu
                20                  25                  30

Gln Leu Ser Arg Ala Val Trp Ile Tyr Gly Lys Arg Ala Ile Ala Ala
            35                  40                  45

Ala Gln Thr Lys Leu Pro Pro Ala Phe Gly Leu Pro Gly Ala Lys His
        50                  55                  60

Ile Leu Phe Arg Gly His Cys Ser Glu Ser Asp Val Gln Gln Leu Ala
65                  70                  75                  80

Ala Glu Ser Gly Asp Asp Arg Ser Val Val Ile Gly Val Gly Gly Gly
                85                  90                  95

Ala Leu Leu Asp Thr Ala Lys Ala Leu Ala Arg Arg Leu Gly Leu Pro
            100                 105                 110

Phe Val Ala Val Pro Thr Ile Ala Ala Thr Cys Ala Ala Trp Thr Pro
        115                 120                 125

Leu Ser Val Trp Tyr Asn Asp Ala Gly Gln Ala Leu His Tyr Glu Ile
130                 135                 140

Phe Asp Asp Ala Asn Phe Met Val Leu Val Glu Pro Glu Ile Ile Leu
145                 150                 155                 160

Asn Ala Pro Gln Gln Tyr Leu Leu Ala Gly Ile Gly Asp Thr Leu Ala
                165                 170                 175

Lys Trp Tyr Glu Ala Val Val Leu Ala Pro Gln Pro Glu Thr Leu Pro
            180                 185                 190

Leu Thr Val Arg Leu Gly Ile Asn Asn Ala Gln Ala Ile Arg Asp Val
        195                 200                 205
```

```
Leu Leu Asn Ser Ser Glu Gln Ala Leu Ser Asp Gln Gln Asn Gln Gln
    210                 215                 220

Leu Thr Gln Ser Phe Cys Asp Val Val Asp Ala Ile Ile Ala Gly Gly
225                 230                 235                 240

Gly Met Val Gly Gly Leu Gly Asp Arg Phe Thr Arg Val Ala Ala Ala
                245                 250                 255

His Ala Val His Asn Gly Leu Thr Val Leu Pro Gln Thr Glu Lys Phe
                260                 265                 270

Leu His Gly Thr Lys Val Ala Tyr Gly Ile Leu Val Gln Ser Ala Leu
            275                 280                 285

Leu Gly Gln Asp Asp Val Leu Ala Gln Leu Thr Gly Ala Tyr Gln Arg
    290                 295                 300

Phe His Leu Pro Thr Thr Leu Ala Glu Leu Glu Val Asp Ile Asn Asn
305                 310                 315                 320

Gln Ala Glu Ile Asp Lys Val Ile Ala His Thr Leu Arg Pro Val Glu
                325                 330                 335

Ser Ile His Tyr Leu Pro Val Thr Leu Thr Pro Asp Thr Leu Arg Ala
                340                 345                 350

Ala Phe Lys Lys Val Glu Ser Phe Lys Ala
            355                 360

<210> SEQ ID NO 11
<211> LENGTH: 347
<212> TYPE: PRT
<213> ORGANISM: Escherichia coli

<400> SEQUENCE: 11

Met Lys Asn Ser Lys Ala Ile Leu Gln Val Pro Gly Thr Met Lys Ile
1               5                   10                  15

Ile Ser Ala Glu Ile Pro Val Pro Lys Asp Glu Val Leu Ile Lys
            20                  25                  30

Val Glu Tyr Val Gly Ile Cys Gly Ser Asp Val His Gly Phe Glu Ser
        35                  40                  45

Gly Pro Phe Ile Pro Pro Lys Asp Pro Asn Gln Glu Ile Gly Leu Gly
    50                  55                  60

His Glu Cys Ala Gly Thr Val Val Ala Val Gly Ser Arg Val Arg Lys
65                  70                  75                  80

Phe Lys Pro Gly Asp Arg Val Asn Ile Glu Pro Gly Val Pro Cys Gly
                85                  90                  95

His Cys Arg Tyr Cys Leu Glu Gly Lys Tyr Asn Ile Cys Pro Asp Val
            100                 105                 110

Asp Phe Met Ala Thr Gln Pro Asn Tyr Arg Gly Ala Leu Thr His Tyr
        115                 120                 125

Leu Cys His Pro Glu Ser Phe Thr Tyr Lys Leu Pro Asp Asn Met Asp
    130                 135                 140

Thr Met Glu Gly Ala Leu Val Glu Pro Ala Ala Val Gly Met His Ala
145                 150                 155                 160

Ala Met Leu Ala Asp Val Lys Pro Gly Lys Lys Ile Ile Ile Leu Gly
                165                 170                 175

Ala Gly Cys Ile Gly Leu Met Thr Leu Gln Ala Cys Lys Cys Leu Gly
            180                 185                 190

Ala Thr Glu Ile Ala Val Val Asp Val Leu Glu Lys Arg Leu Ala Met
        195                 200                 205

Ala Glu Gln Leu Gly Ala Thr Val Val Ile Asn Gly Ala Lys Glu Asp
    210                 215                 220
```

```
Thr Ile Ala Arg Cys Gln Gln Phe Thr Glu Asp Met Gly Ala Asp Ile
225                 230                 235                 240

Val Phe Glu Thr Ala Gly Ser Ala Val Thr Val Lys Gln Ala Pro Tyr
                245                 250                 255

Leu Val Met Arg Gly Lys Ile Met Ile Val Gly Thr Val Pro Gly
            260                 265                 270

Asp Ser Ala Ile Asn Phe Leu Lys Ile Asn Arg Glu Val Thr Ile Gln
            275                 280                 285

Thr Val Phe Arg Tyr Ala Asn Arg Tyr Pro Val Thr Ile Glu Ala Ile
        290                 295                 300

Ser Ser Gly Arg Phe Asp Val Lys Ser Met Val Thr His Ile Tyr Asp
305                 310                 315                 320

Tyr Arg Asp Val Gln Gln Ala Phe Glu Glu Ser Val Asn Asn Lys Arg
                325                 330                 335

Asp Ile Ile Lys Gly Val Ile Lys Ile Ser Asp
            340                 345
```

<210> SEQ ID NO 12
<211> LENGTH: 358
<212> TYPE: PRT
<213> ORGANISM: Escherichia coli

<400> SEQUENCE: 12

```
Met Lys Ala Leu Ala Arg Phe Gly Lys Ala Phe Gly Gly Tyr Lys Met
1               5                   10                  15

Ile Asp Val Pro Gln Pro Met Cys Gly Pro Glu Asp Val Val Ile Glu
                20                  25                  30

Ile Lys Ala Ala Ala Ile Cys Gly Ala Asp Met Lys His Tyr Asn Val
            35                  40                  45

Asp Ser Gly Ser Asp Glu Phe Asn Ser Ile Arg Gly His Glu Phe Ala
        50                  55                  60

Gly Cys Ile Ala Gln Val Gly Glu Lys Val Lys Asp Trp Lys Val Gly
65                  70                  75                  80

Gln Arg Val Val Ser Asp Asn Ser Gly His Val Cys Gly Val Cys Pro
                85                  90                  95

Ala Cys Glu Gln Gly Asp Phe Leu Cys Cys Thr Glu Lys Val Asn Leu
            100                 105                 110

Gly Leu Asp Asn Asn Thr Trp Gly Gly Phe Ser Lys Tyr Cys Leu
        115                 120                 125

Val Pro Gly Glu Ile Leu Lys Ile His Arg His Ala Leu Trp Glu Ile
130                 135                 140

Pro Asp Gly Val Asp Tyr Glu Asp Ala Ala Val Leu Asp Pro Ile Cys
145                 150                 155                 160

Asn Ala Tyr Lys Ser Ile Ala Gln Gln Ser Lys Phe Leu Pro Gly Gln
                165                 170                 175

Asp Val Val Val Ile Gly Thr Gly Pro Leu Gly Leu Phe Ser Val Gln
            180                 185                 190

Met Ala Arg Ile Met Gly Ala Val Asn Ile Val Val Gly Leu Gln
        195                 200                 205

Glu Asp Val Ala Val Arg Phe Pro Val Ala Lys Glu Leu Gly Ala Thr
210                 215                 220

Ala Val Val Asn Gly Ser Thr Glu Asp Val Val Ala Arg Cys Gln Gln
225                 230                 235                 240

Ile Cys Gly Lys Asp Asn Leu Gly Leu Val Ile Glu Cys Ser Gly Ala
```

```
                            245                 250                 255
Asn Ile Ala Leu Lys Gln Ala Ile Glu Met Leu Arg Pro Asn Gly Glu
            260                 265                 270

Val Val Arg Val Gly Met Gly Phe Lys Pro Leu Asp Phe Ser Ile Asn
        275                 280                 285

Asp Ile Thr Ala Trp Asn Lys Ser Ile Ile Gly His Met Ala Tyr Asp
    290                 295                 300

Ser Thr Ser Trp Arg Asn Ala Ile Arg Leu Leu Ala Ser Gly Ala Ile
305                 310                 315                 320

Lys Val Lys Pro Met Ile Thr His Arg Ile Gly Leu Ser Gln Trp Arg
                325                 330                 335

Glu Gly Phe Asp Ala Met Val Asp Lys Thr Ala Ile Lys Val Ile Met
            340                 345                 350

Thr Tyr Asp Phe Asp Glu
            355

<210> SEQ ID NO 13
<211> LENGTH: 390
<212> TYPE: PRT
<213> ORGANISM: Clostridium acetobutylicum

<400> SEQUENCE: 13

Met Val Asp Phe Glu Tyr Ser Ile Pro Thr Arg Ile Phe Phe Gly Lys
1               5                  10                  15

Asp Lys Ile Asn Val Leu Gly Arg Glu Leu Lys Lys Tyr Gly Ser Lys
            20                  25                  30

Val Leu Ile Val Tyr Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255
```

Thr Tyr Gly Lys Asp Thr Asn Trp Ser Val His Leu Met Glu His Glu
                260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asn Asp Thr Val Tyr Lys
        290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
370                 375                 380

Ile Phe Lys Lys Ser Val
385                 390

<210> SEQ ID NO 14
<211> LENGTH: 389
<212> TYPE: PRT
<213> ORGANISM: Clostridium acetobutylicum

<400> SEQUENCE: 14

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Ser Ile Lys Arg Asn Gly Ile Tyr
            35                  40                  45

Asp Arg Ala Thr Ala Ile Leu Lys Glu Asn Asn Ile Ala Phe Tyr Glu
        50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
            245                 250                 255

Ser Leu Gly Lys Asp Arg Lys Trp Ser Cys His Pro Met Glu His Glu
        260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asp Thr Leu His Lys
        290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
370                 375                 380

Phe Lys Lys Ser Tyr
385

<210> SEQ ID NO 15
<211> LENGTH: 386
<212> TYPE: PRT
<213> ORGANISM: Clostridium acetobutylicum

<400> SEQUENCE: 15

Met Tyr Asn Phe Asp Phe Phe Asn Pro Thr His Ile Val Phe Gly Lys
1               5                   10                  15

Asp Arg Leu Asn Glu Leu Asp Asn Leu Val Pro Arg Asp Ala Lys Val
            20                  25                  30

Leu Val Leu Tyr Gly Gly Gly Ser Val Lys Lys Phe Gly Thr Leu Glu
        35                  40                  45

Lys Val Ile Asn Gly Leu Gly Asn Arg Gln Val Ile Glu Phe Gly Gly
    50                  55                  60

Ile Glu Pro Asn Pro Gln Phe Thr Thr Leu Met Lys Ala Val Asp Ile
65                  70                  75                  80

Val Lys Lys Glu Asn Ile Asp Phe Leu Leu Ala Val Gly Gly Gly Ser
                85                  90                  95

Val Met Asp Gly Thr Lys Phe Val Ala Leu Ala Ala Tyr Tyr Glu Gly
            100                 105                 110

Asp Asn Ala Ala Glu Ile Leu Tyr Ser Arg Glu Lys Ala Ala Ala Ile
        115                 120                 125

Asn Lys Ala Val Pro Leu Gly Thr Val Val Thr Leu Pro Ala Thr Gly
    130                 135                 140

Ser Glu Met Asn Asn Gly Gly Val Ile Ser Tyr Glu His Gly Lys Tyr
145                 150                 155                 160

Gly Phe Gly Ser Lys Leu Val Phe Pro Lys Phe Ser Val Leu Asp Pro
                165                 170                 175

Thr Leu Thr Tyr Thr Leu Pro Glu Ser Gln Val Ala Asn Gly Val Ala
            180                 185                 190

Asp Thr Phe Val His Val Leu Glu Gln Tyr Ala Thr Phe Lys Ala Glu
        195                 200                 205

Gly Arg Phe Gln Asp Arg Thr Ala Glu Gly Ile Leu Gln Thr Leu Ile

```
                        210                 215                 220
Glu Ile Gly Arg Lys Thr Ile Asp Asn Pro Thr Asp Tyr Asp Thr Arg
225                 230                 235                 240

Ala Asn Leu Val Trp Cys Ala Thr Met Ala Leu Asn Gly Leu Ile Gly
                245                 250                 255

Ala Gly Val Pro Gln Asp Trp Ser Thr His Met Ile Gly His Glu Leu
            260                 265                 270

Thr Ala Met Phe Gly Ile Asp His Gly Lys Thr Leu Ala Ile Ile Leu
        275                 280                 285

Pro Ser Ile Trp Asn Val Met Arg Glu Gln Lys Lys Gly Lys Ile Leu
290                 295                 300

Gln Tyr Ala Glu Arg Val Leu Gly Ile Thr Glu Gly Asp Asp Asp Ser
305                 310                 315                 320

Arg Ile Asp Leu Ala Ile Leu Arg Thr Arg Glu Phe Phe Glu Ser Leu
                325                 330                 335

Gly Ile Lys Thr His Leu Ser Glu Tyr Gly Val Thr Ala Asp Lys Ile
            340                 345                 350

Asp Asp Ile Val Asn Ala Leu Asp Lys His Gly Met Lys Ala Leu Ser
        355                 360                 365

Glu Thr Gly Ala Ile Thr Leu Glu Val Ser Arg Lys Ile Leu Glu Gly
    370                 375                 380

Ala Met
385

<210> SEQ ID NO 16
<211> LENGTH: 348
<212> TYPE: PRT
<213> ORGANISM: Saccharomyces cerevisiae

<400> SEQUENCE: 16

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190
```

```
Ala Met Gly Tyr Arg Val Leu Gly Ile Asp Gly Gly Lys Glu
        195                 200                 205

Glu Leu Phe Arg Ser Ile Gly Gly Glu Val Phe Ile Asp Phe Thr Lys
        210                 215                 220

Glu Lys Asp Ile Val Gly Ala Val Leu Lys Ala Thr Asp Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
        290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 17
<211> LENGTH: 348
<212> TYPE: PRT
<213> ORGANISM: Saccharomyces cerevisiae

<400> SEQUENCE: 17

Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
        210                 215                 220
```

```
Glu Lys Asp Ile Val Ser Ala Val Lys Ala Thr Asn Gly Gly Ala
225                 230                 235                 240

His Gly Ile Ile Asn Val Ser Val Ser Glu Ala Ala Ile Glu Ala Ser
            245                 250                 255

Thr Arg Tyr Cys Arg Ala Asn Gly Thr Val Val Leu Val Gly Leu Pro
        260                 265                 270

Ala Gly Ala Lys Cys Ser Ser Asp Val Phe Asn His Val Val Lys Ser
    275                 280                 285

Ile Ser Ile Val Gly Ser Tyr Val Gly Asn Arg Ala Asp Thr Arg Glu
290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345
```

<210> SEQ ID NO 18
<211> LENGTH: 375
<212> TYPE: PRT
<213> ORGANISM: Saccharomyces cerevisiae

<400> SEQUENCE: 18

```
Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
```

```
                        245                 250                 255
Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
            325                 330                 335

Ser Arg Gly Leu Ile Lys Ser Pro Ile Lys Ile Val Gly Leu Ser Glu
        340                 345                 350

Leu Pro Lys Val Tyr Asp Leu Met Glu Lys Gly Lys Ile Leu Gly Arg
    355                 360                 365

Tyr Val Val Asp Thr Ser Lys
            370                 375

<210> SEQ ID NO 19
<211> LENGTH: 382
<212> TYPE: PRT
<213> ORGANISM: Saccharomyces cerevisiae

<400> SEQUENCE: 19

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Asp Leu Asn Val Ala
    50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
            85                  90                  95

Gly Gly Gly Ser Ala His Asp Asn Ala Lys Ala Ile Ala Leu Leu Ala
        100                 105                 110

Thr Asn Gly Gly Glu Ile Gly Asp Tyr Glu Gly Val Asn Gln Ser Lys
    115                 120                 125

Lys Ala Ala Leu Pro Leu Phe Ala Ile Asn Thr Thr Ala Gly Thr Ala
130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
            165                 170                 175

Asp Pro Ser Thr Met Phe Gly Leu Pro Pro Ala Leu Thr Ala Ala Thr
        180                 185                 190

Gly Leu Asp Ala Leu Thr His Cys Ile Glu Ala Tyr Val Ser Thr Ala
    195                 200                 205

Ser Asn Pro Ile Thr Asp Ala Cys Ala Leu Lys Gly Ile Asp Leu Ile
210                 215                 220

Asn Glu Ser Leu Val Ala Ala Tyr Lys Asp Gly Lys Asp Lys Lys Ala
225                 230                 235                 240
```

```
Arg Thr Asp Met Cys Tyr Ala Glu Tyr Leu Ala Gly Met Ala Phe Asn
            245                 250                 255

Asn Ala Ser Leu Gly Tyr Val His Ala Leu Ala His Gln Leu Gly Gly
        260                 265                 270

Phe Tyr His Leu Pro His Gly Val Cys Asn Ala Val Leu Leu Pro His
    275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
    370                 375                 380

<210> SEQ ID NO 20
<211> LENGTH: 331
<212> TYPE: PRT
<213> ORGANISM: Bacillus subtilis

<400> SEQUENCE: 20

Met Glu Tyr Thr Ser Ile Ala Asp Thr Gly Ile Glu Ala Ser Arg Ile
1               5                   10                  15

Gly Leu Gly Thr Trp Ala Ile Gly Gly Thr Met Trp Gly Gly Thr Asp
            20                  25                  30

Glu Lys Thr Ser Ile Glu Thr Ile Arg Ala Ala Leu Asp Gln Gly Ile
        35                  40                  45

Thr Leu Ile Asp Thr Ala Pro Ala Tyr Gly Phe Gly Gln Ser Glu Glu
    50                  55                  60

Ile Val Gly Lys Ala Ile Lys Glu Tyr Gly Lys Arg Asp Gln Val Ile
65                  70                  75                  80

Leu Ala Thr Lys Thr Ala Leu Asp Trp Lys Asn Asn Gln Leu Phe Arg
                85                  90                  95

His Ala Asn Arg Ala Arg Ile Val Glu Glu Val Glu Asn Ser Leu Lys
            100                 105                 110

Arg Leu Gln Thr Asp Tyr Ile Asp Leu Tyr Gln Val His Trp Pro Asp
        115                 120                 125

Pro Leu Val Pro Ile Glu Glu Thr Ala Glu Val Met Lys Glu Leu Tyr
    130                 135                 140

Asp Ala Gly Lys Ile Arg Ala Ile Gly Val Ser Asn Phe Ser Ile Glu
145                 150                 155                 160

Gln Met Asp Thr Phe Arg Ala Val Ala Pro Leu His Thr Ile Gln Pro
                165                 170                 175

Pro Tyr Asn Leu Phe Glu Arg Glu Met Glu Glu Ser Val Leu Pro Tyr
            180                 185                 190

Ala Lys Asp Asn Lys Ile Thr Thr Leu Leu Tyr Gly Ser Leu Cys Arg
        195                 200                 205

Gly Leu Leu Thr Gly Lys Met Thr Glu Glu Tyr Thr Phe Glu Gly Asp
    210                 215                 220

Asp Leu Arg Asn His Asp Pro Lys Phe Gln Lys Pro Arg Phe Lys Glu
225                 230                 235                 240
```

```
Tyr Leu Ser Ala Val Asn Gln Leu Asp Lys Leu Ala Lys Thr Arg Tyr
                245                 250                 255

Gly Lys Ser Val Ile His Leu Ala Val Arg Trp Ile Leu Asp Gln Pro
            260                 265                 270

Gly Ala Asp Ile Ala Leu Trp Gly Ala Arg Lys Pro Gly Gln Leu Glu
        275                 280                 285

Ala Leu Ser Glu Ile Thr Gly Trp Thr Leu Asn Ser Glu Asp Gln Lys
    290                 295                 300

Asp Ile Asn Thr Ile Leu Glu Asn Thr Ile Ser Asp Pro Val Gly Pro
305                 310                 315                 320

Glu Phe Met Ala Pro Pro Thr Arg Glu Glu Ile
                325                 330

<210> SEQ ID NO 21
<211> LENGTH: 332
<212> TYPE: PRT
<213> ORGANISM: Gluconobacter oxydans

<400> SEQUENCE: 21

Met Ala Ser Asp Thr Ile Arg Ile Pro Gly Ile Asp Thr Pro Leu Ser
1               5                   10                  15

Arg Val Ala Leu Gly Thr Trp Ala Ile Gly Gly Trp Met Trp Gly Gly
            20                  25                  30

Pro Asp Asp Asn Gly Val Arg Thr Ile His Ala Ala Leu Asp Glu
        35                  40                  45

Gly Ile Asn Leu Ile Asp Thr Ala Pro Val Tyr Gly Phe Gly His Ser
    50                  55                  60

Glu Glu Ile Val Gly Arg Ala Leu Ala Glu Lys Pro Asn Lys Ala His
65                  70                  75                  80

Val Ala Thr Lys Leu Gly Leu His Trp Val Gly Asp Glu Lys Asn
                85                  90                  95

Met Lys Val Phe Arg Asp Ser Arg Pro Ala Arg Ile Arg Lys Glu Val
            100                 105                 110

Glu Asp Ser Leu Arg Arg Leu Arg Val Glu Thr Ile Asp Leu Glu Gln
        115                 120                 125

Ile His Trp Pro Asp Asp Lys Thr Pro Ile Asp Glu Ser Ala Arg Glu
    130                 135                 140

Leu Gln Lys Leu His Gln Asp Gly Lys Ile Arg Ala Leu Gly Val Ser
145                 150                 155                 160

Asn Phe Ser Pro Glu Gln Met Asp Ile Phe Arg Glu Val Ala Pro Leu
                165                 170                 175

Ala Thr Ile Gln Pro Pro Leu Asn Leu Phe Glu Arg Thr Ile Glu Lys
            180                 185                 190

Asp Ile Leu Pro Tyr Ala Glu Lys His Asn Ala Val Val Leu Ala Tyr
        195                 200                 205

Gly Ala Leu Cys Arg Gly Leu Leu Thr Gly Lys Met Asn Arg Asp Thr
    210                 215                 220

Thr Phe Pro Lys Asp Asp Leu Arg Ser Asn Asp Pro Lys Phe Gln Lys
225                 230                 235                 240

Pro Asn Phe Glu Lys Tyr Leu Ala Ala Met Asp Glu Phe Glu Lys Leu
                245                 250                 255

Ala Glu Lys Arg Gly Lys Ser Val Met Ala Phe Ala Val Arg Trp Val
            260                 265                 270

Leu Asp Gln Gly Pro Val Ile Ala Leu Trp Gly Ala Arg Lys Pro Gly
```

```
                  275                 280                 285
Gln Val Ser Gly Val Lys Asp Val Phe Gly Trp Ser Leu Thr Asp Glu
    290                 295                 300
Glu Lys Lys Ala Val Asp Asp Ile Leu Ala Arg His Val Pro Asn Pro
305                 310                 315                 320
Ile Asp Pro Thr Phe Met Ala Pro Pro Ala Arg Asp
                325                 330

<210> SEQ ID NO 22
<211> LENGTH: 339
<212> TYPE: PRT
<213> ORGANISM: Escherichia coli

<400> SEQUENCE: 22

Met Ser Met Ile Lys Ser Tyr Ala Ala Lys Glu Ala Gly Gly Glu Leu
1               5                   10                  15
Glu Val Tyr Glu Tyr Asp Pro Gly Glu Leu Arg Pro Gln Asp Val Glu
            20                  25                  30
Val Gln Val Asp Tyr Cys Gly Ile Cys His Ser Asp Leu Ser Met Ile
        35                  40                  45
Asp Asn Glu Trp Gly Phe Ser Gln Tyr Pro Leu Val Ala Gly His Glu
    50                  55                  60
Val Ile Gly Arg Val Val Ala Leu Gly Ser Ala Ala Gln Asp Lys Gly
65                  70                  75                  80
Leu Gln Val Gly Gln Arg Val Gly Ile Gly Trp Thr Ala Arg Ser Cys
                85                  90                  95
Gly His Cys Asp Ala Cys Ile Ser Gly Asn Gln Ile Asn Cys Glu Gln
            100                 105                 110
Gly Ala Val Pro Thr Ile Met Asn Arg Gly Gly Phe Ala Glu Lys Leu
        115                 120                 125
Arg Ala Asp Trp Gln Trp Val Ile Pro Leu Pro Glu Asn Ile Asp Ile
    130                 135                 140
Glu Ser Ala Gly Pro Leu Leu Cys Gly Gly Ile Thr Val Phe Lys Pro
145                 150                 155                 160
Leu Leu Met His His Ile Thr Ala Thr Ser Arg Val Gly Val Ile Gly
                165                 170                 175
Ile Gly Gly Leu Gly His Ile Ala Ile Lys Leu Leu His Ala Met Gly
            180                 185                 190
Cys Glu Val Thr Ala Phe Ser Ser Asn Pro Ala Lys Glu Gln Glu Val
        195                 200                 205
Leu Ala Met Gly Ala Asp Lys Val Val Asn Ser Arg Asp Pro Gln Ala
    210                 215                 220
Leu Lys Ala Leu Ala Gly Gln Phe Asp Leu Ile Ile Asn Thr Val Asn
225                 230                 235                 240
Val Ser Leu Asp Trp Gln Pro Tyr Phe Glu Ala Leu Thr Tyr Gly Gly
                245                 250                 255
Asn Phe His Thr Val Gly Ala Val Leu Thr Pro Leu Ser Val Pro Ala
            260                 265                 270
Phe Thr Leu Ile Ala Gly Asp Arg Ser Val Ser Gly Ser Ala Thr Gly
        275                 280                 285
Thr Pro Tyr Glu Leu Arg Lys Leu Met Arg Phe Ala Ala Arg Ser Lys
    290                 295                 300
Val Ala Pro Thr Thr Glu Leu Phe Pro Met Ser Lys Ile Asn Asp Ala
305                 310                 315                 320
```

Ile Gln His Val Arg Asp Gly Lys Ala Arg Tyr Arg Val Val Leu Lys
                325                 330                 335

Ala Asp Phe

<210> SEQ ID NO 23
<211> LENGTH: 315
<212> TYPE: PRT
<213> ORGANISM: Arabidopsis thaliana

<400> SEQUENCE: 23

Met Ala Asn Ala Ile Thr Phe Phe Lys Leu Asn Thr Gly Ala Lys Phe
1               5                   10                  15

Pro Ser Val Gly Leu Gly Thr Trp Gln Ala Ser Pro Gly Leu Val Gly
                20                  25                  30

Asp Ala Ala Ala Ala Val Lys Ile Gly Tyr Arg His Ile Asp Cys
                35                  40                  45

Ala Gln Ile Tyr Gly Asn Glu Lys Glu Ile Gly Ala Val Leu Lys Lys
            50                  55                  60

Leu Phe Glu Asp Arg Val Val Lys Arg Glu Asp Leu Phe Ile Thr Ser
65                  70                  75                  80

Lys Leu Trp Cys Thr Asp His Asp Pro Gln Asp Val Pro Glu Ala Leu
                85                  90                  95

Asn Arg Thr Leu Lys Asp Leu Gln Leu Glu Tyr Val Asp Leu Tyr Leu
                100                 105                 110

Ile His Trp Pro Ala Arg Ile Lys Lys Gly Ser Val Gly Ile Lys Pro
            115                 120                 125

Glu Asn Leu Leu Pro Val Asp Ile Pro Ser Thr Trp Lys Ala Met Glu
130                 135                 140

Ala Leu Tyr Asp Ser Gly Lys Ala Arg Ala Ile Gly Val Ser Asn Phe
145                 150                 155                 160

Ser Thr Lys Lys Leu Ala Asp Leu Leu Glu Leu Ala Arg Val Pro Pro
                165                 170                 175

Ala Val Asn Gln Val Glu Cys His Pro Ser Trp Arg Gln Thr Lys Leu
                180                 185                 190

Gln Glu Phe Cys Lys Ser Lys Gly Val His Leu Ser Ala Tyr Ser Pro
            195                 200                 205

Leu Gly Ser Pro Gly Thr Thr Trp Leu Lys Ser Asp Val Leu Lys Asn
210                 215                 220

Pro Ile Leu Asn Met Val Ala Glu Lys Leu Gly Lys Ser Pro Ala Gln
225                 230                 235                 240

Val Ala Leu Arg Trp Gly Leu Gln Met Gly His Ser Val Leu Pro Lys
                245                 250                 255

Ser Thr Asn Glu Gly Arg Ile Lys Glu Asn Phe Asn Val Phe Asp Trp
                260                 265                 270

Ser Ile Pro Asp Tyr Met Phe Ala Lys Phe Ala Glu Ile Glu Gln Ala
            275                 280                 285

Arg Leu Val Thr Gly Ser Phe Leu Val His Glu Thr Leu Ser Pro Tyr
290                 295                 300

Lys Ser Ile Glu Glu Leu Trp Asp Gly Glu Ile
305                 310                 315

<210> SEQ ID NO 24
<211> LENGTH: 284
<212> TYPE: PRT
<213> ORGANISM: Leishmania donovani

<400> SEQUENCE: 24

```
Met Ala Asp Val Gly Lys Ala Met Val Thr Leu Ser Asn Gly Val Gln
1               5                   10                  15

Met Pro Gln Leu Gly Leu Gly Val Trp Gln Ser Pro Ala Gly Glu Val
            20                  25                  30

Thr Ala Asn Ala Val Lys Trp Ala Leu Cys Ala Gly Tyr Arg His Ile
        35                  40                  45

Asp Thr Ala Ala Ile Tyr Lys Asn Glu Glu Ser Val Gly Ala Gly Leu
    50                  55                  60

Arg Ala Ser Gly Val Pro Arg Glu Asp Val Phe Ile Thr Thr Lys Leu
65                  70                  75                  80

Trp Asn Thr Glu Gln Gly Tyr Glu Ser Thr Leu Ala Ala Phe Glu Glu
                85                  90                  95

Ser Arg Gln Lys Leu Gly Val Asp Tyr Ile Asp Leu Tyr Leu Ile His
            100                 105                 110

Trp Pro Arg Gly Lys Asp Ile Val Ser Lys Glu Gly Lys Lys Tyr Leu
        115                 120                 125

Asp Ser Trp Arg Ala Phe Glu Gln Leu Tyr Lys Asp Lys Lys Val Arg
    130                 135                 140

Ala Ile Gly Val Ser Asn Phe His Ile His His Leu Glu Asp Val Leu
145                 150                 155                 160

Ala Met Cys Thr Val Thr Pro Met Val Asn Gln Val Glu Leu His Pro
                165                 170                 175

Leu Asn Asn Gln Ala Glu Leu Arg Ala Phe Cys Asp Ala Lys Gln Ile
            180                 185                 190

Lys Val Glu Ala Trp Ser Pro Leu Gly Gln Gly Lys Leu Leu Ser Asn
        195                 200                 205

Pro Ile Leu Ala Ala Ile Gly Ala Lys Tyr Asn Lys Thr Ala Ala Gln
    210                 215                 220

Val Ile Leu Arg Trp Asn Ile Gln Lys Asn Leu Ile Thr Ile Pro Lys
225                 230                 235                 240

Ser Val His Lys Glu Arg Ile Glu Glu Asn Ala Asp Val Phe Asn Phe
                245                 250                 255

Glu Leu Asp Ala Glu Asp Val Met Ser Ile Asp Ala Leu Asn Thr Asn
            260                 265                 270

Ser Arg Tyr Gly Pro Asp Pro Asp Glu Ala Gln Phe
        275                 280
```

<210> SEQ ID NO 25
<211> LENGTH: 349
<212> TYPE: PRT
<213> ORGANISM: Escherichia coli

<400> SEQUENCE: 25

```
Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
            20                  25                  30

Glu Ile Ala Tyr Cys Gly Val Cys His Ser Asp Leu His Gln Val Arg
        35                  40                  45

Ser Glu Trp Ala Gly Thr Val Tyr Pro Cys Val Pro Gly His Glu Ile
    50                  55                  60

Val Gly Arg Val Val Ala Val Gly Asp Gln Val Glu Lys Tyr Ala Pro
65                  70                  75                  80
```

```
Gly Asp Leu Val Gly Val Gly Cys Ile Val Asp Ser Cys Lys His Cys
            85                  90                  95

Glu Glu Cys Glu Asp Gly Leu Glu Asn Tyr Cys Asp His Met Thr Gly
            100                 105                 110

Thr Tyr Asn Ser Pro Thr Pro Asp Glu Pro Gly His Thr Leu Gly Gly
            115                 120                 125

Tyr Ser Gln Gln Ile Val Val His Glu Arg Tyr Val Leu Arg Ile Arg
            130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
            165                 170                 175

Lys Val Gly Val Val Gly Ile Gly Gly Leu Gly His Met Gly Ile Lys
            180                 185                 190

Leu Ala His Ala Met Gly Ala His Val Val Ala Phe Thr Thr Ser Glu
            195                 200                 205

Ala Lys Arg Glu Ala Ala Lys Ala Leu Gly Ala Asp Glu Val Val Asn
            210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
            245                 250                 255

Leu Leu Lys Arg Asp Gly Thr Met Thr Leu Val Gly Ala Pro Ala Thr
            260                 265                 270

Pro His Lys Ser Pro Glu Val Phe Asn Leu Ile Met Lys Arg Arg Ala
            275                 280                 285

Ile Ala Gly Ser Met Ile Gly Gly Ile Pro Glu Thr Gln Glu Met Leu
            290                 295                 300

Asp Phe Cys Ala Glu His Gly Ile Val Ala Asp Ile Glu Met Ile Arg
305                 310                 315                 320

Ala Asp Gln Ile Asn Glu Ala Tyr Glu Arg Met Leu Arg Gly Asp Val
            325                 330                 335

Lys Tyr Arg Phe Val Ile Asp Asn Arg Thr Leu Thr Asp
            340                 345

<210> SEQ ID NO 26
<211> LENGTH: 346
<212> TYPE: PRT
<213> ORGANISM: Escherichia coli

<400> SEQUENCE: 26

Met Gln Tyr His Arg Ile Pro His Ser Ser Leu Glu Val Ser Thr Leu
1               5                   10                  15

Gly Leu Gly Thr Met Thr Phe Gly Glu Gln Asn Ser Glu Ala Asp Ala
            20                  25                  30

His Ala Gln Leu Asp Tyr Ala Val Ala Gln Gly Ile Asn Leu Ile Asp
            35                  40                  45

Val Ala Glu Met Tyr Pro Val Pro Arg Pro Glu Thr Gln Gly Leu
            50                  55                  60

Thr Glu Thr Tyr Val Gly Asn Trp Leu Ala Lys His Gly Ser Arg Glu
65                  70                  75                  80

Lys Leu Ile Ile Ala Ser Lys Val Ser Gly Pro Ser Arg Asn Asn Asp
            85                  90                  95

Lys Gly Ile Arg Pro Asp Gln Ala Leu Asp Arg Lys Asn Ile Arg Glu
            100                 105                 110
```

Ala Leu His Asp Ser Leu Lys Arg Leu Gln Thr Asp Tyr Leu Asp Leu
            115                 120                 125

Tyr Gln Val His Trp Pro Gln Arg Pro Thr Asn Cys Phe Gly Lys Leu
    130                 135                 140

Gly Tyr Ser Trp Thr Asp Ser Ala Pro Ala Val Ser Leu Leu Asp Thr
145                 150                 155                 160

Leu Asp Ala Leu Ala Glu Tyr Gln Arg Ala Gly Lys Ile Arg Tyr Ile
                165                 170                 175

Gly Val Ser Asn Glu Thr Ala Phe Gly Val Met Arg Tyr Leu His Leu
            180                 185                 190

Ala Asp Lys His Asp Leu Pro Arg Ile Val Thr Ile Gln Asn Pro Tyr
        195                 200                 205

Ser Leu Leu Asn Arg Ser Phe Glu Val Gly Leu Ala Glu Val Ser Gln
    210                 215                 220

Tyr Glu Gly Val Glu Leu Leu Ala Tyr Ser Cys Leu Gly Phe Gly Thr
225                 230                 235                 240

Leu Thr Gly Lys Tyr Leu Asn Gly Ala Lys Pro Ala Gly Ala Arg Asn
                245                 250                 255

Thr Leu Phe Ser Arg Phe Thr Arg Tyr Ser Gly Glu Thr Gln Lys
            260                 265                 270

Ala Val Ala Ala Tyr Val Asp Ile Ala Arg Arg His Gly Leu Asp Pro
        275                 280                 285

Ala Gln Met Ala Leu Ala Phe Val Arg Arg Gln Pro Phe Val Ala Ser
    290                 295                 300

Thr Leu Leu Gly Ala Thr Thr Met Asp Gln Leu Lys Thr Asn Ile Glu
305                 310                 315                 320

Ser Leu His Leu Glu Leu Ser Glu Asp Val Leu Ala Glu Ile Glu Ala
                325                 330                 335

Val His Gln Val Tyr Thr Tyr Pro Ala Pro
            340                 345

<210> SEQ ID NO 27
<211> LENGTH: 399
<212> TYPE: PRT
<213> ORGANISM: Thermoanaerobacter ethaolicus

<400> SEQUENCE: 27

Met Trp Glu Thr Lys Ile Asn Pro Asn Lys Val Phe Glu Leu Arg Cys
1               5                   10                  15

Lys Asn Thr Thr Tyr Phe Gly Ile Gly Ser Ile Lys Lys Ile Lys Asp
            20                  25                  30

Ile Leu Glu Val Leu Lys Asn Lys Gly Ile Asn Asn Val Ile Leu Val
        35                  40                  45

Thr Gly Lys Gly Ser Tyr Lys Ala Ser Gly Ala Trp Asp Val Val Lys
50                  55                  60

Pro Ala Leu Glu Thr Leu Gly Phe Lys Tyr Ser Leu Tyr Asp Lys Val
65                  70                  75                  80

Gly Pro Asn Pro Thr Val Asp Met Ile Asp Glu Ala Ala Lys Ile Gly
                85                  90                  95

Arg Glu Thr Gly Ala Lys Ala Val Ile Gly Ile Gly Gly Gly Ser Pro
            100                 105                 110

Ile Asp Thr Ala Lys Ser Val Ala Val Leu Leu Glu Tyr Thr Asp Lys
        115                 120                 125

Asn Ala Arg Glu Leu Tyr Glu Gln Lys Phe Ile Pro Glu Lys Ala Ala

```
            130                 135                 140
Pro Ile Ile Ala Ile Asn Leu Thr His Gly Thr Gly Thr Glu Val Asp
145                 150                 155                 160

Arg Phe Ala Val Ala Thr Ile Pro Glu Lys Asn Tyr Lys Pro Ala Ile
                165                 170                 175

Ala Tyr Asp Cys Leu Tyr Pro Met Tyr Ala Ile Asp Asp Pro Ser Leu
                180                 185                 190

Met Thr Lys Leu Asp Lys Lys Gln Thr Ile Ala Val Thr Ile Asp Ala
                195                 200                 205

Leu Asn His Val Thr Glu Ala Ala Thr Thr Leu Val Ala Ser Pro Tyr
210                 215                 220

Ser Val Leu Met Ala Lys Glu Thr Val Arg Leu Ile Val Arg Tyr Leu
225                 230                 235                 240

Pro Ala Ala Val Asn Asp Pro Glu Asn Leu Val Ala Arg Tyr Tyr Leu
                245                 250                 255

Leu Tyr Ala Ser Ala Leu Ala Gly Ile Ser Phe Asp Asn Gly Leu Leu
                260                 265                 270

His Leu Thr His Ala Leu Glu His Pro Leu Ser Ala Val Lys Pro Glu
                275                 280                 285

Ile Ala His Gly Leu Gly Leu Gly Ala Ile Leu Pro Ala Val Val Lys
                290                 295                 300

Ala Ile Tyr Pro Ser Val Ala Glu Val Leu Ala Glu Val Tyr Ser Pro
305                 310                 315                 320

Ile Val Pro Gly Leu Lys Gly Leu Pro Ala Glu Ala Glu Tyr Val Ala
                325                 330                 335

Lys Lys Val Glu Glu Trp Leu Phe Lys Val Gly Cys Thr Gln Lys Leu
                340                 345                 350

Ser Asp Phe Gly Phe Thr Lys Glu Asp Ile Pro Thr Leu Val Arg Leu
                355                 360                 365

Ala Lys Thr Thr Pro Ser Leu Asp Gly Leu Leu Ser Asn Ala Pro Val
                370                 375                 380

Glu Ala Thr Glu Ala Val Ile Ala Lys Ile Tyr Glu Glu Ser Phe
385                 390                 395

<210> SEQ ID NO 28
<211> LENGTH: 346
<212> TYPE: PRT
<213> ORGANISM: Bacillus subtilis

<400> SEQUENCE: 28

Met Lys Ala Ala Arg Trp His Asn Gln Lys Asp Ile Arg Ile Glu His
1               5                   10                  15

Ile Glu Glu Pro Lys Thr Glu Pro Gly Lys Val Lys Ile Lys Val Lys
                20                  25                  30

Trp Cys Gly Ile Cys Gly Ser Asp Leu His Glu Tyr Leu Gly Gly Pro
            35                  40                  45

Ile Phe Ile Pro Val Asp Lys Pro His Pro Leu Thr Asn Glu Thr Ala
            50                  55                  60

Pro Val Thr Met Gly His Glu Phe Ser Gly Glu Val Val Glu Val Gly
65              70                  75                  80

Glu Gly Val Glu Asn Tyr Lys Val Gly Asp Arg Val Val Val Glu Pro
                85                  90                  95

Ile Phe Ala Thr His Gly His Gln Gly Ala Tyr Asn Leu Asp Glu Gln
            100                 105                 110
```

```
Met Gly Phe Leu Gly Leu Ala Gly Gly Gly Gly Phe Ser Glu Tyr
            115                 120                 125

Val Ser Val Asp Glu Glu Leu Leu Phe Lys Leu Pro Asp Glu Leu Ser
    130                 135                 140

Tyr Glu Gln Gly Ala Leu Val Glu Pro Ser Ala Val Ala Leu Tyr Ala
145                 150                 155                 160

Val Arg Ser Ser Lys Leu Lys Ala Gly Asp Lys Ala Ala Val Phe Gly
                165                 170                 175

Cys Gly Pro Ile Gly Leu Leu Val Ile Glu Ala Leu Lys Ala Ala Gly
            180                 185                 190

Ala Thr Asp Ile Tyr Ala Val Glu Leu Ser Pro Glu Arg Gln Gln Lys
        195                 200                 205

Ala Glu Glu Leu Gly Ala Ile Ile Val Asp Pro Ser Lys Thr Asp Asp
    210                 215                 220

Val Val Ala Glu Ile Ala Glu Arg Thr Gly Gly Val Asp Val Ala
225                 230                 235                 240

Phe Glu Val Thr Gly Val Pro Val Val Leu Arg Gln Ala Ile Gln Ser
                245                 250                 255

Thr Thr Ile Ala Gly Glu Thr Val Ile Val Ser Ile Trp Glu Lys Gly
            260                 265                 270

Ala Glu Ile His Pro Asn Asp Ile Val Ile Lys Glu Arg Thr Val Lys
        275                 280                 285

Gly Ile Ile Gly Tyr Arg Asp Ile Phe Pro Ala Val Leu Ser Leu Met
    290                 295                 300

Lys Glu Gly Tyr Phe Ser Ala Asp Lys Leu Val Thr Lys Lys Ile Val
305                 310                 315                 320

Leu Asp Asp Leu Ile Glu Glu Gly Phe Gly Ala Leu Ile Lys Glu Lys
                325                 330                 335

Ser Gln Val Lys Ile Leu Val Arg Pro Asn
            340                 345

<210> SEQ ID NO 29
<211> LENGTH: 382
<212> TYPE: PRT
<213> ORGANISM: Saccharomyces cerevisiae

<400> SEQUENCE: 29

Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
                20                  25                  30

Val Ser Trp Cys Gly Ile Cys Gly Ser Asp Leu His Glu Tyr Leu Asp
            35                  40                  45

Gly Pro Ile Phe Met Pro Lys Asp Gly Glu Cys His Lys Leu Ser Asn
        50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110

Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140
```

```
Gly Phe Ala Glu Gln Val Val Ser Gln His His Ile Ile Pro Val
145                 150                 155                 160

Pro Lys Glu Ile Pro Leu Asp Val Ala Ala Leu Val Glu Pro Leu Ser
            165                 170                 175

Val Thr Trp His Ala Val Lys Ile Ser Gly Phe Lys Lys Gly Ser Ser
        180                 185                 190

Ala Leu Val Leu Gly Ala Gly Pro Ile Gly Leu Cys Thr Ile Leu Val
            195                 200                 205

Leu Lys Gly Met Gly Ala Ser Lys Ile Val Val Ser Glu Ile Ala Glu
        210                 215                 220

Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
            245                 250                 255

Ser His Asp Gly Phe Asp Tyr Ser Tyr Asp Cys Ser Gly Ile Gln Val
        260                 265                 270

Thr Phe Glu Thr Ser Leu Lys Ala Leu Thr Phe Lys Gly Thr Ala Thr
    275                 280                 285

Asn Ile Ala Val Trp Gly Pro Lys Pro Val Pro Phe Gln Pro Met Asp
290                 295                 300

Val Thr Leu Gln Glu Lys Val Met Thr Gly Ser Ile Gly Tyr Val Val
305                 310                 315                 320

Glu Asp Phe Glu Glu Val Val Arg Ala Ile His Asn Gly Asp Ile Ala
            325                 330                 335

Met Glu Asp Cys Lys Gln Leu Ile Thr Gly Lys Gln Arg Ile Glu Asp
        340                 345                 350

Gly Trp Glu Lys Gly Phe Gln Glu Leu Met Asp His Lys Glu Ser Asn
    355                 360                 365

Val Lys Ile Leu Leu Thr Pro Asn Asn His Gly Glu Met Lys
370                 375                 380

<210> SEQ ID NO 30
<211> LENGTH: 258
<212> TYPE: PRT
<213> ORGANISM: Corynebacterium glutamicum

<400> SEQUENCE: 30

Met Ser Lys Val Ala Met Val Thr Gly Gly Ala Gln Gly Ile Gly Arg
1               5                   10                  15

Gly Ile Ser Glu Lys Leu Ala Ala Asp Gly Phe Asp Ile Ala Val Ala
            20                  25                  30

Asp Leu Pro Gln Gln Glu Glu Gln Ala Ala Glu Thr Ile Lys Leu Ile
        35                  40                  45

Glu Ala Ala Gly Gln Lys Ala Val Phe Val Gly Leu Asp Val Thr Asp
    50                  55                  60

Lys Ala Asn Phe Asp Ser Ala Ile Asp Glu Ala Glu Lys Leu Gly
65                  70                  75                  80

Gly Phe Asp Val Leu Val Asn Asn Ala Gly Ile Ala Gln Ile Lys Pro
            85                  90                  95

Leu Leu Glu Val Thr Glu Glu Asp Leu Lys Gln Ile Tyr Ser Val Asn
        100                 105                 110

Val Phe Ser Val Phe Phe Gly Ile Gln Ala Ala Ser Arg Lys Phe Asp
    115                 120                 125

Glu Leu Gly Val Lys Gly Lys Ile Ile Asn Ala Ala Ser Ile Ala Ala
```

```
            130                 135                 140
Ile Gln Gly Phe Pro Ile Leu Ser Ala Tyr Ser Thr Thr Lys Phe Ala
145                 150                 155                 160

Val Arg Gly Leu Thr Gln Ala Ala Gln Glu Leu Ala Pro Lys Gly
                165                 170                 175

His Thr Val Asn Ala Tyr Ala Pro Gly Ile Val Gly Thr Gly Met Trp
                180                 185                 190

Glu Gln Ile Asp Ala Glu Leu Ser Lys Ile Asn Gly Lys Pro Ile Gly
                195                 200                 205

Glu Asn Phe Lys Glu Tyr Ser Ser Ser Ile Ala Leu Gly Arg Pro Ser
            210                 215                 220

Val Pro Glu Asp Val Ala Gly Leu Val Ser Phe Leu Ala Ser Glu Asn
225                 230                 235                 240

Ser Asn Tyr Ile Thr Gly Gln Val Met Leu Val Asp Gly Gly Met Leu
                245                 250                 255

Tyr Asn

<210> SEQ ID NO 31
<211> LENGTH: 256
<212> TYPE: PRT
<213> ORGANISM: Klebsiella pneumoniae

<400> SEQUENCE: 31

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
                20                  25                  30

Asp Tyr Asn Asp Ala Thr Ala Lys Ala Val Ala Ser Glu Ile Asn Gln
            35                  40                  45

Ala Gly Gly Arg Ala Met Ala Val Lys Val Asp Val Ser Asp Arg Asp
        50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
                100                 105                 110

Gly Val Ile Trp Gly Ile Gln Ala Ala Val Glu Ala Phe Lys Lys Glu
            115                 120                 125

Gly His Gly Gly Lys Ile Ile Asn Ala Cys Ser Gln Ala Gly His Val
        130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
                180                 185                 190

Ile Asp Arg Gln Val Ser Glu Ala Ala Gly Lys Pro Leu Gly Tyr Gly
            195                 200                 205

Thr Ala Glu Phe Ala Lys Arg Ile Thr Leu Gly Arg Leu Ser Glu Pro
        210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
```

<210> SEQ ID NO 32
<211> LENGTH: 251
<212> TYPE: PRT
<213> ORGANISM: Serratia marcescens

<400> SEQUENCE: 32

Met Arg Phe Asp Asn Lys Val Val Ile Thr Gly Ala Gly Thr Gly
1               5                   10                  15

Met Gly Glu Ala Ala Arg Arg Phe Ser Ala Glu Gly Ala Ile Val
            20                  25                  30

Val Leu Ala Asp Trp Ala Lys Glu Ala Val Asp Lys Val Ala Ala Ser
            35                  40                  45

Leu Pro Lys Gly Arg Ala Met Ala Val His Ile Asp Val Ser Asp His
    50                  55                  60

Val Ala Val Glu Lys Met Met Asn Glu Val Ala Glu Lys Leu Gly Arg
65                  70                  75                  80

Ile Asp Val Leu Leu Asn Asn Ala Gly Val His Val Ala Gly Ser Val
                85                  90                  95

Leu Glu Thr Ser Val Asp Asp Trp Arg Arg Ile Ala Gly Val Asp Ile
            100                 105                 110

Asp Gly Val Val Phe Cys Ser Lys Phe Ala Leu Pro His Leu Leu Lys
            115                 120                 125

Thr Lys Gly Cys Ile Val Asn Thr Ala Ser Val Ser Gly Leu Gly Gly
130                 135                 140

Asp Trp Gly Ala Ala Tyr Tyr Cys Ala Ala Lys Gly Ala Val Val Asn
145                 150                 155                 160

Leu Thr Arg Ala Met Ala Leu Asp His Gly Gly Asp Gly Val Arg Ile
                165                 170                 175

Asn Ser Val Cys Pro Ser Leu Val Lys Thr Asn Met Thr Asn Gly Trp
            180                 185                 190

Pro Gln Glu Ile Arg Asp Lys Phe Asn Glu Arg Ile Ala Leu Gly Arg
        195                 200                 205

Ala Ala Glu Pro Glu Val Ala Ala Val Met Ala Phe Leu Ala Ser
    210                 215                 220

Asp Asp Ala Ser Phe Ile Asn Gly Ala Asn Ile Pro Val Asp Gly Gly
225                 230                 235                 240

Ala Thr Ala Ser Asp Gly Gln Gln Asn Ile Val
                245                 250

<210> SEQ ID NO 33
<211> LENGTH: 367
<212> TYPE: PRT
<213> ORGANISM: Escherichia coli

<400> SEQUENCE: 33

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
            35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala

| | | | | | | | | | | | | | | | |
|---|---|---|---|---|---|---|---|---|---|---|---|---|---|---|---|

```
                65                  70                  75                  80

Glu Thr Ala Gln Cys Gly Ala Ile Leu Gly Ile Gly Gly Lys Thr
                        85                  90                  95

Leu Asp Thr Ala Lys Ala Leu Ala His Phe Met Gly Val Pro Val Ala
                            100                 105                 110

Ile Ala Pro Thr Ile Ala Ser Thr Asp Ala Pro Cys Ser Ala Leu Ser
                        115                 120                 125

Val Ile Tyr Thr Asp Glu Gly Glu Phe Asp Arg Tyr Leu Leu Leu Pro
                    130                 135                 140

Asn Asn Pro Asn Met Val Ile Val Asp Thr Lys Ile Val Ala Gly Ala
        145                 150                 155                 160

Pro Ala Arg Leu Leu Ala Ala Gly Ile Gly Asp Ala Leu Ala Thr Trp
                            165                 170                 175

Phe Glu Ala Arg Ala Cys Ser Arg Ser Gly Ala Thr Thr Met Ala Gly
                        180                 185                 190

Gly Lys Cys Thr Gln Ala Ala Leu Ala Leu Ala Glu Leu Cys Tyr Asn
                        195                 200                 205

Thr Leu Leu Glu Glu Gly Glu Lys Ala Met Leu Ala Ala Glu Gln His
                    210                 215                 220

Val Val Thr Pro Ala Leu Glu Arg Val Ile Glu Ala Asn Thr Tyr Leu
        225                 230                 235                 240

Ser Gly Val Gly Phe Glu Ser Gly Gly Leu Ala Ala His Ala Val
                            245                 250                 255

His Asn Gly Leu Thr Ala Ile Pro Asp Ala His His Tyr Tyr His Gly
                        260                 265                 270

Glu Lys Val Ala Phe Gly Thr Leu Thr Gln Leu Val Leu Glu Asn Ala
                        275                 280                 285

Pro Val Glu Glu Ile Glu Thr Val Ala Ala Leu Ser His Ala Val Gly
                    290                 295                 300

Leu Pro Ile Thr Leu Ala Gln Leu Asp Ile Lys Glu Asp Val Pro Ala
        305                 310                 315                 320

Lys Met Arg Ile Val Ala Glu Ala Ala Cys Ala Glu Gly Glu Thr Ile
                            325                 330                 335

His Asn Met Pro Gly Gly Ala Thr Pro Asp Gln Val Tyr Ala Ala Leu
                        340                 345                 350

Leu Val Ala Asp Gln Tyr Gly Gln Arg Phe Leu Gln Glu Trp Glu
                    355                 360                 365

<210> SEQ ID NO 34
<211> LENGTH: 258
<212> TYPE: PRT
<213> ORGANISM: Corynebacterium glutamicum

<400> SEQUENCE: 34

Met Ser Lys Val Ala Met Val Thr Gly Gly Ala Gln Gly Ile Gly Arg
1               5                   10                  15

Gly Ile Ser Glu Lys Leu Ala Ala Asp Gly Phe Asp Ile Ala Val Ala
                20                  25                  30

Asp Leu Pro Gln Gln Glu Glu Gln Ala Ala Glu Thr Ile Lys Leu Ile
            35                  40                  45

Glu Ala Ala Asp Gln Lys Ala Val Phe Val Gly Leu Asp Val Thr Asp
        50                  55                  60

Lys Ala Asn Phe Asp Ser Ala Ile Asp Glu Ala Ala Glu Lys Leu Gly
65                  70                  75                  80
```

```
Gly Phe Asp Val Leu Val Asn Asn Ala Gly Ile Ala Gln Ile Lys Pro
                85                  90                  95

Leu Leu Glu Val Thr Glu Glu Asp Leu Lys Gln Ile Tyr Ser Val Asn
            100                 105                 110

Val Phe Ser Val Phe Phe Gly Ile Gln Ala Ala Ser Arg Lys Phe Asp
        115                 120                 125

Glu Leu Gly Val Lys Gly Lys Ile Ile Asn Ala Ala Ser Ile Ala Ala
    130                 135                 140

Ile Gln Gly Phe Pro Ile Leu Ser Ala Tyr Ser Thr Thr Lys Phe Ala
145                 150                 155                 160

Val Arg Gly Leu Thr Gln Ala Ala Gln Glu Leu Ala Pro Lys Gly
                165                 170                 175

His Thr Val Asn Ala Tyr Ala Pro Gly Ile Val Gly Thr Gly Met Trp
            180                 185                 190

Glu Gln Ile Asp Ala Glu Leu Ser Lys Ile Asn Gly Lys Pro Ile Gly
        195                 200                 205

Glu Asn Phe Lys Glu Tyr Ser Ser Ile Ala Leu Gly Arg Pro Ser
    210                 215                 220

Val Pro Glu Asp Val Ala Gly Leu Val Ser Phe Leu Ala Ser Glu Asn
225                 230                 235                 240

Ser Asn Tyr Val Thr Gly Gln Val Met Leu Val Asp Gly Gly Met Leu
                245                 250                 255

Tyr Asn

<210> SEQ ID NO 35
<211> LENGTH: 318
<212> TYPE: PRT
<213> ORGANISM: Hypocrea jecorina

<400> SEQUENCE: 35

Met Ala Ser Lys Thr Tyr Thr Leu Asn Thr Gly Ala Lys Ile Pro Ala
1               5                   10                  15

Val Gly Phe Gly Thr Phe Ala Asn Glu Gly Ala Lys Gly Glu Thr Tyr
            20                  25                  30

Ala Ala Val Thr Lys Ala Leu Asp Val Gly Tyr Arg His Leu Asp Cys
        35                  40                  45

Ala Trp Phe Tyr His Asn Glu Asp Glu Val Gly Asp Ala Val Arg Asp
    50                  55                  60

Phe Leu Ala Arg Arg Pro Asp Val Lys Arg Glu Asp Leu Phe Ile Cys
65                  70                  75                  80

Thr Lys Val Trp Asn His Leu His Glu Pro Glu Asp Val Lys Trp Ser
                85                  90                  95

Ala Lys Asn Ser Cys Glu Asn Leu Lys Val Asp Tyr Ile Asp Leu Phe
            100                 105                 110

Leu Val His Trp Pro Ile Ala Ala Glu Lys Asn Ser Asp Arg Ser Val
        115                 120                 125

Lys Leu Gly Pro Asp Gly Lys Tyr Val Ile Asn Gln Ala Leu Thr Glu
    130                 135                 140

Asn Pro Glu Pro Thr Trp Arg Ala Met Glu Glu Leu Val Glu Ser Gly
145                 150                 155                 160

Leu Val Lys Ala Ile Gly Val Ser Asn Trp Thr Ile Pro Gly Leu Lys
                165                 170                 175

Lys Leu Leu Gln Ile Ala Lys Ile Lys Pro Ala Val Asn Gln Ile Glu
            180                 185                 190
```

```
Ile His Pro Phe Leu Pro Asn Glu Glu Leu Val Ala Phe Cys Phe Glu
            195                 200                 205

Asn Gly Ile Leu Pro Glu Ala Tyr Ser Pro Leu Gly Ser Gln Asn Gln
        210                 215                 220

Val Pro Ser Thr Gly Glu Arg Val Arg Asp Asn Pro Thr Leu Lys Ala
225                 230                 235                 240

Val Ala Glu Arg Ser Gly Tyr Ser Leu Ala Gln Ile Leu Leu Ala Trp
                245                 250                 255

Gly Leu Lys Arg Gly Tyr Val Val Leu Pro Lys Ser Ser Thr Pro Ser
                260                 265                 270

Arg Ile Glu Ser Asn Phe Asn Ile Pro Glu Leu Ser Asp Glu Asp Phe
            275                 280                 285

Glu Ala Ile Gln Gln Val Ala Lys Gly Arg His Thr Arg Phe Val Asn
        290                 295                 300

Met Lys Asp Thr Phe Gly Tyr Asn Val Trp Pro Glu Glu Glu
305                 310                 315
```

<210> SEQ ID NO 36
<211> LENGTH: 385
<212> TYPE: PRT
<213> ORGANISM: Clostridium butyricum

<400> SEQUENCE: 36

```
Met Arg Met Tyr Asp Tyr Leu Val Pro Ser Val Asn Phe Met Gly Ala
1               5                   10                  15

Asn Ser Val Ser Val Val Gly Glu Arg Cys Lys Ile Leu Gly Gly Lys
            20                  25                  30

Lys Ala Leu Ile Val Thr Asp Lys Phe Leu Lys Asp Met Glu Gly Gly
        35                  40                  45

Ala Val Glu Leu Thr Val Lys Tyr Leu Lys Glu Ala Gly Leu Asp Val
    50                  55                  60

Val Tyr Tyr Asp Gly Val Glu Pro Asn Pro Lys Asp Val Asn Val Ile
65                  70                  75                  80

Glu Gly Leu Lys Ile Phe Lys Glu Glu Asn Cys Asp Met Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Val Asn Pro Leu Pro Pro Ile Val Ala Val Asn Thr Thr Ala Gly Thr
    130                 135                 140

Ala Ser Glu Leu Thr Arg His Cys Val Leu Thr Asn Thr Lys Lys Lys
145                 150                 155                 160

Ile Lys Phe Val Ile Val Ser Trp Arg Asn Leu Pro Leu Val Ser Ile
                165                 170                 175

Asn Asp Pro Met Leu Met Val Lys Lys Pro Ala Gly Leu Thr Ala Ala
            180                 185                 190

Thr Gly Met Asp Ala Leu Thr His Ala Ile Glu Ala Tyr Val Ser Lys
        195                 200                 205

Asp Ala Asn Pro Val Thr Asp Ala Ser Ala Ile Gln Ala Ile Lys Leu
    210                 215                 220

Ile Ser Gln Asn Leu Arg Gln Ala Val Ala Leu Gly Glu Asn Leu Glu
225                 230                 235                 240

Ala Arg Glu Asn Met Ala Tyr Ala Ser Leu Leu Ala Gly Met Ala Phe
                245                 250                 255
```

```
Asn Asn Ala Asn Leu Gly Tyr Val His Ala Met Ala His Gln Leu Gly
            260                 265                 270

Gly Leu Tyr Asp Met Pro His Gly Val Ala Asn Ala Met Leu Leu Pro
        275                 280                 285

His Val Glu Arg Tyr Asn Met Leu Ser Asn Pro Lys Lys Phe Ala Asp
290                 295                 300

Ile Ala Glu Phe Met Gly Glu Asn Ile Ser Gly Leu Ser Val Met Glu
305                 310                 315                 320

Ala Ala Glu Lys Ala Ile Asn Ala Met Phe Arg Leu Ser Glu Asp Val
                325                 330                 335

Gly Ile Pro Lys Ser Leu Lys Glu Met Gly Val Lys Gln Glu Asp Phe
            340                 345                 350

Glu His Met Ala Glu Leu Ala Leu Leu Asp Gly Asn Ala Phe Ser Asn
        355                 360                 365

Pro Arg Lys Gly Asn Ala Lys Asp Ile Ile Asn Ile Phe Lys Ala Ala
    370                 375                 380

Tyr
385

<210> SEQ ID NO 37
<211> LENGTH: 387
<212> TYPE: PRT
<213> ORGANISM: Citrobacter freundii

<400> SEQUENCE: 37

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Lys Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu Thr His Leu Arg Glu Ala Gly Ile
    50                  55                  60

Asp Val Val Val Phe Asp Gly Val Glu Pro Asn Pro Lys Asp Thr Asn
65                  70                  75                  80

Val Arg Asp Gly Leu Glu Val Phe Arg Lys Glu His Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Ser Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Leu Gly Lys Pro Ala Pro Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Ala Ile Gln Ala Ile
    210                 215                 220

Arg Leu Ile Ala Arg Asn Leu Arg Gln Ala Val Ala Leu Gly Ser Asn
```

```
            225                 230                 235                 240
Leu Lys Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Phe Met Gly Glu Asn Thr Asp Gly Leu Ser Thr
305                 310                 315                 320

Met Asp Ala Ala Glu Leu Ala Ile His Ala Ile Ala Arg Leu Ser Ala
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Lys Glu Ile Ala Glu Ile Phe Arg
    370                 375                 380

Gln Ala Phe
385

<210> SEQ ID NO 38
<211> LENGTH: 387
<212> TYPE: PRT
<213> ORGANISM: klebsiella pneumoniae

<400> SEQUENCE: 38

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205
```

```
Ser Lys Asp Ala Asn Pro Val Thr Asp Ala Ala Met Gln Ala Ile
210                 215                 220
Arg Leu Ile Ala Arg Asn Leu Arg Gln Ala Val Ala Leu Gly Ser Asn
225                 230                 235                 240
Leu Gln Ala Arg Glu Asn Met Ala Tyr Ala Ser Leu Leu Ala Gly Met
            245                 250                 255
Ala Phe Asn Asn Ala Asn Leu Gly Tyr Val His Ala Met Ala His Gln
            260                 265                 270
Leu Gly Gly Leu Tyr Asp Met Pro His Gly Val Ala Asn Ala Val Leu
            275                 280                 285
Leu Pro His Val Ala Arg Tyr Asn Leu Ile Ala Asn Pro Glu Lys Phe
290                 295                 300
Ala Asp Ile Ala Glu Leu Met Gly Glu Asn Ile Thr Gly Leu Ser Thr
305                 310                 315                 320
Leu Asp Ala Ala Glu Lys Ala Ile Ala Ile Thr Arg Leu Ser Met
            325                 330                 335
Asp Ile Gly Ile Pro Gln His Leu Arg Asp Leu Gly Val Lys Glu Ala
            340                 345                 350
Asp Phe Pro Tyr Met Ala Glu Met Ala Leu Lys Asp Gly Asn Ala Phe
            355                 360                 365
Ser Asn Pro Arg Lys Gly Asn Glu Gln Glu Ile Ala Ala Ile Phe Arg
370                 375                 380
Gln Ala Phe
385

<210> SEQ ID NO 39
<211> LENGTH: 22
<212> TYPE: PRT
<213> ORGANISM: Rhodoccus erythropolis

<400> SEQUENCE: 39

Met Lys Thr Lys Ala Ala Val Leu Phe Glu Thr His Lys Pro Phe Glu
1               5                   10                  15

Ile Val Glu Leu Glu Leu
            20

<210> SEQ ID NO 40
<211> LENGTH: 371
<212> TYPE: PRT
<213> ORGANISM: Amycolatopsis methanolica

<400> SEQUENCE: 40

Met Lys Thr Lys Ala Ala Val Leu His Ser Ala Gly Lys Pro Phe Glu
1               5                   10                  15

Ile Glu Glu Leu Glu Leu Asp Gly Pro Arg Glu Gly Glu Val Leu Ile
            20                  25                  30

Lys Tyr Thr Ala Ala Gly Leu Cys His Ser Asp Leu His Leu Ile Asp
        35                  40                  45

Asn Asp Leu Val Pro Arg Phe Pro Ile Val Gly His Glu Gly Ala
    50                  55                  60

Gly Val Ile Glu Asp Val Gly Pro Gly Val Thr Lys Val Lys Pro Gly
65                  70                  75                  80

Asp His Val Val Cys Ser Phe Ile Pro Asn Cys Gly Thr Cys Arg Tyr
                85                  90                  95

Cys Ala Thr Gly Arg Ser Asn Leu Cys Asp Met Gly Ala Thr Ile Leu
            100                 105                 110
```

Asp Gly Gly Met Pro Asp Gly Ser Phe Arg Phe His Arg Gly Gly Thr
            115                 120                 125

Asp Tyr Gly Ala Met Cys Met Leu Gly Thr Phe Ser Glu Arg Ala Thr
130                 135                 140

Ile Ser Gln His Ser Val Val Lys Val Asp Asp Trp Leu Pro Leu Glu
145                 150                 155                 160

Thr Ala Val Leu Val Gly Cys Gly Val Pro Thr Gly Trp Ala Ser Ala
                165                 170                 175

Asn Tyr Ala Gly Gly Val Arg Ala Gly Asp Thr Cys Val Val Tyr Gly
            180                 185                 190

Ile Gly Gly Ile Gly Ile Asn Ala Val Gln Gly Ala Ala His Ala Gly
        195                 200                 205

Ala Ala Asn Val Ile Ala Val Asp Pro Val Ala Phe Lys Arg Glu Lys
    210                 215                 220

Ala Leu Glu Leu Gly Ala Thr His Ala Phe Ala Ser Ala Asp Glu Ala
225                 230                 235                 240

Ala Ala Lys Val Ala Glu Leu Thr Trp Gly Gln Met Ala Asp Gln Ala
                245                 250                 255

Leu Ile Thr Val Gly Thr Val Val Glu Gln Val Val Thr Asp Ala Phe
            260                 265                 270

Asn Val Ile Gly Lys Gly Gly Thr Val Val Ile Thr Gly Leu Ala Asn
        275                 280                 285

Pro Glu Lys Leu Thr Val His Leu Ser Gly Gly Val Met Thr Leu Phe
    290                 295                 300

Glu Lys Thr Val Lys Gly Thr Leu Phe Gly Ser Ala Asn Pro Gln Tyr
305                 310                 315                 320

Asp Ile Val Arg Leu Leu Arg Leu Tyr Gln Ala Gly His Val Lys Leu
                325                 330                 335

Asp Glu Leu Val Thr Lys Arg Tyr Ser Leu Glu Glu Val Asn Glu Gly
            340                 345                 350

Tyr Gln Asp Leu Arg Asp Gly Lys Asn Ile Arg Gly Val Ile Met His
        355                 360                 365

Ser Ala Asp
    370

<210> SEQ ID NO 41
<211> LENGTH: 382
<212> TYPE: PRT
<213> ORGANISM: Escherichia coli

<400> SEQUENCE: 41

Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
                20                  25                  30

Ala Leu Ile Val Thr Asp Lys Thr Leu Val Gln Cys Gly Val Val Ala
            35                  40                  45

Lys Val Thr Asp Lys Met Asp Ala Ala Gly Leu Ala Trp Ala Ile Tyr
        50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

```
Pro Glu Phe Ala Asp Val Arg Ser Leu Glu Gly Leu Ser Pro Thr Asn
            115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
                180                 185                 190

Gly Val Asp Ala Leu Thr His Ala Ile Glu Gly Tyr Ile Thr Arg Gly
                195                 200                 205

Ala Trp Ala Leu Thr Asp Ala Leu His Ile Lys Ala Ile Glu Ile Ile
            210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
            275                 280                 285

Arg Tyr Asn Ala Asp Phe Thr Gly Glu Lys Tyr Arg Asp Ile Ala Arg
            290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
                340                 345                 350

Ala Gln Ala Ala Leu Asp Asp Val Cys Thr Gly Gly Asn Pro Arg Glu
            355                 360                 365

Ala Thr Leu Glu Asp Ile Val Glu Leu Tyr His Thr Ala Trp
            370                 375                 380

<210> SEQ ID NO 42
<211> LENGTH: 312
<212> TYPE: PRT
<213> ORGANISM: Escherichia coli

<400> SEQUENCE: 42

Met Asp Ile Ile Phe Tyr His Pro Thr Phe Asp Thr Gln Trp Trp Ile
1               5                   10                  15

Glu Ala Leu Arg Lys Ala Ile Pro Gln Ala Arg Val Arg Ala Trp Lys
            20                  25                  30

Ser Gly Asp Asn Asp Ser Ala Asp Tyr Ala Leu Val Trp His Pro Pro
        35                  40                  45

Val Glu Met Leu Ala Gly Arg Asp Leu Lys Ala Val Phe Ala Leu Gly
    50                  55                  60

Ala Gly Val Asp Ser Ile Leu Ser Lys Leu Gln Ala His Pro Glu Met
65                  70                  75                  80

Leu Asn Pro Ser Val Pro Leu Phe Arg Leu Glu Asp Thr Gly Met Gly
                85                  90                  95

Glu Gln Met Gln Glu Tyr Ala Val Ser Gln Val Leu His Trp Phe Arg
```

```
                100                 105                 110
Arg Phe Asp Asp Tyr Arg Ile Gln Gln Asn Ser Ser His Trp Gln Pro
            115                 120                 125

Leu Pro Glu Tyr His Arg Glu Asp Phe Thr Ile Gly Ile Leu Gly Ala
        130                 135                 140

Gly Val Leu Gly Ser Lys Val Ala Gln Ser Leu Gln Thr Trp Arg Phe
145                 150                 155                 160

Pro Leu Arg Cys Trp Ser Arg Thr Arg Lys Ser Trp Pro Gly Val Gln
                165                 170                 175

Ser Phe Ala Gly Arg Glu Glu Leu Ser Ala Phe Leu Ser Gln Cys Arg
            180                 185                 190

Val Leu Ile Asn Leu Leu Pro Asn Thr Pro Glu Thr Val Gly Ile Ile
        195                 200                 205

Asn Gln Gln Leu Leu Glu Lys Leu Pro Asp Gly Ala Tyr Leu Leu Asn
    210                 215                 220

Leu Ala Arg Gly Val His Val Val Glu Asp Asp Leu Leu Ala Ala Leu
225                 230                 235                 240

Asp Ser Gly Lys Val Lys Gly Ala Met Leu Asp Val Phe Asn Arg Glu
                245                 250                 255

Pro Leu Pro Pro Glu Ser Pro Leu Trp Gln His Pro Arg Val Thr Ile
            260                 265                 270

Thr Pro His Val Ala Ala Ile Thr Arg Pro Ala Glu Ala Val Glu Tyr
        275                 280                 285

Ile Ser Arg Thr Ile Ala Gln Leu Glu Lys Gly Glu Arg Val Cys Gly
    290                 295                 300

Gln Val Asp Arg Ala Arg Gly Tyr
305                 310

<210> SEQ ID NO 43
<211> LENGTH: 324
<212> TYPE: PRT
<213> ORGANISM: Escherichia coli

<400> SEQUENCE: 43

Met Lys Pro Ser Val Ile Leu Tyr Lys Ala Leu Pro Asp Asp Leu Leu
1               5                   10                  15

Gln Arg Leu Gln Glu His Phe Thr Val His Gln Val Ala Asn Leu Ser
            20                  25                  30

Pro Gln Thr Val Glu Gln Asn Ala Ala Ile Phe Ala Glu Ala Glu Gly
        35                  40                  45

Leu Leu Gly Ser Asn Glu Asn Val Asn Ala Ala Leu Leu Glu Lys Met
    50                  55                  60

Pro Lys Leu Arg Ala Thr Ser Thr Ile Ser Val Gly Tyr Asp Asn Phe
65                  70                  75                  80

Asp Val Asp Ala Leu Thr Ala Arg Lys Ile Leu Leu Met His Thr Pro
                85                  90                  95

Thr Val Leu Thr Glu Thr Val Ala Asp Thr Leu Met Ala Leu Val Leu
            100                 105                 110

Ser Thr Ala Arg Arg Val Val Glu Val Ala Glu Arg Val Lys Ala Gly
        115                 120                 125

Glu Trp Thr Ala Ser Ile Gly Pro Asp Trp Tyr Gly Thr Asp Val His
    130                 135                 140

His Lys Thr Leu Gly Ile Val Gly Met Gly Arg Ile Gly Met Ala Leu
145                 150                 155                 160
```

```
Ala Gln Arg Ala His Phe Gly Phe Asn Met Pro Ile Leu Tyr Asn Ala
                165                 170                 175

Arg Arg His His Lys Glu Ala Glu Arg Phe Asn Ala Arg Tyr Cys
            180                 185                 190

Asp Leu Asp Thr Leu Leu Gln Glu Ser Asp Phe Val Cys Leu Ile Leu
                195                 200                 205

Pro Leu Thr Asp Glu Thr His His Leu Phe Gly Ala Glu Gln Phe Ala
                210                 215                 220

Lys Met Lys Ser Ser Ala Ile Phe Ile Asn Ala Gly Arg Gly Pro Val
225                 230                 235                 240

Val Asp Glu Asn Ala Leu Ile Ala Ala Leu Gln Lys Gly Glu Ile His
                245                 250                 255

Ala Ala Gly Leu Asp Val Phe Glu Gln Glu Pro Leu Ser Val Asp Ser
                260                 265                 270

Pro Leu Leu Ser Met Ala Asn Val Val Ala Val Pro His Ile Gly Ser
                275                 280                 285

Ala Thr His Glu Thr Arg Tyr Gly Met Ala Ala Cys Ala Val Asp Asn
                290                 295                 300

Leu Ile Asp Ala Leu Gln Gly Lys Val Glu Lys Asn Cys Val Asn Pro
305                 310                 315                 320

His Val Ala Asp

<210> SEQ ID NO 44
<211> LENGTH: 275
<212> TYPE: PRT
<213> ORGANISM: Escherichia coli

<400> SEQUENCE: 44

Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
                20                  25                  30

Ala Ile Gln Lys Ala Leu Glu Val Gly Tyr Arg Ser Ile Asp Thr Ala
            35                  40                  45

Ala Ala Tyr Lys Asn Glu Glu Gly Val Gly Lys Ala Leu Lys Asn Ala
        50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
                100                 105                 110

Ile Asp His Tyr Val Glu Ala Trp Lys Gly Met Ile Glu Leu Gln Lys
            115                 120                 125

Glu Gly Leu Ile Lys Ser Ile Gly Val Cys Asn Phe Gln Ile His His
        130                 135                 140

Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
                180                 185                 190

Gly Lys Gly Val Phe Asp Gln Lys Val Ile Arg Asp Leu Ala Asp Lys
                195                 200                 205
```

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
                260                 265                 270

Phe Gly Gly
        275

<210> SEQ ID NO 45
<211> LENGTH: 267
<212> TYPE: PRT
<213> ORGANISM: Escherichia coli

<400> SEQUENCE: 45

Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
                20                  25                  30

Ile Asp Thr Ala Gln Ile Tyr Asp Asn Glu Ala Ala Val Gly Gln Ala
            35                  40                  45

Ile Ala Glu Ser Gly Val Pro Arg His Glu Leu Tyr Ile Thr Thr Lys
50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
    130                 135                 140

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
    210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
                245                 250                 255

Val Ser Pro Glu Gly Leu Ala Pro Glu Trp Asp
            260                 265

<210> SEQ ID NO 46
<211> LENGTH: 495
<212> TYPE: PRT
<213> ORGANISM: Escherichia coli

<400> SEQUENCE: 46

```
Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
    130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Val Thr Gly Phe Gly
    210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ile Gly Pro Thr Ile Phe
    370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
```

```
                    405                 410                 415
Leu Ala Asn Asp Ser Gln Tyr Gly Leu Gly Ala Ala Val Trp Thr Arg
                420                 425                 430

Asp Leu Ser Arg Ala His Arg Met Ser Arg Arg Leu Lys Ala Gly Ser
            435                 440                 445

Val Phe Val Asn Asn Tyr Asn Asp Gly Asp Met Thr Val Pro Phe Gly
        450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 47
<211> LENGTH: 496
<212> TYPE: PRT
<213> ORGANISM: Klebsiella pneumoniae

<400> SEQUENCE: 47

Met Met Asn Phe Gln His Leu Ala Tyr Trp Gln Glu Lys Ala Lys Asn
1               5                   10                  15

Leu Ala Ile Glu Thr Arg Leu Phe Ile Asn Gly Glu Tyr Cys Ala Ala
            20                  25                  30

Ala Asp Asn Thr Thr Phe Glu Thr Ile Asp Pro Ala Ala Gln Gln Thr
        35                  40                  45

Leu Ala Gln Val Ala Arg Gly Lys Lys Ala Asp Val Glu Arg Ala Val
    50                  55                  60

Lys Ala Ala Arg Gln Ala Phe Asp Asn Gly Asp Trp Ser Gln Ala Ser
65                  70                  75                  80

Pro Ala Gln Arg Lys Ala Ile Leu Thr Arg Phe Ala Asn Leu Met Glu
                85                  90                  95

Ala His Arg Glu Glu Leu Ala Leu Leu Glu Thr Leu Asp Thr Gly Lys
            100                 105                 110

Pro Ile Arg His Ser Leu Arg Asp Asp Ile Pro Gly Ala Ala Arg Ala
        115                 120                 125

Ile Arg Trp Tyr Ala Glu Ala Leu Asp Lys Val Tyr Gly Glu Val Ala
    130                 135                 140

Pro Thr Gly Ser Asn Glu Leu Ala Met Ile Val Arg Glu Pro Ile Gly
145                 150                 155                 160

Val Ile Ala Ala Val Val Pro Trp Asn Phe Pro Leu Leu Leu Ala Cys
                165                 170                 175

Trp Lys Leu Gly Pro Ala Leu Ala Ala Gly Asn Ser Val Ile Leu Lys
            180                 185                 190

Pro Ser Glu Lys Ser Pro Leu Thr Ala Leu Arg Leu Ala Gly Leu Ala
        195                 200                 205

Lys Glu Ala Gly Leu Pro Asp Gly Val Leu Asn Val Val Ser Gly Phe
    210                 215                 220

Gly His Glu Ala Gly Gln Ala Leu Ala Leu His Pro Asp Val Glu Val
225                 230                 235                 240

Ile Thr Phe Thr Gly Ser Thr Arg Thr Gly Lys Gln Leu Leu Lys Asp
                245                 250                 255

Ala Gly Asp Ser Asn Met Lys Arg Val Trp Leu Glu Ala Gly Gly Lys
            260                 265                 270

Ser Ala Asn Ile Val Phe Ala Asp Cys Pro Asp Leu Gln Gln Ala Val
        275                 280                 285
```

-continued

Arg Ala Thr Ala Gly Gly Ile Phe Tyr Asn Gln Gly Gln Val Cys Ile
    290                 295                 300

Ala Gly Thr Arg Leu Leu Leu Glu Glu Ser Ile Ala Asp Glu Phe Leu
305                 310                 315                 320

Ala Arg Leu Lys Ala Glu Ala Gln His Trp Gln Pro Gly Asn Pro Leu
                325                 330                 335

Asp Pro Asp Thr Thr Met Gly Met Leu Ile Asp Asn Thr His Ala Asp
            340                 345                 350

Asn Val His Ser Phe Ile Arg Gly Gly Glu Ser Gln Ser Thr Leu Phe
        355                 360                 365

Leu Asp Gly Arg Lys Asn Pro Trp Pro Ala Ala Val Gly Pro Thr Ile
370                 375                 380

Phe Val Asp Val Asp Pro Ala Ser Thr Leu Ser Arg Glu Glu Ile Phe
385                 390                 395                 400

Gly Pro Val Leu Val Val Thr Arg Phe Lys Ser Glu Glu Glu Ala Leu
                405                 410                 415

Lys Leu Ala Asn Asp Ser Asp Tyr Gly Leu Gly Ala Ala Val Trp Thr
            420                 425                 430

Arg Asp Leu Ser Arg Ala His Arg Met Ser Arg Arg Leu Lys Ala Gly
        435                 440                 445

Ser Val Phe Val Asn Asn Tyr Asn Asp Gly Asp Met Thr Val Pro Phe
450                 455                 460

Gly Gly Tyr Lys Gln Ser Gly Asn Gly Arg Asp Lys Ser Leu His Ala
465                 470                 475                 480

Leu Glu Lys Phe Thr Glu Leu Lys Thr Ile Trp Ile Ala Leu Glu Ser
                485                 490                 495

<210> SEQ ID NO 48
<211> LENGTH: 519
<212> TYPE: PRT
<213> ORGANISM: Saccharomyces cerevisiae

<400> SEQUENCE: 48

Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
            20                  25                  30

Ile Lys Leu Pro Asn Gly Leu Glu Tyr Glu Gln Pro Thr Gly Leu Phe
        35                  40                  45

Ile Asn Asn Lys Phe Val Pro Ser Lys Gln Asn Lys Thr Phe Glu Val
    50                  55                  60

Ile Asn Pro Ser Thr Glu Glu Glu Ile Cys His Ile Tyr Glu Gly Arg
65                  70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
            100                 105                 110

Tyr Arg Leu Ala Glu Leu Ile Glu Gln Asp Lys Asp Val Ile Ala Ser
        115                 120                 125

Ile Glu Thr Leu Asp Asn Gly Lys Ala Ile Ser Ser Ser Arg Gly Asp
    130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
            180                 185                 190

Phe Pro Leu Leu Met Trp Ala Trp Lys Ile Ala Pro Ala Leu Val Thr
        195                 200                 205

Gly Asn Thr Val Val Leu Lys Thr Ala Glu Ser Thr Pro Leu Ser Ala
    210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255

Asn His Pro Lys Ile Lys Val Ala Phe Thr Gly Ser Thr Ala Thr
            260                 265                 270

Gly Arg His Ile Tyr Gln Ser Ala Ala Ala Gly Leu Lys Lys Val Thr
        275                 280                 285

Leu Glu Leu Gly Gly Lys Ser Pro Asn Ile Val Phe Ala Asp Ala Glu
    290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
            340                 345                 350

Val Gly Asp Pro Phe Asp Glu Ser Thr Phe Gln Gly Ala Gln Thr Ser
        355                 360                 365

Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415

Ile Val Lys Glu Glu Ile Phe Gly Pro Val Val Thr Val Thr Lys Phe
            420                 425                 430

Lys Ser Ala Asp Glu Val Ile Asn Met Ala Asn Asp Ser Glu Tyr Gly
        435                 440                 445

Leu Ala Ala Gly Ile His Thr Ser Asn Ile Asn Thr Ala Leu Lys Val
    450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
            500                 505                 510

Val Arg Ala Lys Leu Asp Glu
        515

<210> SEQ ID NO 49
<211> LENGTH: 520
<212> TYPE: PRT
<213> ORGANISM: Saccharomyces cerevisiae

<400> SEQUENCE: 49

Met Leu Ser Arg Thr Arg Ala Ala Ala Pro Asn Ser Arg Ile Phe Thr
1               5                   10                  15

Arg Ser Leu Leu Arg Leu Tyr Ser Gln Ala Pro Leu Arg Val Pro Ile

```
                 20                  25                  30
Thr Leu Pro Asn Gly Phe Thr Tyr Glu Gln Pro Thr Gly Leu Phe Ile
             35                  40                  45

Asn Gly Glu Phe Val Ala Ser Lys Gln Lys Thr Phe Asp Val Ile
 50                  55                  60

Asn Pro Ser Asn Glu Glu Lys Ile Thr Thr Val Tyr Lys Ala Met Glu
 65                  70                  75                  80

Asp Asp Val Asp Glu Ala Val Ala Ala Ala Lys Lys Ala Phe Glu Thr
                 85                  90                  95

Lys Trp Ser Ile Val Glu Pro Glu Val Arg Ala Lys Ala Leu Phe Asn
                100                 105                 110

Leu Ala Asp Leu Val Glu Lys His Gln Glu Thr Leu Ala Ala Ile Glu
            115                 120                 125

Ser Met Asp Asn Gly Lys Ser Leu Phe Cys Ala Arg Gly Asp Val Ala
            130                 135                 140

Leu Val Ser Lys Tyr Leu Arg Ser Cys Gly Gly Trp Ala Asp Lys Ile
145                 150                 155                 160

Tyr Gly Asn Val Ile Asp Thr Gly Lys Asn His Phe Thr Tyr Ser Ile
                165                 170                 175

Lys Glu Pro Leu Gly Val Cys Gly Gln Ile Ile Pro Trp Asn Phe Pro
                180                 185                 190

Leu Leu Met Trp Ser Trp Lys Ile Gly Pro Ala Leu Ala Thr Gly Asn
            195                 200                 205

Thr Val Val Leu Lys Pro Ala Glu Thr Thr Pro Leu Ser Ala Leu Phe
        210                 215                 220

Ala Ser Gln Leu Cys Gln Glu Ala Gly Ile Pro Ala Gly Val Val Asn
225                 230                 235                 240

Ile Leu Pro Gly Ser Gly Arg Val Val Gly Glu Arg Leu Ser Ala His
                245                 250                 255

Pro Asp Val Lys Lys Ile Ala Phe Thr Gly Ser Thr Ala Thr Gly Arg
                260                 265                 270

His Ile Met Lys Val Ala Ala Asp Thr Val Lys Lys Val Thr Leu Glu
            275                 280                 285

Leu Gly Gly Lys Ser Pro Asn Ile Val Phe Ala Asp Ala Asp Leu Asp
        290                 295                 300

Lys Ala Val Lys Asn Ile Ala Phe Gly Ile Phe Tyr Asn Ser Gly Glu
305                 310                 315                 320

Val Cys Cys Ala Gly Ser Arg Ile Tyr Ile Gln Asp Thr Val Tyr Glu
                325                 330                 335

Glu Val Leu Gln Lys Leu Lys Asp Tyr Thr Glu Ser Leu Lys Val Gly
            340                 345                 350

Asp Pro Phe Asp Glu Glu Val Phe Gln Gly Ala Gln Thr Ser Asp Lys
        355                 360                 365

Gln Leu His Lys Ile Leu Asp Tyr Val Asp Val Ala Lys Ser Glu Gly
        370                 375                 380

Ala Arg Leu Val Thr Gly Gly Ala Arg His Gly Ser Lys Gly Tyr Phe
385                 390                 395                 400

Val Lys Pro Thr Val Phe Ala Asp Val Lys Glu Asp Met Arg Ile Val
                405                 410                 415

Lys Glu Glu Val Phe Gly Pro Ile Val Thr Val Ser Lys Phe Ser Thr
            420                 425                 430

Val Asp Glu Val Ile Ala Met Ala Asn Asp Ser Gln Tyr Gly Leu Ala
        435                 440                 445
```

```
Ala Gly Ile His Thr Asn Asp Ile Asn Lys Ala Val Asp Val Ser Lys
    450                 455                 460

Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
                485                 490                 495

Met Gly Glu Ala Ala Leu Ser Asn Tyr Thr Gln Thr Lys Ser Val Arg
            500                 505                 510

Ile Ala Ile Asp Lys Pro Ile Arg
            515                 520

<210> SEQ ID NO 50
<211> LENGTH: 462
<212> TYPE: PRT
<213> ORGANISM: Escherichia coli

<400> SEQUENCE: 50

Met Thr Ile Thr Pro Ala Thr His Ala Ile Ser Ile Asn Pro Ala Thr
1               5                   10                  15

Gly Glu Gln Leu Ser Val Leu Pro Trp Ala Gly Ala Asp Asp Ile Glu
            20                  25                  30

Asn Ala Leu Gln Leu Ala Ala Ala Gly Phe Arg Asp Trp Arg Glu Thr
        35                  40                  45

Asn Ile Asp Tyr Arg Ala Glu Lys Leu Arg Asp Ile Gly Lys Ala Leu
    50                  55                  60

Arg Ala Arg Ser Glu Glu Met Ala Gln Met Ile Thr Arg Glu Met Gly
65                  70                  75                  80

Lys Pro Ile Asn Gln Ala Arg Ala Glu Val Ala Lys Ser Ala Asn Leu
                85                  90                  95

Cys Asp Trp Tyr Ala Glu His Gly Pro Ala Met Leu Lys Ala Glu Pro
            100                 105                 110

Thr Leu Val Glu Asn Gln Gln Ala Val Ile Glu Tyr Arg Pro Leu Gly
        115                 120                 125

Thr Ile Leu Ala Ile Met Pro Trp Asn Phe Pro Leu Trp Gln Val Met
    130                 135                 140

Arg Gly Ala Val Pro Ile Ile Leu Ala Gly Asn Gly Tyr Leu Leu Lys
145                 150                 155                 160

His Ala Pro Asn Val Met Gly Cys Ala Gln Leu Ile Ala Gln Val Phe
                165                 170                 175

Lys Asp Ala Gly Ile Pro Gln Gly Val Tyr Gly Trp Leu Asn Ala Asp
            180                 185                 190

Asn Asp Gly Val Ser Gln Met Ile Lys Asp Ser Arg Ile Ala Ala Val
        195                 200                 205

Thr Val Thr Gly Ser Val Arg Ala Gly Ala Ala Ile Gly Ala Gln Ala
    210                 215                 220

Gly Ala Ala Leu Lys Lys Cys Val Leu Glu Leu Gly Gly Ser Asp Pro
225                 230                 235                 240

Phe Ile Val Leu Asn Asp Ala Asp Leu Glu Leu Ala Val Lys Ala Ala
                245                 250                 255

Val Ala Gly Arg Tyr Gln Asn Thr Gly Gln Val Cys Ala Ala Ala Lys
            260                 265                 270

Arg Phe Ile Ile Glu Glu Gly Ile Ala Ser Ala Phe Thr Glu Arg Phe
        275                 280                 285

Val Ala Ala Ala Ala Ala Leu Lys Met Gly Asp Pro Arg Asp Glu Glu
```

```
            290                 295                 300
Asn Ala Leu Gly Pro Met Ala Arg Phe Asp Leu Arg Asp Glu Leu His
305                 310                 315                 320

His Gln Val Glu Lys Thr Leu Ala Gln Gly Ala Arg Leu Leu Leu Gly
                325                 330                 335

Gly Glu Lys Met Ala Gly Ala Gly Asn Tyr Tyr Pro Pro Thr Val Leu
            340                 345                 350

Ala Asn Val Thr Pro Glu Met Thr Ala Phe Arg Glu Glu Met Phe Gly
        355                 360                 365

Pro Val Ala Ala Ile Thr Ile Ala Lys Asp Ala Glu His Ala Leu Glu
    370                 375                 380

Leu Ala Asn Asp Ser Glu Phe Gly Leu Ser Ala Thr Ile Phe Thr Thr
385                 390                 395                 400

Asp Glu Thr Gln Ala Arg Gln Met Ala Ala Arg Leu Glu Cys Gly Gly
                405                 410                 415

Val Phe Ile Asn Gly Tyr Cys Ala Ser Asp Ala Arg Val Ala Phe Gly
            420                 425                 430

Gly Val Lys Lys Ser Gly Phe Gly Arg Glu Leu Ser His Phe Gly Leu
        435                 440                 445

His Glu Phe Cys Asn Ile Gln Thr Val Trp Lys Asp Arg Ile
    450                 455                 460

<210> SEQ ID NO 51
<211> LENGTH: 482
<212> TYPE: PRT
<213> ORGANISM: Escherichia coli

<400> SEQUENCE: 51

Met Lys Leu Asn Asp Ser Asn Leu Phe Arg Gln Gln Ala Leu Ile Asn
1               5                   10                  15

Gly Glu Trp Leu Asp Ala Asn Asn Gly Glu Ala Ile Asp Val Thr Asn
            20                  25                  30

Pro Ala Asn Gly Asp Lys Leu Gly Ser Val Pro Lys Met Gly Ala Asp
        35                  40                  45

Glu Thr Arg Ala Ala Ile Asp Ala Ala Asn Arg Ala Leu Pro Ala Trp
    50                  55                  60

Arg Ala Leu Thr Ala Lys Glu Arg Ala Thr Ile Leu Arg Asn Trp Phe
65                  70                  75                  80

Asn Leu Met Met Glu His Gln Asp Asp Leu Ala Arg Leu Met Thr Leu
                85                  90                  95

Glu Gln Gly Lys Pro Leu Ala Glu Ala Lys Gly Glu Ile Ser Tyr Ala
            100                 105                 110

Ala Ser Phe Ile Glu Trp Phe Ala Glu Glu Gly Lys Arg Ile Tyr Gly
        115                 120                 125

Asp Thr Ile Pro Gly His Gln Ala Asp Lys Arg Leu Ile Val Ile Lys
    130                 135                 140

Gln Pro Ile Gly Val Thr Ala Ala Ile Thr Pro Trp Asn Phe Pro Ala
145                 150                 155                 160

Ala Met Ile Thr Arg Lys Ala Gly Pro Ala Leu Ala Ala Gly Cys Thr
                165                 170                 175

Met Val Leu Lys Pro Ala Ser Gln Thr Pro Phe Ser Ala Leu Ala Leu
            180                 185                 190

Ala Glu Leu Ala Ile Arg Ala Gly Val Pro Ala Gly Val Phe Asn Val
        195                 200                 205
```

```
Val Thr Gly Ser Ala Gly Ala Val Gly Asn Glu Leu Thr Ser Asn Pro
    210                 215                 220
Leu Val Arg Lys Leu Ser Phe Thr Gly Ser Thr Glu Ile Gly Arg Gln
225                 230                 235                 240
Leu Met Glu Gln Cys Ala Lys Asp Ile Lys Lys Val Ser Leu Glu Leu
                245                 250                 255
Gly Gly Asn Ala Pro Phe Ile Val Phe Asp Asp Ala Asp Leu Asp Lys
                260                 265                 270
Ala Val Glu Gly Ala Leu Ala Ser Lys Phe Arg Asn Ala Gly Gln Thr
                275                 280                 285
Cys Val Cys Ala Asn Arg Leu Tyr Val Gln Asp Gly Val Tyr Asp Arg
            290                 295                 300
Phe Ala Glu Lys Leu Gln Gln Ala Val Ser Lys Leu His Ile Gly Asp
305                 310                 315                 320
Gly Leu Asp Asn Gly Val Thr Ile Gly Pro Leu Ile Asp Glu Lys Ala
                325                 330                 335
Val Ala Lys Val Glu Glu His Ile Ala Asp Ala Leu Glu Lys Gly Ala
                340                 345                 350
Arg Val Val Cys Gly Gly Lys Ala His Glu Arg Gly Gly Asn Phe Phe
            355                 360                 365
Gln Pro Thr Ile Leu Val Asp Val Pro Ala Asn Ala Lys Val Ser Lys
370                 375                 380
Glu Glu Thr Phe Gly Pro Leu Ala Pro Leu Phe Arg Phe Lys Asp Glu
385                 390                 395                 400
Ala Asp Val Ile Ala Gln Ala Asn Asp Thr Glu Phe Gly Leu Ala Ala
                405                 410                 415
Tyr Phe Tyr Ala Arg Asp Leu Ser Arg Val Phe Arg Val Gly Glu Ala
            420                 425                 430
Leu Glu Tyr Gly Ile Val Gly Ile Asn Thr Gly Ile Ile Ser Asn Glu
                435                 440                 445
Val Ala Pro Phe Gly Gly Ile Lys Ala Ser Gly Leu Gly Arg Glu Gly
                450                 455                 460
Ser Lys Tyr Gly Ile Glu Asp Tyr Leu Glu Ile Lys Tyr Met Cys Ile
465                 470                 475                 480
Gly Leu

<210> SEQ ID NO 52
<211> LENGTH: 474
<212> TYPE: PRT
<213> ORGANISM: Escherichia coli

<400> SEQUENCE: 52

Met Gln His Lys Leu Leu Ile Asn Gly Glu Leu Val Ser Gly Glu Gly
1               5                   10                  15
Glu Lys Gln Pro Val Tyr Asn Pro Ala Thr Gly Asp Val Leu Leu Glu
                20                  25                  30
Ile Ala Glu Ala Ser Ala Glu Gln Val Asp Ala Ala Val Arg Ala Ala
            35                  40                  45
Asp Ala Ala Phe Ala Glu Trp Gly Gln Thr Thr Pro Lys Val Arg Ala
        50                  55                  60
Glu Cys Leu Leu Lys Leu Ala Asp Val Ile Glu Glu Asn Gly Gln Val
65                  70                  75                  80
Phe Ala Glu Leu Glu Ser Arg Asn Cys Gly Lys Pro Leu His Ser Ala
                85                  90                  95
```

```
Phe Asn Asp Glu Ile Pro Ala Ile Val Asp Val Phe Arg Phe Phe Ala
                100                 105                 110

Gly Ala Ala Arg Cys Leu Asn Gly Leu Ala Ala Gly Glu Tyr Leu Glu
            115                 120                 125

Gly His Thr Ser Met Ile Arg Arg Asp Pro Leu Gly Val Val Ala Ser
        130                 135                 140

Ile Ala Pro Trp Asn Tyr Pro Leu Met Met Ala Ala Trp Lys Leu Ala
145                 150                 155                 160

Pro Ala Leu Ala Ala Gly Asn Cys Val Val Leu Lys Pro Ser Glu Ile
                165                 170                 175

Thr Pro Leu Thr Ala Leu Lys Leu Ala Glu Leu Ala Lys Asp Ile Phe
            180                 185                 190

Pro Ala Gly Val Ile Asn Ile Leu Phe Gly Arg Gly Lys Thr Val Gly
        195                 200                 205

Asp Pro Leu Thr Gly His Pro Lys Val Arg Met Val Ser Leu Thr Gly
210                 215                 220

Ser Ile Ala Thr Gly Glu His Ile Ile Ser His Thr Ala Ser Ser Ile
225                 230                 235                 240

Lys Arg Thr His Met Glu Leu Gly Gly Lys Ala Pro Val Ile Val Phe
                245                 250                 255

Asp Asp Ala Asp Ile Glu Ala Val Val Glu Gly Val Arg Thr Phe Gly
            260                 265                 270

Tyr Tyr Asn Ala Gly Gln Asp Cys Thr Ala Ala Cys Arg Ile Tyr Ala
        275                 280                 285

Gln Lys Gly Ile Tyr Asp Thr Leu Val Glu Lys Leu Gly Ala Ala Val
    290                 295                 300

Ala Thr Leu Lys Ser Gly Ala Pro Asp Asp Glu Ser Thr Glu Leu Gly
305                 310                 315                 320

Pro Leu Ser Ser Leu Ala His Leu Glu Arg Val Gly Lys Ala Val Glu
                325                 330                 335

Glu Ala Lys Ala Thr Gly His Ile Lys Val Ile Thr Gly Gly Glu Lys
            340                 345                 350

Arg Lys Gly Asn Gly Tyr Tyr Tyr Ala Pro Thr Leu Leu Ala Gly Ala
        355                 360                 365

Leu Gln Asp Asp Ala Ile Val Gln Lys Glu Val Phe Gly Pro Val Val
370                 375                 380

Ser Val Thr Pro Phe Asp Asn Glu Glu Gln Val Val Asn Trp Ala Asn
385                 390                 395                 400

Asp Ser Gln Tyr Gly Leu Ala Ser Ser Val Trp Thr Lys Asp Val Gly
                405                 410                 415

Arg Ala His Arg Val Ser Ala Arg Leu Gln Tyr Gly Cys Thr Trp Val
            420                 425                 430

Asn Thr His Phe Met Leu Val Ser Glu Met Pro His Gly Gly Gln Lys
        435                 440                 445

Leu Ser Gly Tyr Gly Lys Asp Met Ser Leu Tyr Gly Leu Glu Asp Tyr
    450                 455                 460

Thr Val Val Arg His Val Met Val Lys His
465                 470

<210> SEQ ID NO 53
<211> LENGTH: 480
<212> TYPE: PRT
<213> ORGANISM: Pseudomonas putida

<400> SEQUENCE: 53
```

-continued

```
Met Gln Leu Lys Asp Ala Gln Leu Phe Arg Gln Ala Tyr Ile Asn
1               5                   10                  15

Gly Glu Trp Leu Asp Ala Asp Asn Gly Gln Thr Ile Lys Val Thr Asn
                20                  25                  30

Pro Ala Thr Gly Glu Val Ile Gly Thr Val Pro Lys Met Gly Thr Ala
            35                  40                  45

Glu Thr Arg Arg Ala Ile Glu Ala Ala Asp Lys Ala Leu Pro Ala Trp
50                      55                      60

Arg Ala Leu Thr Ala Lys Glu Arg Ser Ala Lys Leu Arg Arg Trp Phe
65                  70                  75                  80

Glu Leu Met Ile Glu Asn Gln Asp Asp Leu Ala Arg Leu Met Thr Thr
                85                  90                      95

Glu Gln Gly Lys Pro Leu Ala Glu Ala Lys Gly Glu Ile Ala Tyr Ala
                100                 105                 110

Ala Ser Phe Ile Glu Trp Phe Ala Glu Glu Ala Lys Arg Ile Tyr Gly
        115                 120                 125

Asp Thr Ile Pro Gly His Gln Pro Asp Lys Arg Leu Ile Val Ile Lys
        130                 135                 140

Gln Pro Ile Gly Val Thr Ala Ala Ile Thr Pro Trp Asn Phe Pro Ala
145                 150                 155                 160

Ala Met Ile Thr Arg Lys Ala Gly Pro Ala Leu Ala Ala Gly Cys Thr
                165                 170                 175

Met Val Leu Lys Pro Ala Ser Gln Thr Pro Tyr Ser Ala Leu Ala Leu
                180                 185                 190

Val Glu Leu Ala His Arg Ala Gly Ile Pro Ala Gly Val Leu Ser Val
            195                 200                 205

Val Thr Gly Ser Ala Gly Glu Val Gly Gly Glu Leu Thr Gly Asn Ser
210                 215                 220

Leu Val Arg Lys Leu Ser Phe Thr Gly Ser Thr Glu Ile Gly Arg Gln
225                 230                 235                 240

Leu Met Glu Glu Cys Ala Lys Asp Ile Lys Lys Val Ser Leu Glu Leu
                245                 250                 255

Gly Gly Asn Ala Pro Phe Ile Val Phe Asp Asp Ala Asp Leu Asp Lys
                260                 265                 270

Ala Val Glu Gly Ala Ile Ile Ser Lys Tyr Arg Asn Asn Gly Gln Thr
            275                 280                 285

Cys Val Cys Ala Asn Arg Ile Tyr Val Gln Asp Gly Val Tyr Asp Ala
        290                 295                 300

Phe Ala Glu Lys Leu Ala Ala Val Ala Lys Leu Lys Ile Gly Asn
305                 310                 315                 320

Gly Leu Glu Glu Gly Thr Thr Thr Gly Pro Leu Ile Asp Gly Lys Ala
                325                 330                 335

Val Ala Lys Val Gln Glu His Ile Glu Asp Ala Val Ser Lys Gly Ala
            340                 345                 350

Lys Val Leu Ser Gly Gly Lys Leu Ile Glu Gly Asn Phe Phe Glu Pro
            355                 360                 365

Thr Ile Leu Val Asp Val Pro Lys Thr Ala Ala Val Ala Lys Glu Glu
        370                 375                 380

Thr Phe Gly Pro Leu Ala Pro Leu Phe Arg Phe Lys Asp Glu Ala Glu
385                 390                 395                 400

Val Ile Ala Met Ser Asn Asp Thr Glu Phe Gly Leu Ala Ser Tyr Phe
                405                 410                 415
```

Tyr Ala Arg Asp Met Ser Arg Val Phe Arg Val Ala Glu Ala Leu Glu
                420                 425                 430

Tyr Gly Met Val Gly Ile Asn Thr Gly Leu Ile Ser Asn Glu Val Ala
            435                 440                 445

Pro Phe Gly Gly Ile Lys Ala Ser Gly Leu Gly Arg Glu Gly Ser Lys
        450                 455                 460

Tyr Gly Ile Glu Asp Tyr Leu Glu Ile Lys Tyr Leu Cys Ile Ser Val
465                 470                 475                 480

<210> SEQ ID NO 54
<211> LENGTH: 479
<212> TYPE: PRT
<213> ORGANISM: Escherichia coli

<400> SEQUENCE: 54

Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
    210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
    290                 295                 300

Leu Gly Glu Ala Met Gln Ala Val Gln Phe Gly Asn Pro Ala Glu Arg
305                 310                 315                 320

```
Asn Asp Ile Ala Met Gly Pro Leu Ile Asn Ala Ala Ala Leu Glu Arg
                325                 330                 335

Val Glu Gln Lys Val Ala Arg Ala Val Glu Gly Ala Arg Val Ala
            340                 345                 350

Phe Gly Gly Lys Ala Val Glu Gly Lys Gly Tyr Tyr Tyr Pro Pro Thr
            355                 360                 365

Leu Leu Leu Asp Val Arg Gln Glu Met Ser Ile Met His Glu Glu Thr
            370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
                420                 425                 430

Gly Glu Thr Tyr Ile Asn Arg Glu Asn Phe Glu Ala Met Gln Gly Phe
            435                 440                 445

His Ala Gly Trp Arg Lys Ser Gly Ile Gly Gly Ala Asp Gly Lys His
        450                 455                 460

Gly Leu His Glu Tyr Leu Gln Thr Gln Val Val Tyr Leu Gln Ser
465                 470                 475
```

<210> SEQ ID NO 55
<211> LENGTH: 512
<212> TYPE: PRT
<213> ORGANISM: Escherichia coli

<400> SEQUENCE: 55

```
Met Thr Asn Asn Pro Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
            20                  25                  30

Trp Val Ala Pro Ala Asp Gly Glu Tyr Tyr Gln Asn Leu Thr Pro Val
        35                  40                  45

Thr Gly Gln Leu Leu Cys Glu Val Ala Ser Ser Gly Lys Arg Asp Ile
50                  55                  60

Asp Leu Ala Leu Asp Ala Ala His Lys Val Lys Asp Lys Trp Ala His
65                  70                  75                  80

Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
```

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
                260                 265                 270

Ser Pro Asn Ile Phe Phe Ala Asp Val Met Asp Glu Glu Asp Ala Phe
            275                 280                 285

Phe Asp Lys Ala Leu Glu Gly Phe Ala Leu Phe Ala Phe Asn Gln Gly
        290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
                340                 345                 350

Gly Gln Leu Glu Thr Ile Leu Asn Tyr Ile Asp Ile Gly Lys Lys Glu
            355                 360                 365

Gly Ala Asp Val Leu Thr Gly Gly Arg Arg Lys Leu Leu Glu Gly Glu
        370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Glu Ala Leu Glu Leu Ala Asn Asp Thr
                420                 425                 430

Gln Tyr Gly Leu Gly Ala Gly Val Trp Ser Arg Asn Gly Asn Leu Ala
            435                 440                 445

Tyr Lys Met Gly Arg Gly Ile Gln Ala Gly Arg Val Trp Thr Asn Cys
        450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
                500                 505                 510

<210> SEQ ID NO 56
<211> LENGTH: 463
<212> TYPE: PRT
<213> ORGANISM: Methanocaldococcus jannaschii

<400> SEQUENCE: 56

Met Phe Ile Asp Gly Lys Trp Ile Asn Arg Glu Asp Met Asp Val Ile
1               5                   10                  15

Asn Pro Tyr Ser Leu Glu Val Ile Lys Lys Ile Pro Ala Leu Ser Arg
                20                  25                  30

Glu Glu Ala Lys Glu Ala Ile Asp Thr Ala Lys Tyr Lys Glu Val
            35                  40                  45

Met Lys Asn Leu Pro Ile Thr Lys Arg Tyr Asn Ile Leu Met Asn Ile
        50                  55                  60

Ala Lys Gln Ile Lys Glu Lys Lys Glu Glu Leu Ala Lys Ile Leu Ala
65                  70                  75                  80

Ile Asp Ala Gly Lys Pro Ile Lys Gln Ala Arg Val Glu Val Glu Arg
                85                  90                  95

Ser Ile Gly Thr Phe Lys Leu Ala Ala Phe Tyr Val Lys Glu His Arg
            100                 105                 110

Asp Glu Val Ile Pro Ser Asp Arg Leu Ile Phe Thr Arg Arg Glu
            115                 120                 125

Pro Val Gly Ile Val Gly Ala Ile Thr Pro Phe Asn Phe Pro Leu Asn
            130                 135                 140

Leu Ser Ala His Lys Ile Ala Pro Ala Ile Ala Thr Gly Asn Val Ile
145                 150                 155                 160

Val His His Pro Ser Ser Lys Ala Pro Leu Val Cys Ile Glu Leu Ala
                165                 170                 175

Lys Ile Ile Glu Asn Ala Leu Lys Lys Tyr Asn Val Pro Leu Gly Val
                180                 185                 190

Tyr Asn Leu Leu Thr Gly Ala Gly Glu Val Val Gly Asp Glu Ile Val
            195                 200                 205

Val Asn Glu Lys Val Asn Met Ile Ser Phe Thr Gly Ser Ser Lys Val
            210                 215                 220

Gly Glu Leu Ile Thr Lys Lys Ala Gly Phe Lys Lys Ile Ala Leu Glu
225                 230                 235                 240

Leu Gly Gly Val Asn Pro Asn Ile Val Leu Lys Asp Ala Asp Leu Asn
                245                 250                 255

Lys Ala Val Asn Ala Leu Ile Lys Gly Ser Phe Ile Tyr Ala Gly Gln
                260                 265                 270

Val Cys Ile Ser Val Gly Met Ile Leu Val Asp Glu Ser Ile Ala Asp
            275                 280                 285

Lys Phe Ile Glu Met Phe Val Asn Lys Ala Lys Val Leu Asn Val Gly
            290                 295                 300

Asn Pro Leu Asp Glu Lys Thr Asp Val Gly Pro Leu Ile Ser Val Glu
305                 310                 315                 320

His Ala Glu Trp Val Lys Val Val Lys Ala Ile Asp Glu Gly
                325                 330                 335

Gly Lys Leu Leu Leu Gly Gly Lys Arg Asp Lys Ala Leu Phe Tyr Pro
            340                 345                 350

Thr Ile Leu Glu Val Asp Arg Asp Asn Ile Leu Cys Lys Thr Glu Thr
            355                 360                 365

Phe Ala Pro Val Ile Pro Ile Ile Arg Thr Asn Glu Glu Met Ile
370                 375                 380

Asp Ile Ala Asn Ser Thr Glu Tyr Gly Leu His Ser Ala Ile Phe Thr
385                 390                 395                 400

Asn Asp Ile Asn Lys Ser Leu Lys Phe Ala Glu Asn Leu Glu Phe Gly
                405                 410                 415

Gly Val Val Ile Asn Asp Ser Ser Leu Phe Arg Gln Asp Asn Met Pro
            420                 425                 430

Phe Gly Gly Val Lys Lys Ser Gly Leu Gly Arg Glu Gly Val Lys Tyr
            435                 440                 445

Ala Met Glu Glu Met Ser Asn Ile Lys Thr Ile Ile Ser Lys
450                 455                 460

<210> SEQ ID NO 57
<211> LENGTH: 488
<212> TYPE: PRT
<213> ORGANISM: Bacillus licheniformis

<400> SEQUENCE: 57

```
Met Ser Val Ala Ala Glu Ser Lys Thr Tyr Phe Asn Phe Ile Asn Gly
1               5                   10                  15

Arg Trp Val Lys Ala Glu Ser Gly Gly Met Glu Gln Ser Leu Asn Pro
                20                  25                  30

Ala Asp Thr Arg Asp Ile Val Gly Leu Val Gln Lys Ser Ser Ile Glu
            35                  40                  45

Asp Val Asp Arg Ala Val Glu Ala Ala Lys Gln Ala Lys Lys Ala Trp
50                  55                  60

Arg Lys Leu Ser Gly Ala Glu Arg Gly Gln Phe Leu Tyr Lys Ala Ala
65                  70                  75                  80

Asp Ile Met Glu Gln Arg Leu Asp Glu Ile Ala Glu Cys Ala Thr Arg
                85                  90                  95

Glu Met Gly Lys Thr Leu Pro Glu Ala Lys Gly Glu Thr Ala Arg Gly
                100                 105                 110

Ile Ala Ile Leu Arg Tyr Tyr Ala Gly Glu Gly Leu Arg Lys Thr Gly
            115                 120                 125

Asp Val Ile Pro Ser Thr Asp Ser Ser Ala Phe Met Tyr Thr Asp Arg
        130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Ile Tyr Gly Asn Thr
                165                 170                 175

Val Val Ile Lys Pro Ala Thr Glu Thr Ala Val Thr Cys Leu Lys Val
                180                 185                 190

Ile Ser Cys Phe Glu Glu Ala Gly Ile Pro Ser Gly Val Val Asn Ala
            195                 200                 205

Val Thr Gly Pro Gly Ser Ser Ala Gly Gln Arg Leu Ala Glu His Pro
210                 215                 220

Asp Val Asn Gly Ile Thr Phe Thr Gly Ser Asn Gln Thr Gly Lys Ile
225                 230                 235                 240

Ile Gly Arg Thr Ala Phe Glu Arg Gly Ala Lys Tyr Gln Leu Glu Met
            245                 250                 255

Gly Gly Lys Asn Pro Val Ile Val Ala Asp Asp Ala Asp Leu Asp Ile
        260                 265                 270

Ala Val Glu Ala Val Ile Ser Gly Ala Phe Arg Ser Thr Gly Gln Lys
    275                 280                 285

Cys Thr Ala Thr Ser Arg Val Ile Val Leu Asn Gly Val Tyr Asp Arg
290                 295                 300

Phe Lys Glu Lys Leu Leu Gln Gln Thr Lys Glu Ile Thr Ile Gly Asp
305                 310                 315                 320

Ser Leu Lys Glu Asp Val Trp Met Gly Pro Ile Ala Asn Lys Gln Gln
                325                 330                 335

Leu Asp Asn Cys Leu Ser Tyr Ile Ala Lys Gly Lys Gln Glu Gly Ala
            340                 345                 350

Asp Leu Ile Phe Gly Gly Glu Arg Leu Ala Asp Gly Lys Tyr Glu Asn
        355                 360                 365

Gly Tyr Tyr Ile Arg Pro Ala Ile Phe Asp Asn Val Thr Ser Gly Met
    370                 375                 380

Thr Ile Ala Gln Glu Glu Ile Phe Gly Pro Val Ile Ala Leu Ile Lys
385                 390                 395                 400

Ala Asp Thr Leu Glu Glu Ala Leu Glu Thr Ala Asn Asp Val Lys Phe
                405                 410                 415
```

```
Gly Leu Ser Ala Ser Ile Phe Thr Gln Asn Ile Arg Arg Met Leu Ser
            420                 425                 430

Phe Thr Asp Glu Ile Glu Ala Gly Leu Ile Arg Val Asn Ala Glu Ser
        435                 440                 445

Ala Gly Val Glu Leu Gln Ala Pro Phe Gly Gly Val Lys Gln Ser Ser
    450                 455                 460

Ser His Ser Arg Glu Gln Gly Glu Ala Ala Lys Glu Phe Phe Thr Ala
465                 470                 475                 480

Val Lys Thr Val Phe Val Lys Pro
                485

<210> SEQ ID NO 58
<211> LENGTH: 491
<212> TYPE: PRT
<213> ORGANISM: Pseudomonas sp.

<400> SEQUENCE: 58

Met Lys Gln Tyr Arg Asn Phe Val Asp Gly Lys Trp Val Glu Ser Ser
1               5                   10                  15

Lys Thr Phe Gln Asp Val Thr Pro Ile Asp Gly Ser Val Val Ala Val
            20                  25                  30

Val His Glu Ala Asp Arg Asp Leu Val Asp Ala Ala Val Lys Ala Gly
        35                  40                  45

His Arg Ala Leu Glu Gly Glu Trp Gly Arg Thr Thr Ala Ala Gln Arg
    50                  55                  60

Val Asp Trp Leu Arg Arg Ile Ala Asn Glu Met Glu Arg Arg Gln Gln
65                  70                  75                  80

Asp Phe Leu Asp Ala Glu Met Ala Asp Thr Gly Lys Pro Leu Ser Met
                85                  90                  95

Ala Ala Thr Ile Asp Ile Pro Arg Gly Ile Ala Asn Phe Arg Asn Phe
            100                 105                 110

Ala Asp Ile Leu Ala Thr Ala Pro Val Asp Ser His Arg Leu Asp Leu
        115                 120                 125

Pro Asp Gly Ala Tyr Ala Leu Asn Tyr Ala Ala Arg Lys Pro Leu Gly
    130                 135                 140

Val Val Gly Val Ile Ser Pro Trp Asn Leu Pro Leu Leu Leu Leu Thr
145                 150                 155                 160

Trp Lys Val Ala Pro Ala Leu Ala Cys Gly Asn Ala Val Val Val Lys
                165                 170                 175

Pro Ser Glu Asp Thr Pro Gly Thr Ala Thr Leu Leu Ala Glu Val Met
            180                 185                 190

Glu Ala Val Gly Ile Pro Pro Gly Val Phe Asn Leu Val His Gly Phe
        195                 200                 205

Gly Pro Asn Ser Ala Gly Glu Phe Ile Ser Gln His Pro Asp Ile Ser
    210                 215                 220

Ala Ile Thr Phe Thr Gly Glu Ser Lys Thr Gly Ser Thr Ile Met Arg
225                 230                 235                 240

Ala Ala Ala Glu Gly Val Lys Pro Val Ser Phe Glu Leu Gly Gly Lys
                245                 250                 255

Asn Ala Ala Val Ile Phe Ala Asp Cys Asp Phe Glu Lys Met Leu Asp
            260                 265                 270

Gly Met Met Arg Ala Leu Phe Leu Asn Ser Gly Gln Val Cys Leu Cys
        275                 280                 285

Ser Glu Arg Val Tyr Val Glu Arg Pro Ile Phe Asp Arg Phe Cys Val
    290                 295                 300
```

```
Ala Leu Ala Glu Arg Ile Lys Ala Leu Lys Val Asp Trp Pro His Glu
305                 310                 315                 320

Thr Asp Thr Gln Met Gly Pro Leu Ile Ser Ser Lys His Arg Asp Lys
            325                 330                 335

Val Leu Ser Tyr Phe Glu Leu Ala Arg Gln Glu Gly Ala Thr Phe Leu
        340                 345                 350

Ala Gly Gly Gly Val Pro Arg Phe Gly Asp Glu Arg Asp Asn Gly Ala
    355                 360                 365

Trp Val Glu Pro Thr Val Ile Ala Gly Leu Ser Asp Asp Ala Arg Val
370                 375                 380

Val Arg Glu Glu Ile Phe Gly Pro Ile Cys His Val Thr Pro Phe Asp
385                 390                 395                 400

Ser Glu Ser Glu Val Ile Arg Arg Ala Asn Asp Thr Arg Tyr Gly Leu
                405                 410                 415

Ala Ala Thr Ile Trp Thr Thr Asn Leu Ser Arg Ala His Arg Val Ser
            420                 425                 430

Glu Leu Met Arg Val Gly Ile Ser Trp Val Asn Thr Trp Phe Leu Arg
        435                 440                 445

Asp Leu Arg Thr Pro Phe Gly Gly Ala Gly Leu Ser Gly Ile Gly Arg
    450                 455                 460

Glu Gly Gly Met His Ser Leu Asn Phe Tyr Ser Glu Leu Thr Asn Val
465                 470                 475                 480

Cys Val Arg Ile Asp Lys Glu Ser Pro Asp Val
                485                 490

<210> SEQ ID NO 59
<211> LENGTH: 499
<212> TYPE: PRT
<213> ORGANISM: Escherichia coli

<400> SEQUENCE: 59

Met Thr Glu Pro His Val Ala Val Leu Ser Gln Val Gln Gln Phe Leu
1               5                   10                  15

Asp Arg Gln His Gly Leu Tyr Ile Asp Gly Arg Pro Gly Pro Ala Gln
            20                  25                  30

Ser Glu Lys Arg Leu Ala Ile Phe Asp Pro Ala Thr Gly Gln Glu Ile
        35                  40                  45

Ala Ser Thr Ala Asp Ala Asn Glu Ala Asp Val Asp Asn Ala Val Met
    50                  55                  60

Ser Ala Trp Arg Ala Phe Val Ser Arg Arg Trp Ala Gly Arg Leu Pro
65                  70                  75                  80

Ala Glu Arg Glu Arg Ile Leu Leu Arg Phe Ala Asp Leu Val Glu Gln
                85                  90                  95

His Ser Glu Glu Leu Ala Gln Leu Glu Thr Leu Glu Gln Gly Lys Ser
            100                 105                 110

Ile Ala Ile Ser Arg Ala Phe Glu Val Gly Cys Thr Leu Asn Trp Met
        115                 120                 125

Arg Tyr Thr Ala Gly Leu Thr Thr Lys Ile Ala Gly Lys Thr Leu Asp
    130                 135                 140

Leu Ser Ile Pro Leu Pro Gln Gly Ala Arg Tyr Gln Ala Trp Thr Arg
145                 150                 155                 160

Lys Glu Pro Val Gly Val Val Ala Gly Ile Val Pro Trp Asn Phe Pro
                165                 170                 175

Leu Met Ile Gly Met Trp Lys Val Met Pro Ala Leu Ala Ala Gly Cys
```

```
            180                 185                 190
Ser Ile Val Ile Lys Pro Ser Glu Thr Thr Pro Leu Thr Met Leu Arg
        195                 200                 205

Val Ala Glu Leu Ala Ser Glu Ala Gly Ile Pro Asp Gly Val Phe Asn
    210                 215                 220

Val Val Thr Gly Ser Gly Ala Val Cys Gly Ala Ala Leu Thr Ser His
225                 230                 235                 240

Pro His Val Ala Lys Ile Ser Phe Thr Gly Ser Thr Ala Thr Gly Lys
            245                 250                 255

Gly Ile Ala Arg Thr Ala Ala Asp His Leu Thr Arg Val Thr Leu Glu
        260                 265                 270

Leu Gly Gly Lys Asn Pro Ala Ile Val Leu Lys Asp Ala Asp Pro Gln
    275                 280                 285

Trp Val Ile Glu Gly Leu Met Thr Gly Ser Phe Leu Asn Gln Gly Gln
    290                 295                 300

Val Cys Ala Ala Ser Ser Arg Ile Tyr Ile Glu Ala Pro Leu Phe Asp
305                 310                 315                 320

Thr Leu Val Ser Gly Phe Glu Gln Ala Val Lys Ser Leu Gln Val Gly
            325                 330                 335

Pro Gly Met Ser Pro Val Ala Gln Ile Asn Pro Leu Val Ser Arg Ala
        340                 345                 350

His Cys Asp Lys Val Cys Ser Phe Leu Asp Asp Ala Gln Ala Gln Gln
    355                 360                 365

Ala Glu Leu Ile Arg Gly Ser Asn Gly Pro Ala Gly Glu Gly Tyr Tyr
    370                 375                 380

Val Ala Pro Thr Leu Val Val Asn Pro Asp Ala Lys Leu Arg Leu Thr
385                 390                 395                 400

Arg Glu Glu Val Phe Gly Pro Val Val Asn Leu Val Arg Val Ala Asp
            405                 410                 415

Gly Glu Glu Ala Leu Gln Leu Ala Asn Asp Thr Glu Tyr Gly Leu Thr
        420                 425                 430

Ala Ser Val Trp Thr Gln Asn Leu Ser Gln Ala Leu Glu Tyr Ser Asp
    435                 440                 445

Arg Leu Gln Ala Gly Thr Val Trp Val Asn Ser His Thr Leu Ile Asp
    450                 455                 460

Ala Asn Leu Pro Phe Gly Gly Met Lys Gln Ser Gly Thr Gly Arg Asp
465                 470                 475                 480

Phe Gly Pro Asp Trp Leu Asp Gly Trp Cys Glu Thr Lys Ser Val Cys
            485                 490                 495

Val Arg Tyr

<210> SEQ ID NO 60
<211> LENGTH: 492
<212> TYPE: PRT
<213> ORGANISM: Escherichia coli

<400> SEQUENCE: 60

Met Thr Leu Trp Ile Asn Gly Asp Trp Ile Thr Gly Gln Gly Ala Ser
1               5                   10                  15

Arg Val Lys Arg Asn Pro Val Ser Gly Glu Val Leu Trp Gln Gly Asn
            20                  25                  30

Asp Ala Asp Ala Ala Gln Val Glu Gln Ala Cys Arg Ala Ala Arg Ala
        35                  40                  45

Ala Phe Pro Arg Trp Ala Arg Leu Ser Phe Ala Glu Arg His Ala Val
```

```
           50                  55                  60
Val Glu Arg Phe Ala Ala Leu Leu Glu Ser Asn Lys Ala Glu Leu Thr
 65                  70                  75                  80

Ala Ile Ile Ala Arg Glu Thr Gly Lys Pro Arg Trp Glu Ala Ala Thr
                 85                  90                  95

Glu Val Thr Ala Met Ile Asn Lys Ile Ala Ile Ser Ile Lys Ala Tyr
                100                 105                 110

His Val Arg Thr Gly Glu Gln Arg Ser Glu Met Pro Asp Gly Ala Ala
                115                 120                 125

Ser Leu Arg His Arg Pro His Gly Val Leu Ala Val Phe Gly Pro Tyr
            130                 135                 140

Asn Phe Pro Gly His Leu Pro Asn Gly His Ile Val Pro Ala Leu Leu
145                 150                 155                 160

Ala Gly Asn Thr Ile Ile Phe Lys Pro Ser Glu Leu Thr Pro Trp Ser
                165                 170                 175

Gly Glu Ala Val Met Arg Leu Trp Gln Gln Ala Gly Leu Pro Pro Gly
                180                 185                 190

Val Leu Asn Leu Val Gln Gly Gly Arg Glu Thr Gly Gln Ala Leu Ser
            195                 200                 205

Ala Leu Glu Asp Leu Asp Gly Leu Leu Phe Thr Gly Ser Ala Asn Thr
            210                 215                 220

Gly Tyr Gln Leu His Arg Gln Leu Ser Gly Gln Pro Glu Lys Ile Leu
225                 230                 235                 240

Ala Leu Glu Met Gly Gly Asn Asn Pro Leu Ile Ile Asp Glu Val Ala
                245                 250                 255

Asp Ile Asp Ala Ala Val His Leu Thr Ile Gln Ser Ala Phe Val Thr
                260                 265                 270

Ala Gly Gln Arg Cys Thr Cys Ala Arg Arg Leu Leu Leu Lys Ser Gly
            275                 280                 285

Ala Gln Gly Asp Ala Phe Leu Ala Arg Leu Val Ala Val Ser Gln Arg
            290                 295                 300

Leu Thr Pro Gly Asn Trp Asp Asp Glu Pro Gln Pro Phe Ile Gly Gly
305                 310                 315                 320

Leu Ile Ser Glu Gln Ala Ala Gln Gln Val Val Thr Ala Trp Gln Gln
                325                 330                 335

Leu Glu Ala Met Gly Gly Arg Pro Leu Leu Ala Pro Arg Leu Leu Gln
                340                 345                 350

Ala Gly Thr Ser Leu Leu Thr Pro Gly Ile Ile Glu Met Thr Gly Val
            355                 360                 365

Ala Gly Val Pro Asp Glu Glu Val Phe Gly Pro Leu Leu Arg Val Trp
            370                 375                 380

Arg Tyr Asp Thr Phe Asp Glu Ala Ile Arg Met Ala Asn Asn Thr Arg
385                 390                 395                 400

Phe Gly Leu Ser Cys Gly Leu Val Ser Pro Glu Arg Glu Lys Phe Asp
                405                 410                 415

Gln Leu Leu Leu Glu Ala Arg Ala Gly Ile Val Asn Trp Asn Lys Pro
                420                 425                 430

Leu Thr Gly Ala Ala Ser Thr Ala Pro Phe Gly Gly Ile Gly Ala Ser
            435                 440                 445

Gly Asn His Arg Pro Ser Ala Trp Tyr Ala Ala Asp Tyr Cys Ala Trp
            450                 455                 460

Pro Met Ala Ser Leu Glu Ser Asp Ser Leu Thr Leu Pro Ala Thr Leu
465                 470                 475                 480
```

```
Asn Pro Gly Leu Asp Phe Ser Asp Glu Val Val Arg
            485                 490

<210> SEQ ID NO 61
<211> LENGTH: 1358
<212> TYPE: PRT
<213> ORGANISM: Zea mays (Maize)

<400> SEQUENCE: 61

Met Gly Lys Glu Ala Gly Ala Ala Glu Ser Ser Thr Val Val Leu Ala
1               5                   10                  15

Val Asn Gly Lys Arg Tyr Glu Ala Ala Gly Val Ala Pro Ser Thr Ser
            20                  25                  30

Leu Leu Glu Phe Leu Arg Thr Gln Thr Pro Val Arg Gly Pro Lys Leu
        35                  40                  45

Gly Cys Gly Glu Gly Gly Cys Gly Ala Cys Val Val Leu Val Ser Lys
    50                  55                  60

Tyr Asp Pro Ala Thr Asp Glu Val Thr Glu Phe Ser Ala Ser Ser Cys
65                  70                  75                  80

Leu Thr Leu Leu His Ser Val Asp Arg Cys Ser Val Thr Thr Ser Glu
                85                  90                  95

Gly Ile Gly Asn Thr Arg Asp Gly Tyr His Pro Val Gln Gln Arg Leu
            100                 105                 110

Ser Gly Phe His Ala Ser Gln Cys Gly Phe Cys Thr Pro Gly Met Cys
        115                 120                 125

Met Ser Ile Phe Ser Ala Leu Val Lys Ala Asp Asn Lys Ser Asp Arg
    130                 135                 140

Pro Asp Pro Pro Ala Gly Phe Ser Lys Ile Thr Thr Ser Glu Ala Glu
145                 150                 155                 160

Lys Ala Val Ser Gly Asn Leu Cys Arg Cys Thr Gly Tyr Arg Pro Ile
                165                 170                 175

Val Asp Thr Cys Lys Ser Phe Ala Ser Asp Val Asp Leu Glu Asp Leu
            180                 185                 190

Gly Leu Asn Cys Phe Trp Lys Lys Gly Glu Glu Pro Ala Glu Val Ser
        195                 200                 205

Arg Leu Pro Gly Tyr Asn Ser Gly Ala Val Cys Thr Phe Pro Glu Phe
    210                 215                 220

Leu Lys Ser Glu Ile Lys Ser Thr Met Lys Gln Val Asn Asp Val Pro
225                 230                 235                 240

Ile Ala Ala Ser Gly Asp Gly Trp Tyr His Pro Lys Ser Ile Glu Glu
                245                 250                 255

Leu His Arg Leu Phe Asp Ser Ser Trp Phe Asp Asp Ser Ser Val Lys
            260                 265                 270

Ile Val Ala Ser Asn Thr Gly Ser Gly Val Tyr Lys Asp Gln Asp Leu
        275                 280                 285

Tyr Asp Lys Tyr Ile Asp Ile Lys Gly Ile Pro Glu Leu Ser Val Ile
    290                 295                 300

Asn Lys Asn Asp Lys Ala Ile Glu Leu Gly Ser Val Val Ser Ile Ser
305                 310                 315                 320

Lys Ala Ile Glu Val Leu Ser Asp Gly Asn Leu Val Phe Arg Lys Ile
                325                 330                 335

Ala Asp His Leu Asn Lys Val Ala Ser Pro Phe Val Arg Asn Thr Ala
            340                 345                 350

Thr Ile Gly Gly Asn Ile Met Met Ala Gln Arg Leu Pro Phe Glu Ser
```

```
                355                 360                 365
Asp Val Ala Thr Val Leu Leu Ala Ala Gly Ser Thr Val Thr Val Gln
370                 375                 380

Val Ala Ser Lys Arg Leu Cys Phe Thr Leu Glu Glu Phe Leu Glu Gln
385                 390                 395                 400

Pro Pro Cys Asp Ser Arg Thr Leu Leu Leu Ser Ile Phe Ile Pro Glu
            405                 410                 415

Trp Gly Ser Asp Tyr Val Thr Phe Glu Thr Phe Arg Ala Ala Pro Arg
            420                 425                 430

Pro Phe Gly Asn Ala Val Ser Tyr Val Asn Ser Ala Phe Leu Ala Arg
            435                 440                 445

Thr Ser Gly Ser Leu Leu Ile Glu Asp Ile Cys Leu Ala Phe Gly Ala
450                 455                 460

Tyr Gly Val Asp His Ala Ile Arg Ala Lys Val Glu Asp Phe Leu
465                 470                 475                 480

Lys Gly Lys Ser Leu Ser Ser Phe Val Ile Leu Glu Ala Ile Lys Leu
            485                 490                 495

Leu Lys Asp Thr Val Ser Pro Ser Glu Gly Thr Thr His His Glu Tyr
            500                 505                 510

Arg Val Ser Leu Ala Val Ser Phe Leu Phe Ser Phe Leu Ser Ser Leu
            515                 520                 525

Ala Asn Ser Ser Ala Pro Ser Asn Ile Asp Thr Pro Asn Gly Ser
530                 535                 540

Tyr Thr His Glu Thr Gly Ser Asn Val Asp Ser Pro Glu Arg His Ile
545                 550                 555                 560

Lys Val Asp Ser Asn Asp Leu Pro Ile Arg Ser Arg Gln Glu Met Val
            565                 570                 575

Phe Ser Asp Glu Tyr Lys Pro Val Gly Lys Pro Ile Lys Lys Val Gly
            580                 585                 590

Ala Glu Ile Gln Ala Ser Gly Glu Ala Val Tyr Val Asp Asp Ile Pro
            595                 600                 605

Ala Pro Lys Asp Cys Leu Tyr Gly Ala Phe Ile Tyr Ser Thr His Pro
610                 615                 620

His Ala His Val Arg Ser Ile Asn Phe Lys Ser Ser Leu Ala Ser Gln
625                 630                 635                 640

Lys Val Ile Thr Val Ile Thr Ala Lys Asp Ile Pro Ser Gly Gly Glu
            645                 650                 655

Asn Ile Gly Ser Ser Phe Leu Met Gln Gly Glu Ala Leu Phe Ala Asp
            660                 665                 670

Pro Ile Ala Glu Phe Ala Gly Gln Asn Ile Gly Val Val Ile Ala Glu
            675                 680                 685

Thr Gln Arg Tyr Ala Asn Met Ala Ala Lys Gln Ala Val Val Glu Tyr
            690                 695                 700

Ser Thr Glu Asn Leu Gln Pro Pro Ile Leu Thr Ile Glu Asp Ala Ile
705                 710                 715                 720

Gln Arg Asn Ser Tyr Ile Gln Ile Pro Pro Phe Leu Ala Pro Lys Pro
            725                 730                 735

Val Gly Asp Tyr Asn Lys Gly Met Ala Glu Ala Asp His Lys Ile Leu
            740                 745                 750

Ser Ala Glu Val Lys Leu Glu Ser Gln Tyr Tyr Phe Tyr Met Glu Thr
            755                 760                 765

Gln Ala Ala Leu Ala Ile Pro Asp Glu Asp Asn Cys Ile Thr Ile Tyr
            770                 775                 780
```

```
Ser Ser Thr Gln Met Pro Glu Leu Thr Gln Asn Leu Ile Ala Arg Cys
785                 790                 795                 800

Leu Gly Ile Pro Phe His Asn Val Arg Val Ile Ser Arg Arg Val Gly
            805                 810                 815

Gly Gly Phe Gly Gly Lys Ala Met Lys Ala Thr His Thr Ala Cys Ala
        820                 825                 830

Cys Ala Leu Ala Ala Phe Lys Leu Arg Arg Pro Val Arg Met Tyr Leu
        835                 840                 845

Asp Arg Lys Thr Asp Met Ile Met Ala Gly Arg His Pro Met Lys
    850                 855                 860

Ala Lys Tyr Ser Val Gly Phe Lys Ser Asp Gly Lys Ile Thr Ala Leu
865                 870                 875                 880

His Leu Asp Leu Gly Ile Asn Ala Gly Ile Ser Pro Asp Val Ser Pro
            885                 890                 895

Leu Met Pro Arg Ala Ile Ile Gly Ala Leu Lys Lys Tyr Asn Trp Gly
            900                 905                 910

Thr Leu Glu Phe Asp Thr Lys Val Cys Lys Thr Asn Val Ser Ser Lys
            915                 920                 925

Ser Ala Met Arg Ala Pro Gly Asp Val Gln Gly Ser Phe Ile Ala Glu
930                 935                 940

Ala Ile Ile Glu His Val Ala Ser Ala Leu Ala Leu Asp Thr Asn Thr
945                 950                 955                 960

Val Arg Arg Lys Asn Leu His Asp Phe Glu Ser Leu Glu Val Phe Tyr
            965                 970                 975

Gly Glu Ser Ala Gly Glu Ala Ser Thr Tyr Ser Leu Val Ser Met Phe
            980                 985                 990

Asp Lys Leu Ala Leu Ser Pro Glu Tyr Gln His Arg Ala Ala Met Ile
            995                 1000                1005

Glu Gln Phe Asn Ser Ser Asn Lys Trp Lys Lys Arg Gly Ile Ser
    1010                1015                1020

Cys Val Pro Ala Thr Tyr Glu Val Asn Leu Arg Pro Thr Pro Gly
    1025                1030                1035

Lys Val Ser Ile Met Asn Asp Gly Ser Ile Ala Val Glu Val Gly
    1040                1045                1050

Gly Ile Glu Ile Gly Gln Gly Leu Trp Thr Lys Val Lys Gln Met
    1055                1060                1065

Thr Ala Phe Gly Leu Gly Gln Leu Cys Pro Asp Gly Gly Glu Cys
    1070                1075                1080

Leu Leu Asp Lys Val Arg Val Ile Gln Ala Asp Thr Leu Ser Leu
    1085                1090                1095

Ile Gln Gly Gly Met Thr Ala Gly Ser Thr Thr Ser Glu Thr Ser
    1100                1105                1110

Cys Glu Thr Val Arg Gln Ser Cys Val Ala Leu Val Glu Lys Leu
    1115                1120                1125

Asn Pro Ile Lys Glu Ser Leu Glu Ala Lys Ser Asn Thr Val Glu
    1130                1135                1140

Trp Ser Ala Leu Ile Ala Gln Ala Ser Met Ala Ser Val Asn Leu
    1145                1150                1155

Ser Ala Gln Pro Tyr Trp Thr Pro Asp Pro Ser Phe Lys Ser Tyr
    1160                1165                1170

Leu Asn Tyr Gly Ala Gly Thr Ser Glu Val Glu Val Asp Ile Leu
    1175                1180                1185
```

| | | | | | | | | | | |
|---|---|---|---|---|---|---|---|---|---|---|
| Thr | Gly | Ala | Thr | Thr | Ile | Leu | Arg | Ser | Asp | Leu | Val | Tyr | Asp | Cys |
| | 1190 | | | | 1195 | | | | 1200 | |
| Gly | Gln | Ser | Leu | Asn | Pro | Ala | Val | Asp | Leu | Gly | Gln | Ile | Glu | Gly |
| | 1205 | | | | 1210 | | | | 1215 | |
| Cys | Phe | Val | Gln | Gly | Ile | Gly | Phe | Phe | Thr | Asn | Glu | Asp | Tyr | Lys |
| | 1220 | | | | 1225 | | | | 1230 | |
| Thr | Asn | Ser | Asp | Gly | Leu | Val | Ile | His | Asp | Gly | Thr | Trp | Thr | Tyr |
| | 1235 | | | | 1240 | | | | 1245 | |
| Lys | Ile | Pro | Thr | Val | Asp | Asn | Ile | Pro | Lys | Glu | Phe | Asn | Val | Glu |
| | 1250 | | | | 1255 | | | | 1260 | |
| Met | Phe | Asn | Ser | Ala | Pro | Asp | Lys | Lys | Arg | Val | Leu | Ser | Ser | Lys |
| | 1265 | | | | 1270 | | | | 1275 | |
| Ala | Ser | Gly | Glu | Pro | Pro | Leu | Val | Leu | Ala | Thr | Ser | Val | His | Cys |
| | 1280 | | | | 1285 | | | | 1290 | |
| Ala | Met | Arg | Glu | Ala | Ile | Arg | Ala | Ala | Arg | Lys | Glu | Phe | Ser | Val |
| | 1295 | | | | 1300 | | | | 1305 | |
| Ser | Thr | Ser | Pro | Ala | Lys | Ser | Ala | Val | Thr | Phe | Gln | Met | Asp | Val |
| | 1310 | | | | 1315 | | | | 1320 | |
| Pro | Ala | Thr | Met | Pro | Val | Val | Lys | Glu | Leu | Cys | Gly | Leu | Asp | Val |
| | 1325 | | | | 1330 | | | | 1335 | |
| Val | Glu | Arg | Tyr | Leu | Glu | Asn | Val | Ser | Ala | Ala | Ser | Ala | Gly | Pro |
| | 1340 | | | | 1345 | | | | 1350 | |
| Asn | Thr | Ala | Lys | Ala |
| | 1355 |

<210> SEQ ID NO 62
<211> LENGTH: 747
<212> TYPE: DNA
<213> ORGANISM: Caulobacter crescentus

<400> SEQUENCE: 62

```
atgtcctcag ccatctatcc cagcctgaag ggcaagcgcg tcgtcatcac cggcggcggc      60
tcgggcatcg gggccggcct caccgccggc ttcgcccgtc agggcgcgga ggtgatcttc     120
ctcgacatcg ccgacgagga ctccagggct cttgaggccg agctggccgg ctcgccgatc     180
ccgccggtct acaagcgctg cgacctgatg aacctcgagg cgatcaaggc ggtcttcgcc     240
gagatcggcg acgtcgacgt gctggtcaac aacgccggca tgacgaccg ccacaagctg      300
gccgacgtga ccggcgccta tgggacgag cggatcaacg tcaacctgcg ccacatgctg      360
ttctgcaccc aggccgtcgc gccgggcatg aagaagcgtg cggcggggc ggtgatcaac      420
ttcggttcga tcagctggca cctggggctt gaggacctcg tcctctacga aaccgccaag     480
gccggcatcg aaggcatgac ccgcgcgctg gcccgggagc tgggtcccga cgacatccgc     540
gtcacctgcg tggtgccggg caacgtcaag accaagcgcc aggagaagtg gtacacgccc     600
gaaggcgagg cccagatcgt ggcggcccaa tgcctgaagg gccgcatcgt cccggagaac     660
gtcgccgcgc tggtgctgtt cctggcctcg gatgacgcgt cgctctgcac cggccacgaa     720
tactggatcg acgccggctg cgcgttga                                        747
```

<210> SEQ ID NO 63
<211> LENGTH: 870
<212> TYPE: DNA
<213> ORGANISM: Caulobacter crescentus

<400> SEQUENCE: 63

```
atgaccgctc aagtcacttg cgtatgggat ctgaaggcca cgttgggcga aggcccgatc      60
```

```
tggcatggcg acaccctgtg gttcgtcgac atcaagcagc gtaaaatcca caactaccac    120
cccgccaccg gcgagcgctt cagcttcgac gcgccggatc aggtgaccct cctcgcgccg    180
atcgtcggcg cgaccggctt tgtcgtcggt ctgaagaccg ggattcaccg cttccacccg    240
gccacgggct tcagcctgct gctcgaggtc gaggacgcgg cgctgaacaa ccgccccaac    300
gacgccacgg tcgacgcgca aggccgtctg tggttcggca ccatgcacga cggggaagag    360
aacaatagcg gctcgctcta tcggatggac ctcaccggcg tcgcccggat ggaccgcgac    420
atctgcatca ccaacggccc gtgcgtctcg cccgacggca agaccttcta ccacaccgac    480
accctggaaa agacgatcta cgccttcgac ctggccgagg acggcctgct gtcgaacaag    540
cgcgtcttcg tgcagttcgc cctgggcgac gatgtctatc cggacggttc ggtcgtcgat    600
tccgaaggct atctgtggac cgccctgtgg ggcggtttcg gcgcggtccg cttctcgccg    660
caaggcgacg ccgtgacgcg catcgaactg cccgccccca acgtcaccaa gccctgcttc    720
ggcgggcctg acctgaagac cctctatttc accaccgccc gcaagggcct gagcgacgag    780
accctggccc agtacccgct ggccggcggt gtgttcgccg ttccggtcga tgtggccggc    840
caaccccagc atgaggtccg ccttgtctaa                                     870
```

<210> SEQ ID NO 64
<211> LENGTH: 1968
<212> TYPE: DNA
<213> ORGANISM: Escherichia coli

<400> SEQUENCE: 64

```
atgtctgttc gcaatatttt tgctgacgag agccacgata tttacaccgt cagaacgcac     60
gccgatggcc cggacggcga actcccatta accgcagaga tgcttatcaa ccgcccgagc    120
ggggatctgt tcggtatgac catgaatgcc ggaatgggtt ggtctccgga cgagctggat    180
cgggacggta ttttactgct cagtacactc ggtggcttac gcggcgcaga cggtaaaccc    240
gtggcgctgg cgttgcacca ggggcattac gaactggaca tccagatgaa agcggcggcc    300
gaggttatta aagccaacca tgccctgccc tatgccgtgt acgtctccga tccttgtgac    360
gggcgtactc agggtacaac ggggatgttt gattcgctac ataccgaaa tgacgcatcg    420 atggtaatgc gccgccttat tgctctctg cccgacgcga aagcagttat tggtgtggcg    480
agttgcgata aggggcttcc ggccaccatg atggcactcg ccgcgcagca aacatcgca    540 accgtgctgg tccccggcgg cgcgacgctg cccgcaaagg atggagaaga caacggcaag    600
gtgcaaacca ttggcgcacg cttcgccaat ggcgaattat ctctacagga cgcacgccgt    660
gcgggctgta aagcctgtgc ctcttccggc ggcggctgtc aattttttggg cactgccggg    720 acatctcagg tggtggccga aggattggga ctggcaatcc cacattcagc cctggcccct    780
tccggtgagc ctgtgtggcg ggagatcgcc agagcttccg cgcgagctgc gctgaacctg    840
agtcaaaaag gcatcaccac ccgggaaatt ctcaccgata aagcgataga gaatgcgatg    900
acggtccatg ccgcgttcgg tggttcaaca aacctgctgt acacatccc ggcaattgct    960 caccaggcag gttgccatat cccgaccgtt gatgactgga tccgcatcaa caagcgcgtg   1020
ccccgactgg tgagcgtact gcctaatggc ccggtttatc atccaacggt caatgccttt   1080
atggcaggtg gtgtgccgga agtcatgttg catctgcgca gcctcggatt gttgcatgaa   1140
gacgttatga cggttaccgg cagcacgctg aaagaaaacc tcgactggtg ggagcactcc   1200
gaacggcgtc agcggttcaa gcaactcctg ctcgatcagg aacaaatcaa cgctgacgaa   1260
```

```
gtgatcatgt ctccgcagca agcaaaagcg cgcggattaa cctcaactat caccttcccg   1320
gtgggcaata ttgcgccaga aggttcggtg atcaaatcca ccgccattga cccctcgatg   1380
attgatgagc aaggtatcta ttaccataaa ggtgtggcga aggtttatct gtccgagaaa   1440
agtgcgattt acgatatcaa acatgacaag atcaaggcgg cgatattct  ggtcattatt   1500 ggcgttggac cttcaggtac agggatggaa gaaacctacc aggttaccag tgccctgaag   1560
catctgtcat acgtaagca tgtttcgtta atcaccgatg cacgtttctc gggcgttct    1620
```
```
actggcgcgt gcatcggcca tgtggggcca gaagcgctgg ccggaggccc catcggtaaa   1680
ttacgcaccg gggatttaat tgaaattaaa attgattgtc gcgagcttca cggcgaagtc   1740
aatttcctcg gaacccgtag cgatgaacaa ttaccttcac aggaggaggc aactgcaata   1800
ttaaatgcca gacccagcca tcaggattta cttcccgatc ctgaattgcc agatgatacc   1860
cggctatggg caatgcttca ggccgtgagt ggtgggacat ggaccggttg tatttatgat   1920
gtaaacaaaa ttggcgcggc tttgcgcgat tttatgaata aaaactga                1968
```

<210> SEQ ID NO 65
<211> LENGTH: 1383
<212> TYPE: DNA
<213> ORGANISM: Escherichia coli

<400> SEQUENCE: 65

```
atgacgcaat taaccatgaa agacaaaatt ggctacgggc tgggagacac cgcctgcggc     60
ttcgtctggc aggccacgat gttcctgctg gcctatttct acaccgacgt cttcggcctg    120
tcggcgggga ttatgggcac gctgttttg  gtctcccgcg tgctcgacgc cgtcaccgac    180
ccgctgatgg ggctgctggt agaccgcacc cgcacgcggc acggccagtt ccgcccgttc    240
ctgctgtggg gggccatccc gttcggcatc gtctgcgtgc tgaccttcta cacgccggac    300
ttctccgcac agggcaagat catctacgcc tgcgtgacct acattctcct gaccctggtc    360 tacacctttcg ttaacgtgcc gtactgcgcc atgccgggcg tcatcaccgc cgacccgaaa    420
gagcgtcacg ccctgcagtc ctggcgcttc ttcctggcgg cggcgggctc gctcgctatc    480
agcggcatcg cgctgccgct ggtgagcatc atcggcaaag gggacgagca ggtgggctac    540
ttcggcgcca tgtgcgtgct ggggctgagc ggcgtggtgc tgctctacgt ctgcttcttc    600
acgaccaaag agcgctacac ctttgaggtg cagcccgggct cgtcggtggc gaaagacctt    660
aagctgctgc tgggcaacag ccagtggcgc atcatgtgcg cgttcaagat gatggcgacc    720
tgctccaacg tggtgcgcgg cggggcgacg ctctacttcg tgaaatacgt gatggatcac    780
ccggagttgg cgacccagtt tttactttac ggcagcctcg ccaccatgtt cggctcgctt    840
tgctcctcac gcctgctggg ccgcttcgac cgcgtcaccg ccttcaagtg gatcatcgtc    900
gcctactcgc tgatcagcct gctgattttc gtcaccccgg cggagcacat cgcgctcatt    960 tttgcccctca acatcctgtt cctgttcgtc tttaatacca ccacgccgct gcagtggctg   1020
atggcttctg acgtggtgga ctacgaggag agccgcagcg tcgccgcct  cgacgggctg   1080 gtgttctcca cctacctgtt cagcctgaag attggcctgg cgattggcgg ggcggtggtg   1140
ggctggatcc tggcgtacgt caactattcc gccagcagca gcgtgcagcc ggttgaggtg   1200
ctcaccacca tcaaaattct gttctgcgtg gtgccggtgg tgctctacgc gggcatgttc   1260
atcatgctgt cgctctacaa gctcaccgat gcccgcgtgg aggccatcag ccggcagctg   1320
attaagcacc gcgcggcgca gggcgaggcc gttcccgacg ccgcgacagc cgcatcccat   1380
taa                                                                  1383
```

<210> SEQ ID NO 66
<211> LENGTH: 1041
<212> TYPE: DNA
<213> ORGANISM: Escherichia coli

<400> SEQUENCE: 66

| | | |
|---|---|---|
| atgcagaaca tcatccgaaa aggaggaact atgaaggctg cagttgttac gaaggatcat | 60 |
| catgttgacg ttacgtataa aacactgcgc tcactgaaac atggcgaagc cctgctgaaa | 120 |
| atggagtgtt gtggtgtatg tcataccgat cttcatgtta agaatggcga ttttggtgac | 180 |
| aaaaccggcg taattctggg ccatgaaggc atcggtgtgg tggcagaagt gggtccaggt | 240 |
| gtcacctcat aaaaccagg cgatcgtgcc agcgtggcgt ggttctacga aggatgcggt | 300 |
| cattgcgaat actgtaacag tggtaacgaa acgctctgcc gttcagttaa aaatgccgga | 360 |
| tacagcgttg atggcgggat ggcggaagag tgcatcgtgg tcgccgatta cgcggtaaaa | 420 |
| gtgccagatg tctggactc ggcggcggcc agcagcatta cctgtgcggg agtcaccacc | 480 |
| tacaaagccg ttaagctgtc aaaaattcgt ccagggcagt ggattgctat ctacggtctt | 540 |
| ggcggtctgg gtaaccctcgc cctgcaatac gcgaagaatg tctttaacgc caaagtgatc | 600 |
| gccattgatg tcaatgatga gcagttaaaa ctggcaaccg aaatgggcgc agatttagcg | 660 |
| attaactcac acaccgaaga cgccgccaaa attgtgcagg agaaaactgg tggcgctcac | 720 |
| gctgcggtgg taacagcggt agctaaagct gcgtttaact cggcagttga tgctgtccgt | 780 |
| gcaggcggtc gtgttgtggc tgtcggtcta ccgccgagt ctatgagcct ggatatccca | 840 |
| cgtcttgtgc tggatggtat tgaagtggtc ggttcgctgg tcggcacgcg ccaggattta | 900 |
| actgaagcct tccagtttgc cgccgaaggt aaagtggtgc cgaaagtcgc cctgcgtccg | 960 |
| ttagcggaca tcaacaccat ctttactgag atggaagaag gcaaaatccg tggccgcatg | 1020 |
| gtgattgatt ccgtcacta a | 1041 |

<210> SEQ ID NO 67
<211> LENGTH: 1164
<212> TYPE: DNA
<213> ORGANISM: Escherichia coli

<400> SEQUENCE: 67

| | | |
|---|---|---|
| atgaacaact ttaatctgca cacccccaacc cgcattctgt ttggtaaagg cgcaatcgct | 60 |
| ggtttacgcg aacaaattcc tcacgatgct cgcgtattga ttacctacgg cggcggcagc | 120 |
| gtgaaaaaaa ccggcgttct cgatcaagtt ctggatgccc tgaaaggcat ggacgtgctg | 180 |
| gaatttggcg gtattgagcc aaacccggct tatgaaacgc tgatgaacgc cgtgaaactg | 240 |
| gttcgcgaac agaaagtgac tttcctgctg gcggttggcg gcggttctgt actggacggc | 300 |
| accaaattta cgccgcagc ggctaactat ccggaaaata tcgatccgtg gcacattctg | 360 |
| caaacgggcg gtaaagagat taaagcgcc atcccgatgg gctgtgtgct gacgctgcca | 420 |
| gcaaccggtt cagaatccaa cgcaggcgcg gtgatctccc gtaaaaccac aggcgacaag | 480 |
| caggcgttcc attctgccca tgttcagccg gtatttgccg tgctcgatcc ggtttatacc | 540 |
| tacaccctgc cgccgcgtca ggtggctaac ggcgtagtgg acgcctttgt acacaccgtg | 600 |
| gaacagtatg ttaccaaacc ggttgatgcc aaaattcagg accgtttcgc agaaggcatt | 660 |
| ttgctgacgc taatcgaaga tggtccgaaa gccctgaaag agccagaaaa ctacgatgtg | 720 |
| cgcgccaacg tcatgtgggc ggcgactcag gcgctgaacg gtttgattgg cgctggcgta | 780 |

```
ccgcaggact gggcaacgca tatgctgggc cacgaactga ctgcgatgca cggtctggat      840
cacgcgcaaa cactggctat cgtcctgcct gcactgtgga atgaaaaacg cgataccaag      900
cgcgctaagc tgctgcaata tgctgaacgc gtctggaaca tcactgaagg ttccgatgat      960
gagcgtattg acgccgcgat tgccgcaacc cgcaatttct ttgagcaatt aggcgtgccg     1020
acccacctct ccgactacgg tctggacggc agctccatcc cggctttgct gaaaaaactg     1080
gaagagcacg gcatgaccca actgggcgaa aatcatgaca ttacgttgga tgtcagccgc     1140
cgtatatacg aagccgcccg ctaa                                            1164

<210> SEQ ID NO 68
<211> LENGTH: 1587
<212> TYPE: DNA
<213> ORGANISM: Pseudomonas putida

<400> SEQUENCE: 68
atggcttcgg tacacggcac cacatacgaa ctcttgcgac gtcaaggcat cgatacggtc       60
ttcggcaatc ctggctcgaa cgagctcccg tttttgaagg actttccaga ggactttcga      120
tacatcctgg ctttgcagga agcgtgtgtg gtgggcattg cagacggcta tgcgcaagcc      180
agtcggaagc cggcttttcat taacctgcat tctgctgctg gtaccggcaa tgctatgggt      240
gcactcagta acgcctggaa ctcacattcc cgctgatcg tcactgccgg ccagcagacc       300
agggcgatga ttggcgttga agctctgctg accaacgtcg atgccgccaa cctgccacga      360
ccacttgtca aatggagcta cgagcccgca agcgcagcag aagtccctca tgcgatgagc      420
agggctatcc atatggcaag catggcgcca caaggccctg tctatctttc ggtgccatat      480
gacgattggg ataaggatgc tgatcctcag tcccaccacc tttttgatcg ccatgtcagt      540
tcatcagtac gcctgaacga ccaggatctc gatattctgg tgaaagctct caacagcgca      600
tccaacccgg cgatcgtcct gggcccggac gtcgacgcag caaatgcgaa cgcagactgc      660
gtcatgttgg ccgaacgcct caaagctccg gtttgggttg cgccatccgc tccacgctgc      720
ccattcccta cccgtcatcc ttgcttccgt ggattgatgc cagctggcat cgcagcgatt      780
tctcagctgc tcgaaggtca cgatgtggtt ttggtaatcg cgctccagt gttccgttac       840 caccaatacg acccaggtca atatctcaaa cctggcacgc gattgatttc ggtgacctgc      900
gacccgctcg aagctgcacg cgcgccaatg ggcgatgcga tcgtggcaga cattggtgcg      960
atggctagcg ctcttgccaa cttggttgaa gagagcagcc gccagctccc aactgcagct     1020
ccggaacccg cgaaggttga ccaagacgct ggccgacttc acccagagac agtgttcgac     1080
acactgaacg acatggcccc ggagaatgcg atttacctga cgagtcgac ttcaacgacc      1140 gcccaaatgt ggcagcgcct gaacatgcgc aaccctggta gctactactt ctgtgcagct     1200
ggcggactgg gcttcgccct gcctgcagca attggcgttc aactcgcaga acccgagcga     1260
caagtcatcg ccgtcattgg cgacggatcg gcgaactaca gcattagtgc gttgtggact     1320
gcagctcagt acaacatccc cactatcttc gtgatcatga caacggcac ctacggtgcg      1380 ttgcgatggt ttgccggcgt tctcgaagca gaaaacgttc ctgggctgga tgtgccaggg     1440
atcgacttcc gcgcactcgc caagggctat ggtgtccaag cgctgaaagc cgacaacctt     1500
gagcagctca agggttcgct acaagaagcg ctttctgcca aaggcccggt acttatcgaa     1560
gtaagcaccg taagcccggt gaagtga                                         1587

<210> SEQ ID NO 69
<211> LENGTH: 1323
```

```
<212> TYPE: DNA
<213> ORGANISM: Escherichia coli

<400> SEQUENCE: 69
atgcaagcct attttgacca gctcgatcgc gttcgttatg aaggctcaaa atcctcaaac      60
ccgttagcat tccgtcacta caatcccgac gaactggtgt tgggtaagcg tatggaagag     120
cacttgcgtt ttgccgcctg ctactggcac accttctgct ggaacggggc ggatatgttt     180
ggtgtggggg cgtttaatcg tccgtggcag cagcctggtg aggcactggc gttggcgaag     240
cgtaaagcag atgtcgcatt tgagtttttc cacaagttac atgtgccatt ttattgcttc     300
cacgatgtga tgtttccccc tgagggcgcg tcgttaaaag agtacatcaa taattttgcg     360
caaatggttg atgtcctggc aggcaagcaa gaagagagcg cgtgaagct gctgtgggga      420
acggccaact gctttacaaa ccctcgctac ggcgcgggtg cggcgacgaa cccagatcct     480
gaagtcttca gctgggcggc aacgcaagtt gttacagcga tggaagcaac ccataaattg     540
ggcggtgaaa actatgtcct gtggggcggt cgtgaaggtt acgaaacgct gttaaatacc     600
gacttgcgtc aggagcgtga caactgggc cgctttatgc agatggtggt tgagcataaa      660
cataaaatcg gtttccaggg cacgttgctt atcgaaccga aaccgcaaga accgaccaaa     720
catcaatatg attacgatgc cgcgacggtc tatggcttcc tgaaacagtt tggtctggaa     780
aaagagatta aactgaacat tgaagctaac cacgcgacgc tggcaggtca ctctttccat     840
catgaaatag ccaccgccat tgcgcttggc ctgttcggtt ctgtcgacgc caaccgtggc     900
gatgcgcaac tgggctggga caccgaccag ttcccgaaca gtgtggaaga gaatgcgctg     960
gtgatgtatg aaattctcaa gcaggcggt ttcaccaccg gtggtctgaa cttcgatgcc     1020
aaagtacgtc gtcaaagtac tgataaatat gatctgtttt acggtcatat cggcgcgatg    1080
gatacgatgg cactggcgct gaaaattgca gcgcgcatga ttgaagatgg cgagctggat    1140
aaacgcatcg cgcagcgtta ttccggctgg aatagcgaat tgggccagca atcctgaaa    1200
ggccaaatgt cactggcaga tttagccaaa tatgctcagg aacatcattt gtctccggtg    1260
catcagagtg gtcgccagga caactggaa atctggtaa accattatct gttcgacaaa     1320
taa                                                                 1323

<210> SEQ ID NO 70
<211> LENGTH: 1455
<212> TYPE: DNA
<213> ORGANISM: Escherichia coli

<400> SEQUENCE: 70
atgtatatcg ggatagatct tggcacctcg ggcgtaaaag ttatttttgct caacgagcag     60
ggtgaggtgg ttgctgcgca aacggaaaag ctgaccgttt cgcgcccgca tccactctgg    120
tcggaacaag acccggaaca gtggtggcag gcaactgatc gcgcaatgaa agctctgggc    180
gatcagcatt ctctgcagga cgttaaagca ttgggtattg ccggccagat gcacggagca    240
accttgctgg atgctcagca acgggtgtta cgccctgcca ttttgtggaa cgacgggcgc    300
tgtgcgcaag agtgcacttt gctggaagcg cgagttccgc aatcgcgggt gattaccggc    360
aacctgatga tgcccggatt tactgcgcct aaattgctat gggttcagcg gcatgagccg    420
gagatattcc gtcaaatcga caaagtatta ttaccgaaag attacttgcg tctgcgtatg    480
acgggggagt tgccagcga tatgtctgac gcagctggca ccatgtggct ggatgtcgca    540
aagcgtgact ggagtgacgt catgctgcag gcttgcgact tatctcgtga ccagatgccc    600
```

```
gcattatacg aaggcagcga aattactggt gctttgttac ctgaagttgc gaaagcgtgg    660
ggtatggcga cggtgccagt tgtcgcaggc ggtggcgaca atgcagctgg tgcagttggt    720
gtgggaatgg ttgatgctaa tcaggcaatg ttatcgctgg ggacgtcggg ggtctatttt    780
gctgtcagcg aagggttctt aagcaagcca gaaagcgccg tacatagctt ttgccatgcg    840
ctaccgcaac gttggcattt aatgtctgtg atgctgagtg cagcgtcgtg tctggattgg    900
gccgcgaaat taaccggcct gagcaatgtc ccagctttaa tcgctgcagc tcaacaggct    960
gatgaaagtg ccgagccagt ttggtttctg ccttatcttt ccggcgagcg tacgccacac   1020
aataatcccc aggcgaaggg ggttttcttt ggtttgactc atcaacatgg ccccaatgaa   1080
ctggcgcgag cagtgctgga aggcgtgggt tatgcgctgg cagatggcat ggatgtcgtg   1140
catgcctgcg gtattaaacc gcaaagtgtt acgttgattg ggggcggggc gcgtagtgag   1200
tactggcgtc agatgctggc ggatatcagc ggtcagcagc tcgattaccg tacggggggg   1260
gatgtggggc cagcactggg cgcagcaagg ctggcgcaga tcgcggcgaa tccagagaaa   1320
tcgctcattg aattgttgcc gcaactaccg ttagaacagt cgcatctacc agatgcgcag   1380
cgttatgccg cttatcagcc acgacgagaa acgttccgtc gcctctatca gcaacttctg   1440
ccattaatgg cgtaa                                                     1455

<210> SEQ ID NO 71
<211> LENGTH: 906
<212> TYPE: DNA
<213> ORGANISM: Escherichia coli

<400> SEQUENCE: 71
atgaaaaaat tcagcggcat tattccaccg gtatccagca cgtttcatcg tgacggaacc     60
cttgataaaa aggcaatgcg cgaagttgcc gacttcctga ttaataaagg ggtcgacggg    120
ctgttttatc tgggtaccgg tggtgaattt agccaaatga atacagccca gcgcatggca    180
ctcgccgaag aagctgtaac cattgtcgac gggcgagtgc cggtattgat tggcgtcggt    240
tccccttcca ctgacgaagc ggtcaaactg gcgcagcatg cgcaagccta cggcgctgat    300
ggtatcgtcg ccatcaaccc ctactactgg aaagtcgcac cacgaaatct tgacgactat    360
taccagcaga tcgcccgtag cgtcacccta ccggtgatcc tgtacaactt ccggatctg    420 acgggtcagg acttaacccc ggaaaccgtg acgcgtctgg ctctgcaaaa cgagaatatc    480
gttggcatca aagacaccat cgacagcgtt ggtcacttgc gtacgatgat caacacagtt    540
aagtcggtac gcccgtcgtt ttcggtattc tgcggttacg atgatcattt gctgaatacg    600
atgctgctgg gcggcgacgg tgcgataacc gccagcgcta actttgctcc ggaactctcc    660
gtcggcatct accgcgcctg gcgtgaaggc gatctggcga ccgctgcgac gctgaataaa    720
aaactactac aactgcccgc tatttacgcc ctcgaaacac cgtttgtctc actgatcaaa    780
tacagcatgc agtgtgtcgg gctgcctgta gagacatatt gcttaccacc gattcttgaa    840
gcatctgaag aagcaaaaga taaagtccac gtgctgctta ccgcgcaggg cattttacca    900
gtctga                                                               906

<210> SEQ ID NO 72
<211> LENGTH: 909
<212> TYPE: DNA
<213> ORGANISM: Escherichia coli

<400> SEQUENCE: 72
atgccgcagt ccgcgttgtt cacgggaatc attccccctg tctccaccat ttttaccgcc     60
```

```
gacggccagc tcgataagcc gggcaccgcc gcgctgatcg acgatctgat caaagcaggc      120
gttgacggcc tgttcttcct gggcagcggt ggcgagttct cccagctcgg cgccgaagag      180
cgtaaagcca ttgcccgctt tgctatcgat catgtcgatc gtcgcgtgcc ggtgctgatc      240
ggcaccggcg gcaccaacgc ccgggaaacc atcgaactca gccagcacgc gcagcaggcg      300
ggcgcggacg gcatcgtggt gatcaacccc tactactgga agtgtcgga agcgaacctg       360 atccgctatt tcgagcaggt ggccgacagc gtcacgctgc cggtgatgct ctataacttc      420
ccggcgctga ccgggcagga tctgactccg gcgctggtga aaaccctcgc cgactcgcgc      480
agcaatatta tcggcatcaa agacaccatc gactccgtcg cccacctgcg cagcatgatc      540
cataccgtca aggtgccca tccgcacttc accgtgctct gcggctacga cgatcatctg       600
ttcaataccc tgctgctcgg cggcgacggg gcgatatcgg cgagcggcaa ctttgccccg      660
caggtgtcgg tgaatcttct gaaagcctgg cgcgacgggg acgtggcgaa agcggccggg      720
tatcatcaga ccttgctgca aattccgcag atgtatcagc tggatacgcc gtttgtgaac      780
gtgattaaag aggcgatcgt gctctgcggt cgtcctgtct ccacgcacgt gctgccgccc      840
gcctcgccgc tggacgagcc gcgcaaggcg cagctgaaaa ccctgctgca acagctcaag      900
ctttgctga                                                             909

<210> SEQ ID NO 73
<211> LENGTH: 975
<212> TYPE: DNA
<213> ORGANISM: Escherichia coli

<400> SEQUENCE: 73
atgaagccgt ccgttatcct ctacaaagcc ttacctgatg atttactgca acgcctgcaa       60
gagcatttca ccgttcacca ggtggcaaac ctcagcccac aaaccgtcga caaaatgca      120 gcaattttg ccgaagctga aggtttactg ggttcaaacg agaatgtaaa tgccgcattg      180
ctggaaaaaa tgccgaaact gcgtgccaca tcaacgatct ccgtcggcta tgacaatttt      240
gatgtcgatg cgcttaccgc ccgaaaaatt ctgctgatgc acacgccaac cgtattaaca      300
gaaaccgtcg ccgatacgct gatggcgctg gtgttgtcta ccgtcgtcg ggttgtggag       360 gtagcagaac gggtaaaagc aggcgaatgg accgcgagca taggcccgga ctggtacggc      420
actgacgttc accataaaac actgggcatt gtcgggatgg acggatcgg catggcgctg       480 gcacaacgtg cgcactttgg cttcaacatg cccatcctct ataacgcgcg ccgccaccat      540
aaagaagcag aagaacgctt caacgcccgc tactgcgatt tggatactct gttacaagag      600
tcagatttcg tttgcctgat cctgccgtta actgatgaga cgcatcatct gtttggcgca      660
gaacaattcg ccaaaatgaa atcctccgcc attttcatta atgccggacg tggcccggtg      720
gttgacgaaa atgcactgat cgcagcattg cagaaaggcg aaattcacgc tgccgggctg      780
gatgtcttcg aacaagagcc actgtccgta gattcgccgt tgctctcaat ggccaacgtc      840
gtcgcagtac cgcatattgg atctgccacc catgagacgc gttatggcat ggccgcctgt      900
gccgtggata atttgattga tgcgttacaa ggaaaggttg agaagaactg tgtgaatccg      960
cacgtcgcgg actaa                                                      975

<210> SEQ ID NO 74
<211> LENGTH: 939
<212> TYPE: DNA
<213> ORGANISM: Escherichia coli
```

<400> SEQUENCE: 74

```
atggatatca tcttttatca cccaacgttc gatacccaat ggtggattga ggcactgcgc      60
aaagctattc ctcaggcaag agtcagagca tggaaaagcg gagataatga ctctgctgat     120
tatgctttag tctggcatcc tcctgttgaa atgctggcag ggcgcgatct taaagcggtg     180
ttcgcactcg gggccggtgt tgattctatt ttgagcaagc tacaggcaca ccctgaaatg     240
ctgaacccctt ctgttccact ttttcgcctg gaagataccg gtatgggcga gcaaatgcag    300
gaatatgctg tcagtcaggt gctgcattgg tttcgacgtt ttgacgatta tcgcatccag    360
caaaatagtt cgcattggca accgctgcct gaatatcatc gggaagattt taccatcggc    420
attttgggcg caggcgtact gggcagtaaa gttgctcaga gtctgcaaac ctggcgcttt    480
ccgctgcgtt gctggagtcg aacccgtaaa tcgtggcctg gcgtgcaaag ctttgccgga    540
cgggaagaac tgtctgcatt tctgagccaa tgtcgggtat tgattaattt gttaccgaat    600
accccctgaaa ccgtcggcat tattaatcaa caattactcg aaaaattacc ggatggcgcg    660
tatctcctca acctggcgcg tggtgttcat gttgtggaag atgacctgct cgcggcgctg    720
gatagcggca aagttaaagg cgcaatgttg gatgttttta atcgtgaacc cttaccgcct    780
gaaagtccgc tctggcaaca tccacgcgtg acgataacac cacatgtcgc cgcgattacc    840
cgtcccgctg aagctgtgga gtacatttct cgcaccattg cccagctcga aaaggggag    900
agggtctgcg ggcaagtcga ccgcgcacgc ggctactaa                           939
```

<210> SEQ ID NO 75
<211> LENGTH: 1434
<212> TYPE: DNA
<213> ORGANISM: Escherichia coli

<400> SEQUENCE: 75

```
atgtttaaga atgcatttgc taacctgcaa aaggtcggta atcgctgat gctgccggta      60
tccgtactgc ctatcgcagg tattctgctg gcgtcggtt ccgcgaattt cagctggctg     120
cccgccgttg tatcgcatgt tatggcagaa gcaggcggtt ccgtctttgc aaacatgcca    180
ctgatttttg cgatcggtgt cgccctcggc tttaccaata cgatggcgt atccgcgctg    240
gccgcagttg ttgcctatgg catcatggtt aaaaccatgg ccgtggttgc gccactggta    300
ctgcatttac ctgctgaaga atcgcctct aaacacctgg cggatactgg cgtactcgga    360
gggattatct ccggtgcgat cgcagcgtac atgtttaacc gtttctaccg tattaagctg    420
cctgagtatc ttggcttctt tgccggtaaa cgctttgtgc cgatcatttc tggcctggct    480
gccatcttta ctggcgttgt gctgtccttc atttggccgc cgattggttc tgcaatccag    540
accttctctc agtgggctgc ttaccagaac ccggtagttg cgtttggcat ttacggtttc    600
atcgaacgtt gcctggtacc gtttggtctg caccacatct ggaacgtacc tttccagatg    660
cagattggtg aatacaccaa cgcagcaggt caggttttcc acggcgacat tccgcgttat    720
atggcgggta cccgactgc gggtaaactg tctggtggct tcctgttcaa aatgtacggt    780
ctgccagctg ccgcaattgc tatctggcac tctgctaaac cagaaaaccg cgcgaaagtg    840
ggcggtatta tgatctccgc ggcgctgacc tcgttcctga ccggtatcac cgagccgatc    900
gagttctcct tcatgttcgt tgcgccgatc ctgtacatca tccacgcgat tctggcaggc    960
ctggcattcc caatctgtat tcttctgggg atgcgtgacg gtacgtcgtt ctcgcacggt   1020
ctgatcgact tcatcgttct gtctggtaac agcagcaaac tgtggctgtt cccgatcgtc   1080
ggtatcggtt atgcgattgt ttactacacc atcttccgcg tgctgattaa agcactggat   1140
```

```
ctgaaaacgc cgggtcgtga agacgcgact gaagatgcaa aagcgacagg taccagcgaa   1200
atggcaccgg ctctggttgc tgcatttggt ggtaaagaaa acattactaa cctcgacgca   1260
tgtattaccc gtctgcgcgt cagcgttgct gatgtgtcta aagtggatca ggccggcctg   1320
aagaaactgg gcgcagcggg cgtagtggtt gctggttctg tgttcaggc gattttcggt   1380 actaaatccg ataacctgaa aaccgagatg gatgagtaca tccgtaacca ctaa         1434

<210> SEQ ID NO 76
<211> LENGTH: 510
<212> TYPE: DNA
<213> ORGANISM: Escherichia coli

<400> SEQUENCE: 76
atgggtttgt tcgataaact gaaatctctg gtttccgacg acaagaagga taccggaact     60
attgagatca ttgctccgct ctctggcgag atcgtcaata tcgaagacgt gccggatgtc    120 gttttttgcgg aaaaaatcgt tggtgatggt attgctatca aaccaacggg taacaaaatg    180
gtcgcgccag tagacggcac cattggtaaa atctttgaaa ccaaccacgc attctctatc    240
gaatctgata gcggcgttga actgttcgtc cacttcggta tcgacaccgt tgaactgaaa    300
ggcgaaggct tcaagcgtat tgctgaagaa ggtcagcgcg tgaaagttgg cgatactgtc    360
attgaatttg atctgccgct gctggaagag aaagccaagt ctaccctgac tccggttgtt    420
atctccaaca tggacgaaat caagaactg atcaaactgt ccggtagcgt aaccgtgggt    480
gaaaccccgg ttatccgcat caagaagtaa                                      510

<210> SEQ ID NO 77
<211> LENGTH: 258
<212> TYPE: DNA
<213> ORGANISM: Escherichia coli

<400> SEQUENCE: 77
atgttccagc aagaagttac cattaccgct ccgaacggtc tgcacacccg ccctgctgcc     60
cagtttgtaa agaagctaa gggcttcact tctgaaatta ctgtgacttc caacggcaaa    120
agcgccagcg cgaaaagcct gtttaaactg cagactctgg gcctgactca aggtaccgtt    180
gtgactatct ccgcagaagg cgaagacgag cagaaagcgg ttgaacatct ggttaaactg    240
atggcggaac tcgagtaa                                                   258

<210> SEQ ID NO 78
<211> LENGTH: 1254
<212> TYPE: DNA
<213> ORGANISM: Escherichia coli

<400> SEQUENCE: 78
atgtactatt taaaaacac aaacttttgg atgttcggtt tattcttttt cttttacttt      60
tttatcatgg gagcctactt cccgtttttc ccgatttggc tacatgacat caaccatatc    120
agcaaaagtg atacgggtat tatttttgcc gctatttctc tgttctcgct attattccaa    180
ccgctgtttg gtctgctttc tgacaaactc gggctgcgca aatacctgct gtggattatt    240
accggcatgt tagtgatgtt tgcgccgttc tttattttta tcttcgggcc actgttacaa    300
tacaacattt tagtaggatc gattgttggt ggtatttatc taggcttttg ttttaacgcc    360
ggtgcgccag cagtagaggc atttattgag aaagtcagcc gtcgcagtaa tttcgaattt    420
ggtcgcgcgc ggatgtttgg ctgtgttggc tgggcgctgt gtgcctcgat tgtcggcatc    480
```

```
atgttcacca tcaataatca gtttgttttc tggctgggct ctggctgtgc actcatcctc    540
gccgttttac tcttttttcgc caaaacggat gcgccctctt ctgccacggt tgccaatgcg    600
gtaggtgcca accattcggc atttagcctt aagctggcac tggaactgtt cagacagcca    660
aaactgtggt ttttgtcact gtatgttatt ggcgtttcct gcacctacga tgtttttgac    720
caacagtttg ctaatttctt tacttcgttc tttgctaccg gtgaacaggg tacgcgggta    780
tttggctacg taacgacaat gggcgaatta cttaacgcct cgattatgtt ctttgcgcca    840
ctgatcatta atcgcatcgg tgggaaaaac gccctgctgc tggctggcac tattatgtct    900
gtacgtatta ttggctcatc gttcgccacc tcagcgctgg aagtggttat tctgaaaacg    960
ctgcatatgt ttgaagtacc gttcctgctg gtgggctgct taaatatat taccagccag   1020
tttgaagtgc gttttttcagc gacgatttat ctggtctgtt tctgcttctt taagcaactg   1080
gcgatgattt ttatgtctgt actggcgggc aatatgtatg aaagcatcgg tttccagggc   1140
gcttatctgg tgctgggtct ggtggcgctg ggcttcacct taatttccgt gttcacgctt   1200
agcggccccg gcccgctttc cctgctgcgt cgtcaggtga atgaagtcgc ttaa            1254

<210> SEQ ID NO 79
<211> LENGTH: 1545
<212> TYPE: DNA
<213> ORGANISM: Escherichia coli

<400> SEQUENCE: 79
atggatgtca ttaaaaagaa acattggtgg caaagcgacg cgctgaaatg gtcagtgcta     60
ggtctgctcg gcctgctggt gggttacctt gttgttttaa tgtacgcaca aggggaatac   120
ctgttcgcca ttaccacgct gatattgagt tcagcggggc tgtatatttt cgccaatcgt   180
aaagcctacg cctggcgcta tgtttacccg gaatggctg gaatgggatt attcgtcctc    240
ttccctctgg tctgcaccat cgccattgcc ttcaccaact acagcagcac taaccagctg   300
acttttgaac gtgcgcagga agtgttgtta gatcgctcct ggcaagcagg caaaaccctat   360
aactttggtc tttacccggc gggcgatgag tggcaactgg cgctcagcga cggcgaaacc   420
ggcaaaaatt acctctccga cgcttttaaa tttggcggcg agcaaaaact gcaactgaaa   480
gaaacgaccg cccagcccga aggcgaacgc gcgaatctgc gcgtgattac ccagaatcgt   540
caggcgctga gtgacattac cgccattctg ccggatggca acaaagtgat gatgagctcc   600
ctgcgccagt tttctggcac gcagccgctc tacacactcg acggtgacgg cacgttgacg   660
aataatcaga gcggcgtgaa atatcgtccg aataaccaaa ttggcttttta ccagtccatt   720
accgccgacg gcaactgggg tgatgaaaag ctaagccccg ttacaccgt gaccaccggc   780
tggaaaaact ttacccgcgt ctttaccgac gaaggcattc agaaaccgtt cctcgccatt   840
ttcgtctgga ccgtggtgtt ctcgctgatc actgtctttt taacggtggc ggtcggcatg   900
gttctggcgt gtctggtgca gtgggaagcg ttgcgcggca agcggtcta tcgcgtcctg   960
ctgattctgc cctacgcggt gcatcgttc atttcaatct tgattttcaa agggttgttt   1020
aaccagagct tcggtgaaat caacatgatg ttgagcgcgc tgtttggcgt gaagcccgcc   1080
tggttcagcg atccgaccac cgccgcacg atgctaatta tcgtcaatac ctggctgggt   1140
tatccgtaca tgatgatcct ctgcatgggc ttgctgaaag cgattccgga cgatttgtat   1200
gaagcctcag caatggatgg cgcaggtccg ttccagaact tctttaagat tacgctgccg   1260
ctgctgatta aaccgctgac gccgctgatg atcgccagct tcgcctttaa ctttaacaac   1320
ttcgtgctga ttcaactgtt aaccaacggc ggcccggatc gtcttggcac gaccacgcca   1380
```

| | |
|---|---|
| gccggttata ccgacctgct tgttaactac acctaccgca tcgcttttga aggcggcggg | 1440 |
| ggtcaggact tcggtctggc ggcagcaatt gccacgctga tcttcctgct ggtgggtgcg | 1500 |
| ctggcgatag tgaacctgaa agccacgcga atgaagtttg attaa | 1545 |

<210> SEQ ID NO 80
<211> LENGTH: 891
<212> TYPE: DNA
<213> ORGANISM: Escherichia coli

<400> SEQUENCE: 80

| | |
|---|---|
| atggcaatgg tccaaccgaa atcgcaaaaa gctcgtttat ttattactca cctgctactg | 60 |
| ctacttttta tcgcagcgat tatgttcccg ctgctgatgg tcgtcgctat ctcgctgcgt | 120 |
| cagggaaact ttgcgaccgg cagcctgatc ccggagcaaa tctcctggga tcactggaaa | 180 |
| ctggcgttag tttttagcgt tgaacaggct gatggtcgca ttacgccacc gccattcccg | 240 |
| gtactgctgt ggctgtggaa ctcggtaaag gtcgccggga tttccgcgat ggcattgtg | 300 |
| gcgctctcca ccacctgcgc ctacgctttc gcccgtatgc gctttccagg caaagcgacg | 360 |
| ctgctgaaag gaatgctgat tttccagatg ttcccggcag tactttcact ggtcgcgttg | 420 |
| tatgcgttgt ttgatcgtct gggtgagtac attccattca ttggcctgaa tactcacggc | 480 |
| ggcgtaattt tcgcgtatct gggtgggatt gcgctgcatg tctggaccat caaaggctat | 540 |
| ttcgaaacca tcgacagttc gctggaagaa gctgctgcgc tggatggtgc gacaccgtgg | 600 |
| caggccttcc gccttgtcct gttgccgctg tcagtaccga ttctggcggt ggtattcatc | 660 |
| ctgtcgttta tcgctgccat tactgaagtt ccggtcgcgt cgctgttact gcgtgacgta | 720 |
| aacagctaca ccctggccgt ggggatgcag caatacctca cccgcaaaa ctacctgtgg | 780 |
| ggtgactttg ccgccgctgc cgtgatgtct gcattaccga tcaccatcgt cttcttgctg | 840 |
| gctcaacgct ggctggtcaa cggcctgacg gcaggtggtg tgaaaggtta a | 891 |

<210> SEQ ID NO 81
<211> LENGTH: 6546
<212> TYPE: DNA
<213> ORGANISM: Salmonella typhimurium

<400> SEQUENCE: 81

| | |
|---|---|
| atgaatgcaa aagtttgggt tctgggcgac gcggtggtgg acctgctgcc ggagagcgaa | 60 |
| gggcgcctgc tgcagtgccc tggaggcgcg ccggctaacg tggcggtagg ggttgcccgc | 120 |
| cttggcggca acagcggatt tatcggcgcc gtcggcggtg acccgtttgg ccgctacatg | 180 |
| cgtcataccc tgcaacagga gcaggtcgac gtcagccata tgtatctcga cgatcagcac | 240 |
| cgcacgtcca ctgtggtcgt cgaccttgac gaccagggg aacgcacctt tacctttatg | 300 |
| gtacgcccca gcgcggacct gttcctggtt gaagaagacc tgccacagtt gccgccgga | 360 |
| cagtggttgc acgtctgctc catcgcgctc agcgccgagc ccagccgtag cactaccttc | 420 |
| gcggcgatgg agagcatcag gtctgccggc ggtcgggtca gctttgaccc taatattcgt | 480 |
| cccgatctct ggcaggatca ggcttttgctg ctagcctgcc tcgatcgcgc tttgcacatg | 540 |
| gccaacgtgg taaagctatc ggaagaggag ctggtcttca tcagcagcag taatgattta | 600 |
| gcatacggaa tcgccagcgt aacggagcgc tatcagccag aattgctact ggtgacccgg | 660 |
| ggcaaagcgg gggtgcttgc cgcgtttcag cagaagttta cccatttcaa cgcccggcct | 720 |
| gtggccagcg tggacaccac cggcgcggga gacgcatttg tcgccggact gctcgccagc | 780 |

```
cttgcggcta acgggatgcc aacggacatg accgcactgg aaccgacact cacgcttgca    840
cagacctgcg gcgccctggc caccacagcc aaaggtgcga tgaccgcctt gccttatcag    900
cgcgatctca accgtcagtt ttaatcctta aagccgcttt gcgcggctca ctttgttgca    960
tgcatcacat ttattaaacc ggtttagcat atttgtttta agaaaaacaa aggtcgggct   1020
taacatagcg cctaaaccgg tttagcaaaa attataattt tccattttta cttttgggat   1080
gccaacagca tgtacagaaa aagcacactt gcgatgctta tcgctttgct aaccagcgct   1140
gcctcagccc atgcgcaaac ggatataagc accattgaag cccgactcaa cgcgctggaa   1200
aaacgcctgc aggaggcaga aaacagggcg caaacggcgg aaaaccgcgc cggggcggcg   1260
gagaaaaaag ttcagcaact caccgcgcag cagcaaaaaa accagaactc gactcaggaa   1320
gtggctcagc gtaccgccag acttgagaaa aaagccgatg acaaaagcgg atttgagttt   1380
cacggttacg cccgctccgg cgtgataatg aatgattccg gcgccagcac caaatccgga   1440
gcctacataa cgccggcagg tgaaaccggc ggagctatcg gccgtctggg aaaccaggcc   1500
gataccctatg ttgaaatgaa tcttgaacat aagcagaccc tggataatgg ggccacgacc   1560
cgctttaagg tgatggtcgc cgacgggcaa acctcttata cgactggac tgcaagcacc    1620
agcgatctga acgttcgtca ggcctttgtc gaattgggta acctgccgac gttcgctggg   1680
ccatttaagg gctccaccct gtgggccggg aaacgtttcg accgcgacaa tttcgatatt   1740
cactggattg actctgatgt cgtgttcctc gccggtaccg tggtggtat ctatgacgtg    1800
aagtggaacg acggcctgcg gagtaatttc tccctgtacg ggcgtaactt cggcgacatt   1860
gatgattcca gcaacagcgt gcagaactat atcctcacca tgaatcactt cgcaggtccg   1920
ctgcagatga tggtcagcgg tctgcggggcg aaggataacg acgagcgtaa agatagcaac   1980
ggcaatctgg caaaaggcga tgcggcaaac accggcgtgc atgcgctgct cggcctgcat   2040
aacgacagtt tctacggcct gcgcgacggt agcagtaaaa ccgctctgct ttatggtcat   2100
ggtctgggcg cagaggttaa aggtatcgga tctgatggcg cacttcgtcc gggagccgac   2160
acatggcgca ttgccagtta cggcaccacg ccgctcagcg aaaactggtc tgttgccccg   2220
gcaatgctgg cgcaacgcag taaagaccgc tatgccgatg cgacagcta tcagtgggca    2280
acattcaacc tgcgtctgat tcaggcaatc aatcagaatt cgctctcgc ctacgaaggc    2340
agctaccagt acatggatct taaacccgaa ggttataacg atcgtcaggc ggtgaacggt   2400
agcttctaca agctcacctt cgccccgaca tttaaggtcg gcagtatcgg tgatttcttc   2460
agtcgcccgg agattcgttt ctataccctcc tggatggact ggagcaaaaa actgaataat    2520
tacgccagcg acgacgccct gggcagtgac ggttttaact cgggcggcga atggtctttc   2580
ggtgtgcaga tggaaacctg gttctgacgc ttacgcctga tgcaggaat agccgggggt    2640
cagagcatct ttgtcacccc ggactcaact aagacgcaga aaaagcgctc ccgtgaacgc   2700
gggacgacaa cataaaaatg tttaagcctt aagagggtac tatggatttt gaacagattt   2760
cctgctcgct gcttccgctt cttggaggca agaaaatat cgccagcgcc gcgcactgcg    2820
ccacgcgcct gcgcctggtg ctggtcgatg attcgctggc cgaccagcag gccatcggca   2880
aagttgaagg ggtgaaggc tgtttttcgta atgccggaca gatgcagatt attttcggca    2940
ccggggtggt aaataaggtc tacgctgcct ttactcaggc ggcgggtatt agcgaatcca   3000
gcaaatcgga agccgccgac atcgcggcaa aaagctcaa tccgttccag cgcatcgccc    3060
gcctgctatc aaacatcttc gtgccgataa tccctgccat cgtcgcctct ggtctgctga   3120
tgggcctgct gggaatggtc aaaacatacg gctgggttga cccgggcaac gccatctaca   3180
```

```
tcatgctgga tatgtgcagc tcggcggcat ttatcattct gccgattctg attggctta    3240
ccgccgcccg cgaattcggc ggtaatcctt atctcggcgc gacgcttggc ggcattctga    3300
ctcatccagc gctgactaac gcctggggcg tggccgcggg tttccacacc atgaactttt    3360
tcggcttcga aattgccatg atcggctatc agggtacggt gttcccggta ctgctggcag    3420
tatggtttat gagcatcgtt gagaagcagt tgcgtcgcgc aatccccgat gccctggatt    3480
tgatcctgac gccgttcctg acggtgatta tatccggttt tatcgccctg ttgattatcg    3540
gcccggccgg tcgcgcactg ggcgacggta tctcgtttgt cctcagcacc ctgattagcc    3600
acgccggctg gctcgccggg ttactgtttg gcggtctcta ttcagttatc gtcattaccg    3660
gtattcatca cagcttccat gcggttgaag ccgggttgct gggcaatccc tccatcggcg    3720
tcaacttcct gctgccgatt tgggcgatgg ccaacgtcgc tcagggcgga gcctgtctgg    3780
cggtgtggtt caaaaccaaa gatgcaaaaa ttaaagccat tactctgccc tcggcgtttt    3840
ccgccatgct gggcatcacc gaggcggcga tttttggtat taacctgcgc tttgtgaagc    3900
catttattgc ggcgctgatt ggtggtgcgg cgggcggcgc atgggtggta tctgtacacg    3960
tctacatgac cgcggtcggc ttgacagcga tccccggcat ggccatcgtg caggccagtt    4020
cgctgttgaa ctacattatc gggatggtta tcgccttttgg cgtcgccttt acggtctccc    4080
tggttttgaa atacaaaacg gacgctgaat aatgtctctt ccatcacgac tgcctgcgat    4140
tttgcaggcc gtaatgcagg gccagccgcg cgcgctggcc gatagccact atccgcgctg    4200
gcaccatgcg ccggtcaccg ggctgatgaa cgaccccaac ggctttatcg aatttgccgg    4260
acgctatcat ctgtttttatc agtggaaccc gctcgcctgc gatcatacgt ttaagtgctg    4320
ggcgcactgg agttccatcg atctgctgca ctggcagcat gagcccattg cgctgatgcc    4380
ggacgaagag tatgaccgta acggctgcta ctccggcagc gcggtggata caacggtac    4440
gcttaccctg tgctataccg gcaacgtgaa gtttgccgag ggagggcgaa ccgcctggca    4500
atgcctggca acgaaaaacg ctgacggcac cttccgcaaa atcggtccgg tcctgccgct    4560
gccggagggc tacaccggcc acgtgcgcga cccaaaagtc tggcgacacg aagacctgtg    4620
gtacatggtg ctgggcgcgc aggatcggca aaagcgcggc aaggtgctgc tgttcagctc    4680
tgcggatctc catcagtgga cgagtatggg tgaaatcgcc ggccacggca tcaatggcct    4740
cgacgacgtc ggctatatgt gggagtgccc ggatcttttt ccactcggcg accagcatat    4800
tctaatctgc tgtccgcagg ggattgcccg tgaggaagag tgctacctga cacctaccc    4860
ggcagtatgg atggcgggcg agtttgatta cgctgctggc gctttcagac acggcgaact    4920
gcacgaactg gacgccgggt ttgagttcta cgccccgcaa accatgctta ccagtgatgg    4980
ccgtcgtctg ctggtcggct ggatgggcgt gccggagggc gaagagatgc ttcagccgac    5040
cctgaacaac ggctggatcc atcagatgac ctgcctgcgt gagctggagt ttatcaacgg    5100
tcagctctat cagcgtccgc tacgggaact gagcgccctg cgcggtgaag cgaacgctg    5160
gtcggggaac gccctgccgc tggcaccgat ggaaatcgat ttgcaaaccc gcggggggcga    5220
tatgttgagc ctcgattttg gcggcgtatt aacccttgag tgcgatgcca gcggactccg    5280
cctggcccga cgcagtctcg ccagtgacga gatgcattat cgttactggc gcggaaacgt    5340
ccgctcgctg cgtgttttca tcgaccagtc gagcgtggag attttcataa acggcggtga    5400
aggggtgatg agcagccgct acttcccggc ctgctccggt cagctaacat tctccggcat    5460
cacgccggac gcattctgct actggccgct gcgaacttgc atggtagaat aagcgtttg    5520
```

-continued

| | |
|---|---|
| cttcaggctc atggcgtcgt aatgaaaacc aaacgcgtaa ccattaaaga tatagccgaa | 5580 |
| caggctggcg tctccaaagc gaccgccagc ttggtactga atggtcgtgg caaggagctg | 5640 |
| cgcgtggcgc aggaaacgcg tgagcgcgta ctgtcgattg cccgtaagca tcactatcag | 5700 |
| ccaagcattc atgcccgctc gctgcgcaac aaccgcagcc acaccatcgg ctggtggtg | 5760 |
| ccggagatca ccaaccacgg ctttgcggtc tttgcccatg agctggagat gctgtgccgc | 5820 |
| gaggcgggcg tccagctgtt gatctcttgt actgatgaaa accccggtca ggagagcgtg | 5880 |
| gtggtcaata atatgattgc cgccaggtc gacgggatga tcgtcgcttc ctgtatgcac | 5940 |
| aacgatgccg actatctcaa actcagccaa cagctgccag tggtgctgtt tgaccggtgc | 6000 |
| cccaatgaaa gcgcgctgcc gctggtaatg accgattcga ttaccccaac ggcggaactg | 6060 |
| atttcccgca tcgcgcctca gcatagcgat gagttctggt ttttaggcgg tcaggcgcgt | 6120 |
| ctgtcgccct cccgcgatcg tctgaccggg ttcacgcagg gtttggctca ggcgggtatt | 6180 |
| gccctgcgcc cggaatgggt gatcaacggc aattaccacc ccagctccgg ctatgagatg | 6240 |
| tttgccgcac tctgcgcgcg ccttgggcgg ccgcctaagg cgctattcac cgccgcctgc | 6300 |
| gggctgctcg aaggggttct gcgctatatg agccagcacc atttactcga ttccgatatt | 6360 |
| catctgacga gctttgacga tcactatctt tatgattcgc tgtcgctgcg tatcgacact | 6420 |
| gtccagcagg ataatcgcca gctggcctgg cactgctacg atctgataag ccagctgatc | 6480 |
| gagggcgata cgcccgaaac gctacaacgc tacctgcccg caaccctgca gtttcggcat | 6540 |
| cagtaa | 6546 |

<210> SEQ ID NO 82
<211> LENGTH: 4885
<212> TYPE: DNA
<213> ORGANISM: Escherichia coli

<400> SEQUENCE: 82

| | |
|---|---|
| ctatattgct gaaggtacag gcgtttccat aactatttgc tcgcgttttt tactcaggaa | 60 |
| gaaaatgcca aatagcaaca tcaggcagac aatacccgaa attgcgaaga aaactgtctg | 120 |
| gtagcctgcg tggtcaaaga gtatcccagt cggcgttgaa agcagcacaa tcccaagcga | 180 |
| actggcaatt tgaaaaccaa tcagaaagat cgtcgacgac aggcgcttat caaagtttgc | 240 |
| cacgctgtat ttgaagacgg atatgacaca aagtggaacc tcaatggcat gtaacagctt | 300 |
| cactaatgaa ataatccagg ggttaacgaa caacgcgcag gaaaggatac gcaacgccat | 360 |
| aatcacaaca ccgataagta atgcatttt tggccctacc cgattcacaa agaaaggaat | 420 |
| aatcgccatg cacagcgctt cgagtaccac ctggaatgag ttgagataac catacaggcg | 480 |
| cgttcctaca tcgtgtgatt cgaataaacc tgcataaaag acaggaaaga gttgttgatc | 540 |
| aaaaatgtta tagaaagacc acgtccccac aataaatatg acgaaaaccc agaagtttcg | 600 |
| atccttgaaa actgcgataa aatcctcttt ttttaccccct cccgcatccg ccgctatgca | 660 |
| ctggtgatcc ttatctttaa aacgcatgtt gatcatcata aatacagcgc caaatagcga | 720 |
| gaccaaccag aagttgatat ggggactgat actaaaaaat ataccggcaa agaacgcgcc | 780 |
| aatagcatag ccaaaagatc cccaggcgcg cgctgttcca tattcgaaat gaaaatttcg | 840 |
| cgccattttt tcggtgaagc tgtcaagcaa accgcatccc gccagatacc ccaggccaaa | 900 |
| aaagagcgcc cccagaatta gacctacaga aaaattgctt tgcagtaacg gttcataaac | 960 |
| gtaaatcata acggtccgg tcaagaccag aatgaaactc atacaccaga tgagcggttt | 1020 |
| cttcagaccg agtttatcct gaacgatgcc gtagaacatc ataaatagaa tgctggtaaa | 1080 |

```
ctggttgacc gaataaagtg tacctaattc cgtccctgtt aatcctagat gtcctttcag   1140
ccaaatagcg tataacgacc accacagcga ccaggaaata aaaagagaa atgagtaact    1200 ggatgcaaaa cgatagtacg catttctgaa tggaatattc agtgccataa ttacctgcct   1260
gtcgttaaaa aattcatgtc ctatttagag ataagagcgg cctcgccgtt tacttctcac   1320
tttccagttc ttgtcgacat ggcagcgctg tcattgcccc tttcgctgtt actgcaagcg   1380
ctccgcaacg ttgagcgaga tcgataattc gtcgcatttc tctctcatct gtagataatc   1440
ccgtagagga cagacctgtg agtaacccgg caacgaacgc atctcccgcc ccagtgctat   1500
cgacacaatt cacagacatt ccagcaaaat ggtggacttg tcctcgataa cagaccacca   1560
ccccttctgc acctttagtc accaacagca tggcgatctc atactctttt gccagggcgc   1620
atatatcccg atcgttctgt gttttttccac tgataagtcg ccattcttct tccgagagct   1680
tgacgacatc cgccagttgt agcgcctgcc gcaaacacaa gcggagcaaa tgctcgtctt   1740
gccatagatc ttcacgaata ttgggatcga agctgacaaa acctccggca tgccggatcg   1800
ccgtcatcgc agtaaatgcg ctggtacgcg aaggctcggc agacaacgca attgaacaga   1860
gatgtaacca ttcgccatgt cgccagcagg gcaagtctgt cgtctctaaa aaagatcgg    1920 cactggggcg gaccataaac gtaaatgaac gttctccttg atcgttcaga tcgacaagca   1980
ccgtggatgt ccggtgccat tcatcttgct tcagatacgt gatatcgaca ccctcagtta   2040
gcagcgttct ttgcattaac gcaccaaaag gatcatcacc gacccgacct ataaacccac   2100
ttgttccgcc taatctggcg attcccaccg caacgttagc tggcgcgccg ccaggacaag   2160
gcagtagccg cccgtctgat tctggcaaga gatctacgac cgcatcccct aaaacccata   2220
ctttggctga cattttttc ccttaaattc atctgactta cgcatagtga taaacctctt    2280
tttcgcaaaa tcgtcatgga tttactaaaa catgcatatt cgatcacaaa acgtcatagt   2340
taacgttaac atttgtgata ttcatcgcat ttatgaaagt aagggacttt attttataa    2400 aagttaacgt taacaattca ccaaatttgc ttaaccagga tgattaaaat gacgcaatct   2460
cgattgcatg cggcgcaaaa cgcactagca aaacttcacg agcgccgagg taacactttc   2520
tatccccatt ttcacctcgc gcctcctgcc gggtggatga acgatccaaa cggcctgatc   2580
tggtttaacg atcgttatca cgcgttttat caacatcacc cgatgagcga acactggggg   2640
ccaatgcact ggggacatgc caccagcgac gatatgatcc actggcagca tgagcctatt   2700
gcgctagcgc caggagacga gaatgacaaa gacgggtgtt tttcaggtag tgctgtcgat   2760
gacaatggtg tcctctcact tatctacacc ggacacgtct ggctcgatgg tgcaggtaat   2820
gacgatgcaa ttcgcgaagt acaatgtctg gctaccagtc gggatggtat tcatttcgag   2880
aaacagggtg tgatcctcac tccaccagaa ggcatcatgc acttccgcga tcctaaagtg   2940
tggcgtgaag ccgacacatg gtggatggta gtcgggggcga aagacccagg caacacgggg   3000
cagatcctgc tttatcgcgg cagttcattg cgtgaatgga ctttcgatcg cgtactggcc   3060
cacgctgatg cgggtgaaag ctatatgtgg gaatgtccgg acttttttcag ccttggcgat   3120 cagcattatc tgatgttttc cccgcaggga atgaatgccg agggatacag ttatcgaaat   3180
cgctttcaaa gtggcgtaat acccggaatg tggtcgccag gacgactttt tgcacaatcc   3240
gggcatttta ctgaacttga taacgggcat gactttatg caccacaaag ctttgtagcg    3300
aaggatggtc ggcgtattgt tatcggctgg atggatatgt gggaatcgcc aatgccctca   3360
aaacgtgaag gctgggcagg ctgcatgacg ctggcgcgcg agctatcaga gagcaatggc   3420
```

```
aaactcctac aacgcccggt acacgaagct gagtcgttac gccagcagca tcaatctatc    3480
tctccccgca caatcagcaa taaatatgtt ttgcaggaaa acgcgcaagc agttgagatt    3540
cagttgcagt gggcgctgaa gaacagtgat gccgaacatt acggattaca gctcggcgct    3600
ggaatgcggc tgtatattga taaccaatct gagcgacttg ttttgtggcg gtattaccca    3660
cacgagaatt tagatggcta ccgtagtatt cccctcccgc agggtgacat gctcgcccta    3720
aggatattta tcgatacatc atccgtggaa gtatttatta acgacgggga ggcggtgatg    3780
agtagccgaa tatatccgca gccagaagaa cgggaactgt cgctctatgc ctcccacgga    3840
gtggctgtgc tgcaacatgg agcactctgg caactgggtt aacataatat caggtggaac    3900
aacggatcaa cagcgggcaa gggatccgcg tcactcttcc cccttcacga ccttcaataa    3960
tatgcaatgc agcttcccgc ccgataatgt catgtggaag ctgaattgtg gtcagcggcg    4020
gtaaaaacag atgcccgacg ccaaccagat tatcaaagcc cattacggcg acatcctgcg    4080
ggatacgtac ccccttcgcc aaaagaacct gataagccac aaaggctgcg cgatcgttac    4140
cacatatcag aacatcaaaa tctggttttgc ccgatttgaa gtgggcattg agtaaacttg    4200
cgagatcggt gtagtgatca tcacctgttg ccatgtgaaa ttgtttcacc tcagccagat    4260
ctcgtccagc atcacgccag gcctgctcaa atccctgccg acgataccct gttgccaacg    4320
cactttccgg tagccagaag cataacggtt gacgatagcc cgccgcgagc aaatgctgtg    4380
ttgattcata ttgtgcagtg taatcatcag ggatataact gggtaacgct gggtcatccg    4440
ccacacagtt cgccaataca atattttcac catacagaga ctcaggcagc gtgatatgtc    4500
gcagccccat tgtagtatag ataatgccat ccggacggtg ggcaagcagc tgacgtgccg    4560
cgcgggcagc gtcatcttca gaaaaaatat tgattaaaaa actattccag ccgaactcgc    4620
tggcggtttg ctcaatggca agcagaatat caacagagaa aggagtggta gcagtgtcct    4680
gcgccagcac ggcgagagtc gacggcttac gtccttgagc gcgcatctta cgggcggaaa    4740
gatcaggaac ataattcagg gtctggattg cctgcaatac gcggtcacgc gttgcaggac    4800
gcacagattc tgcattatgc atcacccggg agactgtcat catcgacact cccgccaggc    4860
gtgcgacatc ctttaatgaa gccat                                         4885

<210> SEQ ID NO 83
<211> LENGTH: 3771
<212> TYPE: DNA
<213> ORGANISM: Escherichia coli

<400> SEQUENCE: 83
atgaaaataa agaacattct actcacccctt tgcacctcac tcctgcttac caacgttgct      60
gcacacgcca aagaagtcaa aataggtatg gcgattgatg atctccgtct tgaacgctgg     120
caaaaagatc gagatatctt tgtgaaaaag gcagaatctc tcggcgcgaa agtatttgta     180
cagtctgcaa atggcaatga agaaacacaa atgtcgcaga ttgaaaacat gataaaccgg     240
ggtgtcgatg ttcttgtcat tattccgtat aacggtcagg tattaagtaa cgttgtaaaa     300
gaagccaaac aagaaggcat taaagtatta gcttacgacc gtatgattaa cgatgcggat     360 atcgatttttt atatttcttt cgataacgaa aaagtcggtg aactgcaggc aaaagccctg     420
gtcgatattg ttccgcaagg taattacttc ctgatgggcg gctcgccggt agataacaac     480
gccaagctgt tccgcgccgg acaaatgaaa gtgttaaaac cttacgttga ttccggaaaa     540
attaaagtcg ttggtgacca atgggttgat ggctggttac cggaaaacgc attgaaaatt     600
atggaaaacg cgctaaccgc caataataac aaaattgatg ctgtagttgc ctcaaacgat     660
```

```
gccaccgcag gtggggcaat tcaggcatta agcgcgcaag gtttatcagg gaaagtagca    720
atctccggcc aggatgcgga tctcgcaggt attaaacgta ttgctgccgg tacgcaaact    780
atgacggtgt ataaacctat tacgttgttg gcaaatactg ccgcagaaat tgccgttgag    840
ttgggcaatg tcaggaacc aaaagcagat accacactga ataatggcct gaaagatgtc    900
ccctcccgcc tcctgacacc gatcgatgtg aataaaaaca acatcaaaga tacggtaatt    960
aaagacggat tccacaaaga gagcgagctg taagcgttac gccccagcgc ggagcggggg   1020
cgtgatttct ctccatgccg cgtgaatgaa ttggcttagg tggagtcgtt atgccttatc   1080
tacttgaaat gaagaacatt accaaaacct tcggcagtgt gaaggcgatt gataacgtct   1140
gcttgcggtt gaatgctggc gaaatcgtct cactttgtgg ggaaaatggg tctggtaaat   1200
caacgctgat gaaagtgctg tgtggtattt atccccatgg ctcctacgaa ggcgaaatta   1260
tttttgcggg agaagagatt caggcgagtc acatccgcga taccgaacgc aaaggtatcg   1320
ccatcattca tcaggaattg gccctggtga agaattgac cgtgctggaa aatatcttcc   1380
tgggtaacga ataacccac aatggcatta tggattatga cctgatgacg ctacgctgtc   1440
agaagctgct cgcacaggtc agtttatcca tttcacctga tacccgcgtt ggcgatttag   1500
ggcttgggca acaacaactg gttgaaattg ccaaggcact taataaacag gtgcgcttgt   1560
taattctcga tgaaccgaca gcctcattaa ctgagcagga aacgtcgatt ttactggata   1620
ttattcgcga tctacaacag cacggtatcg cctgtattta tatttcgcac aaactcaacg   1680
aagtcaaagc gatttccgat acgatttgcg ttattcgcga cggacagcac attggtacgc   1740
gtgatgctgc cggaatgagt gaagacgata ttatcaccat gatggtcggg cgagagttaa   1800
ccgcgcttta ccctaatgaa ccacatacca ccggagatga atattacgt attgaacatc   1860 tgacggcatg gcatccggtt aatcgtcata ttaaacgagt taatgatgtc tcgttttccc   1920
tgaaacgtgg cgaaatattg ggtattgccg gactcgttgg tgccggacgt accgagacca   1980
ttcagtgcct gtttggtgtg tggcccggac aatgggaagg aaaaatttat attgatggca   2040
aacaggtaga tattcgtaac tgtcagcaag ccatcgccca ggggattgcg atggtccccg   2100
aagacagaaa gcgcgacggc atcgttccgg taatggcggt tggtaaaaat attaccctcg   2160
ccgcactcaa taaatttacc ggtggcatta gccagcttga tgacgcggca gagcaaaaat   2220
gtattctgga atcaatccag caactcaaag ttaaaacgtc gtcccccgac cttgctattg   2280
gacgtttgag cggcggcaat cagcaaaaag cgatcctcgc tcgctgtctg ttacttaacc   2340
cgcgcattct cattcttgat gaacccacca ggggtatcga tattggcgcg aaatacgaga   2400
tctacaaatt aattaaccaa ctcgtccagc agggtattgc cgttattgtc atctcttccg   2460
aattacctga agtgctcggc cttagcgatc gtgtactggt gatgcatgaa gggaaactaa   2520
aagccaacct gataaatcat aacctgactc aggagcaggt gatggaagcc gcattgagga   2580
gcgaacatca tgtcgaaaag caatccgtct gaagtgaaat tggccgtacc gacatccggt   2640
ggcttctccg ggctgaaatc actgaatttg caggtcttcg tgatgattgc agctatcatc   2700
gcaatcatgc tgttctttac ctggaccacc gatggtgcct acttaagcgc ccgtaacgtc   2760
tccaacctgt tacgccagac cgcgattacc ggcatcctcg cggtaggaat ggtgttcgtc   2820
ataatttctg ctgaaatcga cctttccgtc ggctcaatga tggggctgtt aggtggcgtc   2880
gcggcgattt gtgacgtctg gttaggctgg ccttttgccac ttaccatcat tgtgacgctg   2940
gttctgggac tgcttctcgg tgcctggaac ggatggtggg tcgcgtaccg taaagtccct   3000
```

```
tcatttattg tcaccctcgc gggcatgttg gcatttcgcg gcatactcat ggcatcacc      3060 aacggcacga ctgtatcccc caccagcgcc gcgatgtcac aaattgggca aagctatctc     3120
cccgccagta ccggcttcat cattggcgcg cttggcttaa tggcttttgt tggttggcaa     3180
tggcgcggaa gaatgcgccg tcaggctttg ggtttacagt ctccggcctc taccgcagta     3240
gtcggtcgcc aggctttaac cgctatcatc gtattaggcg caatctggct gttgaatgat     3300
taccgtggcg ttcccactcc tgttctgctg ctgacgttgc tgttactcgg cggaatgttt     3360
atggcaacgc ggacggcatt tggacgacgc atttatgcca tcggcggcaa tctggaagca     3420
gcacgtctct ccgggattaa cgttgaacgc accaaacttg ccgtgttcgc gattaacgga     3480
ttaatggtag ccatcgccgg attaatcctt agttctcgac ttggcgctgg ttcaccttct     3540 gcggaaata tcgccgaact ggacgcaatt gcagcatgcg tgattggcgg caccagcctg      3600
gctggcggtg tgggaagcgt tgccggagca gtaatggggg catttatcat ggcttcactg     3660
gataacggca tgagtatgat ggatgtaccg accttctggc agtatatcgt taaaggtgcg     3720
attctgttgc tggcagtatg gatggactcc gcaaccaaac gccgttcttg a              3771

<210> SEQ ID NO 84
<211> LENGTH: 1395
<212> TYPE: DNA
<213> ORGANISM: Escherichia coli

<400> SEQUENCE: 84
atgcctgacg ctaaaaaaca ggggcggtca acaaggcaa tgacgttttt cgtctgcttc         60
cttgccgctc tggcgggatt actctttggc ctggatatcg gtgtaattgc tggcgcactg      120
ccgtttattg cagatgaatt ccagattact tcgcacacgc aagaatgggt cgtaagctcc      180
atgatgttcg gtgcggcagt cggtgcggtg ggcagcggct ggctctcctt taaactcggg     240
cgcaaaaaga gcctgatgat cggcgcaatt ttgtttgttg ccggttcgct gttctctgcg     300
gctgcgccaa cgttgaagt actgattctt tcccgcgttc tactgggct ggcggtgggt        360 gtggcctctt ataccgcacc gctgtacctc tctgaaattg cgccggaaaa aattcgtggc     420
agtatgatct cgatgtatca gttgatgatc actatcggga tcctcggtgc ttatcttcct     480
gataccgcct tcagctacac cggtgcatgg cgctggatgc tgggtgtgat tatcatcccg     540
gcaattttgc tgctgattgg tgtcttcttc ctgccagaca gcccacgttg gtttgccgcc     600
aaacgccgtt ttgttgatgc cgaacgcgtg ctgctacgcc tgcgtgacac cagcgcggaa     660
gcgaaacgcg aactggatga atccgtgaa agtttgcagg ttaaacagag tggctgggcg      720
ctgtttaaag agaacagcaa cttccgccgc gcggtgttcc ttggcgtact gttgcaggta     780
atgcagcaat tcaccgggat gaacgtcatc atgtattacg cgccgaaaat cttcgaactg     840
gcgggttata ccaacactac cgagcaaatg tgggggaccg tgattgtcgg cctgaccaac     900
gtacttgcca cctttatcgc aatcggcctt gttgaccgct ggggacgtaa accaacgcta     960
acgctgggct tcctggtgat ggctgctggc atgggcgtac tcggtacaat gatgcatatc    1020
ggtattcact ctccgtcggc gcagtatttc gccatcgcca tgctgctgat gtttattgtc    1080
ggttttgcca tgagtgccgg tccgctgatt tgggtactgt gctccgaaat tcagccgctg    1140
aaaggccgcg attttggcat cacctgctcc actgccacca actggattgc caacatgatc    1200
gttggcgcaa cgttcctgac catgctcaac acgctgggta acgccaacac cttctgggtg    1260
tatgcggctc tgaacgtact gtttatcctg ctgacattgt ggctggtacc ggaaaccaaa    1320
cacgtttcgc tggaacatat tgaacgtaat ctgatgaaag gtcgtaaact gcgcgaaata    1380
```

```
<210> SEQ ID NO 85
<211> LENGTH: 1422
<212> TYPE: DNA
<213> ORGANISM: Zymomonas mobilis

<400> SEQUENCE: 85
atgagttctg aaagtagtca gggtctagtc acgcgactag ccctaatcgc tgctataggc    60
ggcttgcttt tcggttacga ttcagcggtt atcgctgcaa tcggtacacc ggttgatatc   120
cattttattg cccctcgtca cctgtctgct acggctgcgg cttcccttc tgggatggtc    180 gttgttgctg ttttggtcgg ttgtgttacc ggttctttgc tgtctggctg gattggtatt   240
cgcttcggtc gtcgcggcgg attgttgatg agttccattt gtttcgtcgc cgccggtttt   300
ggtgctgcgt taaccgaaaa attatttgga accggtggtt cggctttaca aatttttgc    360 tttttccggt tcttgccgg tttaggtatc ggtgtcgttt caaccttgac cccaaccta    420 attgctgaaa tcgtccgcc agacaaacgt ggtcagatgg tttctggtca gcagatggcc   480
attgtgacgg gtgctttaac cggttatatc tttacctggt tactggctca tttcggttct   540
atcgattggg ttaatgccag tggttggtgc tggtctccgg cttcagaagg cctgatcggt   600
attgccttct tattgctgct gttaaccgca ccggatacgc cgcattggtt ggtgatgaag   660
ggacgtcatt ccgaggctag caaaatcctt gctcgtctgg aaccgcaagc cgatcctaat   720
ctgacgattc aaaagattaa agctggcttt gataaagcca tggacaaaag cagcgcaggt   780 ttgttttgctt ttggtatcac cgttgttttt gccggtgtat ccgttgctgc cttccagcag   840
ttagtcggta ttaaccgcgt gctgtattat gcaccgcaga tgttccagaa tttaggtttt   900
ggagctgata cggcattatt gcagaccatc tctatcggtg ttgtgaactt catcttcacc   960
atgattgctt cccgtgttgt tgaccgcttc ggccgtaaac ctctgcttat ttggggtgct  1020
ctcggtatgg ctgcaatgat ggctgttta ggctgctgtt tctggttcaa agtcggtggt  1080
gttttgcctt tggcttctgt gcttctttat attgcagtct ttggtatgtc atggggccct  1140
gtctgctggg ttgttctgtc agaaatgttc ccgagttcca tcaagggcgc agctatgcct  1200
atcgctgtta ccggacaatg gttagctaat atcttggtta acttcctgtt taaggttgcc  1260
gatggttctc cagcattgaa tcagactttc aaccacggtt tctcctatct cgttttcgca  1320
gcattaagta tcttaggtgg cttgattgtt gctcgcttcg tgccggaaac caaaggtcgg  1380
agcctggatg aaatcgagga gatgtggcgc tcccagaagt ag                     1422

<210> SEQ ID NO 86
<211> LENGTH: 984
<212> TYPE: DNA
<213> ORGANISM: Zymomonas mobilis

<400> SEQUENCE: 86
atggaaattg ttgcgattga catcggtgga acgcatgcgc gtttctctat tgcggaagta    60
agcaatggtc gggttctttc tcttggagaa gaaacaactt ttaaaacggc agaacatgct   120
agcttgcagt tagcttggga acgtttcggt gaaaaactgg tcgtcctct gccacgtgcc   180 gcagctattg catgggctgg cccggttcat ggtgaagttt taaaacttac caataaccct   240
tgggtattaa gaccagctac tctgaatgaa aagctggaca tcgatacgca tgttctgatc   300
aatgacttcg gcgcggttgc ccacgcggtt gcgcatatgg attcttctta tctggatcat   360
```

```
atttgtggtc ctgatgaagc gcttcctagc gatggtgtta tcactattct tggtccggga    420
acgggcttgg gtgttgccca tctgttgcgg actgaaggcc gttatttcgt catcgaaact    480
gaaggcggtc atatcgactt tgctccgctt gacagacttg aagacaaaat tctggcacgt    540
ttacgtgaac gtttccgccg cgtttctatc gaacgcatta tttctggccc gggtcttggt    600
aatatctacg aagcactggc tgccattgaa ggcgttccgt tcagcttgct ggatgatatt    660
aaattatggc agatggcttt ggaaggtaaa gacaaccttg ctgaagccgc tttggatcgc    720
ttctgcttga gccttggcgc tatcgctggt gatcttgctt tggcacaggg tcgaaccagt    780
gttgttattg gcggtggtgt cggtcttcgt atcgcttccc atttgccaga atctggtttc    840
cgtcagcgct ttgtttcaaa aggacgcttt gaacgcgtca tgtccaagat tccggttaag    900
ttgattactt atccgcagcc tggactgttg ggtgcgcagc tgcctatgcc aacaaatatt    960
ctgaagttga ataatatttt ttaa                                           984

<210> SEQ ID NO 87
<211> LENGTH: 966
<212> TYPE: DNA
<213> ORGANISM: Escherichia coli

<400> SEQUENCE: 87
atgacaaagt atgcattagt cggtgatgtg ggcggcacca acgcacgtct tgctctgtgt     60
gatattgcca gtggtgaaat ctcgcaggct aagacctatt cagggcttga ttaccccagc    120
ctcgaagcgg tcattcgcgt ttatcttgaa gaacataagg tcgaggtgaa agacggctgt    180
attgccatcg cttgcccaat taccggtgac tgggtggcga tgaccaacca tacctgggcg    240
ttctcaattg ccgaaatgaa aagaatctc ggttttagcc atctggaaat tattaacgat    300
tttaccgctg tatcgatggc gatcccgatg ctgaaaaaag agcatctgat tcagtttggt    360
ggcgcagaac cggtcgaagg taagcctatt gcggtttacg gtgccggaac ggggcttggg    420
gttgcgcatc tggtccatgt cgataagcgt tgggtaagct tgccaggcga aggcggtcac    480
gttgattttg cgccgaatag tgaagaagag gccattatcc tcgaaatatt gcgtgcggaa    540
attggtcatg tttcggcgga gcgcgtgctt tctggccctg ggctggtgaa tttgtatcgc    600
gcaattgtga agctgacaa ccgcctgcca gaaaatctca agccaaaaga tattaccgaa    660
cgcgcgctgg ctgacagctg caccgattgc cgccgcgcat tgtcgctgtt ttgcgtcatt    720
atgggccgtt ttggcggcaa tctggcgctc aatctcggga catttggcgg cgtgtttatt    780
gcgggcggta tcgtgccgcg cttccttgag ttcttcaaag cctccggttt ccgtgccgca    840
tttgaagata aagggcgctt taagaatat gtccatgata ttccggtgta tctcatcgtc    900
catgacaatc cgggccttct cggttccggt gcacatttac gccagacctt aggtcacatt    960
ctgtaa                                                              966

<210> SEQ ID NO 88
<211> LENGTH: 2547
<212> TYPE: DNA
<213> ORGANISM: Escherichia coli

<400> SEQUENCE: 88
ttgtacctct atattgagac tctgaaacag agactggatg ccataaatca attgcgtgtg     60
gatcgcgcgc ttgctgctat ggggcctgca ttccaacagg tctacagtct actgccgaca    120
ttgttgcact atcaccatcc gctaatgccg ggttaccttg atggtaacgt tcccaaaggc    180
atttgccttt acacgcctga tgaaactcaa cgccactacc tgaacgagct tgaactgtat    240
```

```
cgtggaatgt cagtacagga tccgccgaaa ggtgagcttc caattactgg tgtatacacc    300
atgggcagca cctcgtccgt agggcaaagt tgttcctctg acctggatat ctgggtctgt    360
catcaatcct ggctcgatag cgaagagcgc caattgctac aacgtaaatg tagcctgctg    420
gaaaactggg ccgcctcgct gggtgtggaa gtcagcttct tcctgattga tgaaaaccgc    480
ttccgtcata atgaaagcgg cagcctgggg ggcgaagatt gtggctccac ccagcatata    540
ctgctgcttg acgaatttta tcgtaccgcc gtgcgtctcg ccgtaagcg tattctgtgg    600
aatatggtgc cgtgcgacga agaagagcat tacgacgact atgtgatgac gctttacgcg    660
cagggcgtgc tgacgccaaa tgaatggctg gatctcggtg gcttaagctc gctttctgct    720
gaagagtact ttggtgccag cctttggcag ctctacaaga gtatcgattc cccatacaaa    780
gcggtactga aaacactgct gctggaagcc tattcctggg aatacccgaa cccacgtctg    840
ctggcgaaag atatcaaaca gcgtttgcac gacggcgaga ttgtatcgtt tggtctcgat    900
ccatactgca tgatgctgga gcgtgttact gaatacctga cggcgattga agattttacc    960
cgtctggatt tagtacgtcg ctgcttctat ttaaaagtgt gcgaaaagct cagccgtgaa   1020
cgcgcctgcg taggctggcg tcgcgcagtg ttgagccagt tagtgagcga gtggggttgg   1080
gacgaagctc gtctggcaat gctcgataac cgcgctaact ggaagattga tcaggtgcgt   1140
gaggcgcaca acgagttgct cgacgcgatg atgcagagct accgtaatct gatccgcttt   1200
gcgcgtcgca ataaccttag cgtctccgcc agtccgcagg atatcggcgt gctgacgcgt   1260
aagctgtatg ccgcgtttga agcattacca ggtaaagtga cgctggtaaa cccgcagatt   1320
tcacccgatc tctcggaacc gaatctgacc tttatttatg tgccgccggg ccgggctaac   1380
cgttcaggtt ggtatctgta taccgcgcg ccaaatattg agtcgatcat cagccatcag   1440
ccgctggaat ataaccgtta cctgaataaa ctggtggcgt gggcatggtt taacggcctg   1500
ctgacctcgc gcacccgttt gtatattaaa ggtaacggca ttgtcgattt gcctaagttg   1560
caggagatgg tcgccgacgt gtcgcaccat ttcccgctgc gcttacctgc accgacaccg   1620
aaggcgctct acagcccgtg tgagatccgc catctggcga ttatcgttaa cctggaatat   1680
gacccgacag cggcgttccg caatcaggtg gtgcatttcg atttccgtaa gctggatgtc   1740
ttcagctttg gcgagaatca aaattgcctg gtaggtagcg ttgacctgct gtaccgcaac   1800
tcgtggaacg aagtgcgtac gctgcacttc aacggcgagc aatcgatgat cgaagccctg   1860
aaaactattc tcggcaaaat gcatcaggac gccgcaccgc cagatagcgt ggaagtcttc   1920
tgttatagcc agcatctgcg cggcttaatt cgtactcgcg tgcagcaact ggtttctgag   1980
tgtattgaat tgcgtctttc cagcacccgc caggaaaccg ggcgtttcaa ggcgctgcgc   2040
gtttctggtc aaacctgggg gttgttcttc gaacgcctga atgtatcggt acagaaactg   2100
gaaaacgcca tcgagtttta tggcgcgatt tcgcataaca aactgcacgg cctgtcagtg   2160
caggttgaaa ccaatcacgt caaattaccg gcggtggtgg acggctttgc cagcgaaggg   2220
atcatccagt tctttttcga agaaacgcaa gacgagaatg ctttaatat ctacattctc   2280
gacgaaagca accgggttga ggtatatcac cactgcgaag cagcaaaga ggagctggta   2340
cgtgacgtca gtcgcttcta ctcgtcatcg catgaccgtt ttacctacgg ctcaagcttc   2400
atcaacttca acctgccgca gttctatcag attgtgaagg ttgatggtcg tgaacaggtg   2460
attccgttcc gcacaaaatc tatcggtaac atgccgcctg ccaatcagga tcacgatacg   2520
ccgctattac agcaatattt ttcgtga                                       2547
```

<210> SEQ ID NO 89
<211> LENGTH: 210
<212> TYPE: PRT
<213> ORGANISM: Escherichia coli

<400> SEQUENCE: 89

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Ser Tyr
50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
            85                  90                  95

Glu Ile Ser Tyr Lys Lys Phe Arg Gln Leu Ile Gln Val Asn Pro Asp
        100                 105                 110

Ile Leu Met Arg Leu Ser Ala Gln Met Ala Arg Arg Leu Gln Val Thr
    115                 120                 125

Ser Glu Lys Val Gly Asn Leu Ala Phe Leu Asp Val Thr Gly Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 90
<211> LENGTH: 210
<212> TYPE: PRT
<213> ORGANISM: artificial
<220> FEATURE:
<223> OTHER INFORMATION: Crp* mutant

<400> SEQUENCE: 90

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys His Glu Glu Gly Lys Glu Met Ile Leu Ser Tyr
50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
            85                  90                  95

Glu Ile Ser Tyr Lys Lys Phe Arg Gln Leu Ile Gln Val Asn Pro Asp

```
                    100                 105                 110
Ile Leu Met Arg Leu Ser Ala Gln Met Ala Arg Arg Leu Gln Val Thr
            115                 120                 125

Ser Glu Lys Val Gly Asn Leu Ala Phe Leu Asp Val Thr Gly Arg Ile
        130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 91
<211> LENGTH: 210
<212> TYPE: PRT
<213> ORGANISM: artificial
<220> FEATURE:
<223> OTHER INFORMATION: Crp* mutant

<400> SEQUENCE: 91

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Phe Tyr
50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
    130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 92
<211> LENGTH: 210
<212> TYPE: PRT
```

<213> ORGANISM: artificial
<220> FEATURE:
<223> OTHER INFORMATION: Crp* mutant

<400> SEQUENCE: 92

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
                20                  25                  30

Gln Gly Glu Lys Ala Glu Thr Leu Tyr Tyr Ile Val Lys Gly Ser Val
            35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
    115                 120                 125

Ser Glu Lys Val Gly Asn Leu Ala Phe Leu Asp Val Thr Asp Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 93
<211> LENGTH: 210
<212> TYPE: PRT
<213> ORGANISM: artificial
<220> FEATURE:
<223> OTHER INFORMATION: Crp* mutant

<400> SEQUENCE: 93

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
                20                  25                  30

Gln Gly Glu Lys Ala Glu Thr Leu Tyr Tyr Ile Val Lys Gly Ser Val
            35                  40                  45

Ala Val Leu Ile Lys Asp Glu Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
115                 120                 125

Ser Glu Lys Val Gly Asn Leu Ala Phe Leu Asp Val Thr Gly Asp Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
            195                 200                 205

Thr Arg
    210

<210> SEQ ID NO 94
<211> LENGTH: 2932
<212> TYPE: DNA
<213> ORGANISM: Escherichia coli

<400> SEQUENCE: 94

```
atgcgaattg gcataccaag agaacggtta accaatgaaa cccgtgttgc agcaacgcca      60
aaaacagtgg aacagctgct gaaactgggt tttaccgtcg cggtagagag cggcgcgggt     120
caactggcaa gttttgacga taaagcgttt gtgcaagcgg cgctgaaat tgtagaaggg     180
aatagcgtct ggcagtcaga gatcattctg aaggtcaatg cgccgttaga tgatgaaatt     240
gcgttactga tcctgggac aacgctggtg agttttatct ggcctgcgca gaatccggaa     300
ttaatgcaaa acttgcgga acgtaacgtg accgtgatgg cgatggactc tgtgccgcgt     360
atctcacgcg cacaatcgct ggacgcacta agctcgatgg cgaacatcgc cggttatcgc     420
gccattgttg aagcggcaca tgaatttggg cgcttcttta ccgggcaaat tactgcggcc     480
gggaaagtgc caccggcaaa agtgatgtg attggtgcgg tgttgcagg tctggccgcc     540
attggcgcag caaacagtct cggcgcgatt gtgcgtgcat cgacacccg cccggaagtg     600
aaagaacaag ttcaaagtat gggcgcgaa ttcctcgagc tggatttaa agaggaagct     660
ggcagcggcg atggctatgc caaagtgatg tcggacgcgt tcatcaaagc ggaaatggaa     720
ctctttgccg cccaggcaaa agaggtcgat atcattgtca ccaccgcgct tattccaggc     780
aaaccagcgc cgaagctaat tacccgtgaa atggttgact ccatgaaggc gggcagtgtg     840
attgtcgacc tggcagccca aaacggcgg aactgtgaat acaccgtgcc gggtgaaatc     900
ttcactacgg aaaatggtgt caaagtgatt ggttataccg atcttccggg ccgtctgccg     960
acgcaatcct cacagcttta cggcacaaac ctcgttaatc tgctgaaact gttgtgcaaa    1020
gagaaagacg gcaatatcac tgttgatttt gatgatgtgg tgattcgcgg cgtgaccgtg    1080
atccgtgcgg cgaaattac ctggccggca ccgccgattc aggtatcagc tcagccgcag    1140
gcggcacaaa aagcggcacc ggaagtgaaa actgaggaaa aatgtacctg ctcaccgtgg    1200
cgtaaatacg cgttgatggc gctggcaatc attcttttg ctggatggc aagcgttgcg    1260
ccgaaagaat ccttgggca cttcaccgtt tcgcgctgg cctgcgttgt cggttattac    1320
gtggtgtgga atgtatcgca cgcgctgcat acaccgttga tgtcggtcac caacgcgatt    1380
tcagggatta ttgttgtcgg agcactgttg cagattggcc agggcggctg ggttagcttc    1440
cttagtttta tcgcggtgct tatagccagc attaatattt tcggtggctt caccgtgact    1500
```

```
cagcgcatgc tgaaaatgtt ccgcaaaaat taaggggtaa catatgtctg gaggattagt    1560
tacagctgca tacattgttg ccgcgatcct gtttatcttc agtctggccg gtctttcgaa    1620
acatgaaacg tctcgccagg gtaacaactt cggtatcgcc gggatggcga ttgcgttaat    1680
cgcaaccatt tttggaccgg atacgggtaa tgttggctgg atcttgctgg cgatggtcat    1740
tggtggggca attggtatcc gtctggcgaa gaaagttgaa atgaccgaaa tgccagaact    1800
ggtggcgatc ctgcatagct tcgtgggtct ggcggcagtg ctggttggct ttaacagcta    1860
tctgcatcat gacgcgggaa tggcaccgat tctggtcaat attcacctga cggaagtgtt    1920
cctcggtatc ttcatcgggg cggtaacgtt cacgggttcg gtggtggcgt tcggcaaact    1980
gtgtggcaag atttcgtcta aaccattgat gctgccaaac cgtcacaaaa tgaacctggc    2040
ggctctggtc gtttccttcc tgctgctgat tgtatttgtt cgcacggaca gcgtcggcct    2100
gcaagtgctg gcattgctga taatgaccgc aattgcgctg gtattcggct ggcatttagt    2160
cgcctccatc ggtggtgcag atatgccagt ggtggtgtcg atgctgaact cgtactccgg    2220
ctgggcggct gcggctgcgg gctttatgct cagcaacgac ctgctgattg tgaccggtgc    2280
gctggtcggt tcttcggggg ctatccttc ttacattatg tgtaaggcga tgaaccgttc    2340
ctttatcagc gttattgcgg gtggtttcgg caccgacggc tcttctactg gcgatgatca    2400
ggaagtgggt gagcaccgcg aaatcaccgc agaagagaca gcggaactgc tgaaaaactc    2460
ccattcagtg atcattactc cggggtacgg catggcagtc gcgcaggcgc aatatcctgt    2520
cgctgaaatt actgagaaat tgcgcgctcg tggtattaat gtgcgtttcg gtatccaccc    2580
ggtcgcgggg cgtttgcctg acatatgaa cgtattgctg gctgaagcaa aagtaccgta    2640
tgacatcgtg ctggaaatgg acgagatcaa tgatgacttt gctgataccg ataccgtact    2700
ggtgattggt gctaacgata cggttaaccc ggcggcgcag gatgatccga agagtccgat    2760
tgctggtatg cctgtgctgg aagtgtggaa agcgcagaac gtgattgtct ttaaacgttc    2820
gatgaacact ggctatgctg gtgtgcaaaa cccgctgttc ttcaaggaaa cacccacat    2880 gctgtttggt gacgccaaag ccagcgtgga tgcaatcctg aaagctctgt aa           2932
```

<210> SEQ ID NO 95
<211> LENGTH: 1401
<212> TYPE: DNA
<213> ORGANISM: Escherichia coli

<400> SEQUENCE: 95

```
atgccacatt cctacgatta cgatgccata gtaataggtt ccggccccgg cggcgaaggc      60
gctgcaatgg gcctggttaa gcaaggtgcg cgcgtcgcag ttatcgagcg ttatcaaaat     120
gttggcggcg gttgcaccca ctggggcacc atcccgtcga aagctctccg tcacgccgtc     180
agccgcatta tagaattcaa tcaaaaccca ctttacagcg accattcccg actgctccgc     240
tcttcttttg ccgatatcct taaccatgcc gataacgtga ttaatcaaca aacgcgcatg     300
cgtcagggat tttacgaacg taatcactgt gaaatattgc agggaaacgc tcgctttgtt     360
gacgagcata cgttggcgct ggattgcccg gacggcagcg ttgaaacact aaccgctgaa     420
aaatttgtta ttgcctgcgg ctctcgtcca tatcatccaa cagatgttga tttcacccat     480
ccacgcattt acgacagcga ctcaattctc agcatgcacc acgaaccgcg ccatgtactt     540
atctatggtc tggagtgat cggctgtgaa tatgcgtcga tcttccgcgg tatggatgta     600
aaagtggatc tgatcaacac ccgcgatcgc ctgctgcat ttctcgatca agagatgtca     660
gattctctct cctatcactt ctggaacagt ggcgtagtga ttcgtcacaa cgaagagtac     720
```

| | |
|---|---|
| gagaagatcg aaggctgtga cgatggtgtg atcatgcatc tgaagtcggg taaaaaactg | 780 |
| aaagctgact gcctgctcta tgccaacggt cgcaccggta taccgattc gctggcgtta | 840 |
| cagaacattg ggctagaaac tgacagccgc ggacagctga aggtcaacag catgtatcag | 900 |
| accgcacagc cacacgttta cgcggtgggc gacgtgattg gttatccgag cctggcgtcg | 960 |
| gcggcctatg accaggggcg cattgccgcg caggcgctgg taaaaggcga agccaccgca | 1020 |
| catctgattg aagatatccc taccggtatt tacaccatcc cggaaatcag ctctgtgggc | 1080 |
| aaaaccgaac agcagctgac cgcaatgaaa gtgccatatg aagtgggccg cgcccagttt | 1140 |
| aaacatctgg cacgcgcaca aatcgtcggc atgaacgtgg gcacgctgaa aattttgttc | 1200 |
| catcgggaaa caaaagagat tctgggtatt cactgctttg gcgagcgcgc tgccgaaatt | 1260 |
| attcatatcg gtcaggcgat tatggaacag aaaggtggcg gcaacactat tgagtacttc | 1320 |
| gtcaacacca cctttaacta cccgacgatg gcggaagcct atcgggtagc tgcgttaaac | 1380 |
| ggtttaaacc gcctgtttta a | 1401 |

<210> SEQ ID NO 96
<211> LENGTH: 1434
<212> TYPE: DNA
<213> ORGANISM: Streptococcus mutans

<400> SEQUENCE: 96

| | |
|---|---|
| atggcaatga caaaacaata taaaaattat gtcaatggcg agtggaagct ttcagaaaat | 60 |
| gaaattaaaa tctacgaacc agccagtgga gctgaattgg gttcagttcc agcaatgagt | 120 |
| actgaagaag tagattatgt ttatgcttca gccaagaaag ctcaaccagc ttggcgagca | 180 |
| ctttcataca tagaacgtgc tgcctaccct cataaggtag cagatatttt gatgcgtgat | 240 |
| aaagaaaaaa taggtgctat tctttccaaa gaggttgcta aaggttataa atcagcagtc | 300 |
| agcgaagttg ttcgtactgc agaaatcatt aattatgcag ctgaagaagg tcttcgtatg | 360 |
| gaaggtgaag tccttgaagg cggcagtttt gaagcagcca gcaagaaaaa aattgccgtt | 420 |
| gttcgtcgtg aaccagtagg tcttgtatta gctatttcac catttaacta ccctgttaac | 480 |
| ttggcaggtt cgaaaattgc accggctctt attgcgggaa atgttattgc ttttaaacca | 540 |
| ccgacgcaag gatcaatctc agggctctta cttgctgaag catttgctga agctggactt | 600 |
| cctgcaggtg tctttaatac cattacaggt cgtggttctg aaattggaga ctatattgta | 660 |
| gaacatcaag ccgttaactt tatcaatttc actggttcaa caggaattgg cgaacgtatt | 720 |
| ggcaaaatgg ctggtatgcg tccgattatg cttgaactcg gtggaaaaga ttcagccatc | 780 |
| gttcttgaag atgcggacct tgaattgact gctaaaaata ttattgcagg tgcttttggt | 840 |
| tattcaggtc aacgctgtac agcagttaaa cgtgttcttg tgatggaaag tgttgctgat | 900 |
| gaactggtcg aaaaaatccg tgaaaaagtt cttgcattaa caattggtaa tccagaagac | 960 |
| gatgcagata ttacaccgtt gattgataca aaatcagctg attatgtaga aggtctttatt | 1020 |
| aatgatgcca atgataaagg agccactgcc cttactgaaa tcaaacgtga aggtaatctt | 1080 |
| atctgtccaa tcctctttga taaggtaacg acagatatgc gtcttgcttg ggaagaacca | 1140 |
| tttggtcctg ttcttccgat cattcgtgtg acatctgtag aagaagccat tgaaatttct | 1200 |
| aacaaatcgg aatatggact tcaggcttct atctttacaa atgatttccc acgcgctttt | 1260 |
| ggtattgctg agcagcttga agttggtaca gttcatatca ataataagac acagcgcggc | 1320 |
| acggacaact tcccattctt aggggctaaa aaatcaggtg caggtattca aggggtaaaa | 1380 |

| tattctattg aagctatgac aactgttaaa tccgtcgtat ttgatatcaa ataa | 1434 |

<210> SEQ ID NO 97
<211> LENGTH: 996
<212> TYPE: DNA
<213> ORGANISM: Escherichia coli

<400> SEQUENCE: 97

| atgactatca aagtaggtat caacggtttt ggccgtatcg gtcgcattgt tttccgtgct | 60 |
| gctcagaaac gttctgacat cgagatcgtt gcaatcaacg acctgttaga cgctgattac | 120 |
| atggcataca tgctgaaata tgactccact cacggccgtt cgacggtac cgttgaagtg | 180 |
| aaagacggtc atctgatcgt taacggtaaa aaaatccgtg ttaccgctga acgtgatccg | 240 |
| gctaacctga atgggacga agttggtgtt gacgttgtcg ctgaagcaac tggtctgttc | 300 |
| ctgactgacg aaactgctcg taaacacatc accgctggtg cgaagaaagt ggttatgact | 360 |
| ggtccgtcta agacaacac tccgatgttc gttaaaggcg ctaacttcga caaatatgct | 420 |
| ggccaggaca tcgtttccaa cgcttcctgc accaccaact gcctggctcc gctggctaaa | 480 |
| gttatcaacg ataacttcgg catcatcgaa ggtctgatga ccaccgttca cgctactacc | 540 |
| gctactcaga aaaccgttga tggcccgtct cacaaagact ggcgcggcgg ccgcggcgct | 600 |
| tcccagaaca tcatcccgtc ctctaccggt gctgctaaag ctgtaggtaa agtactgcca | 660 |
| gaactgaatg caaactgac tggtatggcg ttccgcgttc cgaccccgaa cgtatctgta | 720 |
| gttgacctga ccgttcgtct ggaaaaagct gcaacttacg agcagatcaa agctgccgtt | 780 |
| aaagctgctg ctgaaggcga atgaaaggc gttctgggct acaccgaaga tgacgtagta | 840 |
| tctaccgatt tcaacggcga agtttgcact tccgtgttcg atgctaaagc tggtatcgct | 900 |
| ctgaacgaca acttcgtgaa actggtatcc tggtacgaca cgaaaccgg ttactccaac | 960 |
| aaagttctgg acctgatcgc tcacatctcc aaataa | 996 |

<210> SEQ ID NO 98
<211> LENGTH: 1650
<212> TYPE: DNA
<213> ORGANISM: Escherichia coli

<400> SEQUENCE: 98

| atgaaaaaca tcaatccaac gcagaccgct gcctggcagg cactacagaa acacttcgat | 60 |
| gaaatgaaag acgttacgat cgccgatctt tttgctaaag acggcgatcg tttttctaag | 120 |
| ttctccgcaa ccttcgacga tcagatgctg gtggattact ccaaaaaccg catcactgaa | 180 |
| gagacgctgg cgaaattaca ggatctggcg aaagagtgcg atctggcggg cgcgattaag | 240 |
| tcgatgttct ctggcgagaa gatcaaccgc actgaaaaacc gcgccgtgct gcacgtagcg | 300 |
| ctgcgtaacc gtagcaatac cccgattttg gttgatggca agacgtaat gccggaagtc | 360 |
| aacgcggtgc tggagaagat gaaaaccttc tcagaagcga ttatttccgg tgagtggaaa | 420 |
| ggttataccg gcaaagcaat cactgacgta gtgaacatcg gatcggcgg ttctgacctc | 480 |
| ggcccataca tggtgaccga agctctgcgt ccgtacaaaa accacctgaa catgcacttt | 540 |
| gtttctaacg tcgatgggac tcacatcgcg gaagtgctga aaaagtaaa cccggaaacc | 600 |
| acgctgttct tggtagcatc taaaaccttc accactcagg aaactatgac caacgcccat | 660 |
| agcgcgcgtg actggttcct gaaagcggca ggtgatgaaa acacgttgc aaaacacttt | 720 |
| gcggcgcttt ccaccaatgc caaagccgtt ggcgagtttg gtattgatac tgccaacatg | 780 |
| ttcgagttct gggactgggt tggcggccgt tactctttgt ggtcagcgat tggcctgtcg | 840 |

```
attgttctct ccatcggctt tgataacttc gttgaactgc tttccggcgc acacgcgatg      900
gacaagcatt tctccaccac gcctgccgag aaaaacctgc ctgtactgct ggcgctgatt      960
ggcatctggt acaacaattt ctttggtgcg gaaactgaag cgattctgcc gtatgaccag     1020
tatatgcacc gtttcgcggc gtacttccag cagggcaata tggagtccaa cggtaagtat     1080
gttgaccgta acgtaacgt tgtggattac cagactggcc cgattatctg gggtgaacca      1140
ggcactaacg tcagcacgc gttctaccag ctgatccacc agggaaccaa aatggtaccg      1200
tgcgatttca tcgctccggc tatcacccat aacccgctct ctgatcatca ccagaaactg     1260
ctgtctaact tcttcgccca gaccgaagcg ctggcgtttg gtaaatcccg cgaagtggtt     1320
gagcaggaat atcgtgatca gggtaaagat ccggcaacgc ttgactacgt ggtgccgttc     1380
aaagtattcg aaggtaaccg cccgaccaac tccatcctgc tgcgtgaaat cactccgttc     1440
agcctgggtg cgttgattgc gctgtatgag cacaaaatct ttactcaggg cgtgatcctg     1500
aacatcttca ccttcgacca gtggggcgtg gaactgggta acagctggc gaaccgtatt      1560 ctgccagagc tgaaagatga taaagaaatc agcagccacg atagctcgac caatggtctg     1620
attaaccgct ataaagcgtg gcgcggttaa                                       1650
```

<210> SEQ ID NO 99
<211> LENGTH: 963
<212> TYPE: DNA
<213> ORGANISM: Escherichia coli

<400> SEQUENCE: 99

```
atgattaaga aaatcggtgt gttgacaagc ggcggtgatg cgccaggcat gaacgccgca       60
attcgcgggg ttgttcgttc tgcgctgaca gaaggtctgg aagtaatggg tatttatgac      120
ggctatctgg gtctgtatga agaccgtatg gtacagctag accgttacag cgtgtctgac      180
atgatcaacc gtggcggtac gttcctcggt tctgcgcgtt tcccggaatt ccgcgacgag      240
aacatccgcg ccgtggctat cgaaaacctg aaaaaacgtg gtatcgacgc gctggtggtt      300
atcggcggtg acggttccta catgggtgca atgcgtctga ccgaaatggg cttcccgtgc      360
atcggtctgc cgggcactat cgacaacgac atcaaaggca ctgactacac tatcggtttc      420
ttcactgcgc tgagcaccgt tgtagaagcg atcgaccgtc tgcgtgacac ctcttcttct     480
caccagcgta tttccgtggt ggaagtgatg ggccgttatt gtggagatct gacgttggct      540
gcggccattg ccggtggctg tgaattcgtt gtggttccgg aagttgaatt cagccgtgaa      600
gacctggtaa acgaaatcaa agcgggtatc gcgaaaggta aaaacacgc gatcgtggcg       660 attaccgaac atatgtgtga tgttgacgaa ctggcgcatt tcatcgagaa agaaaccggt      720
cgtgaaaccc gcgcaactgt gctgggccac atccagcgcg tggttctcc ggtgccttac       780 gaccgtattc tggcttcccg tatgggcgct tacgctatcg atctgctgct ggcaggttac      840
ggcggtcgtt gtgtaggtat ccagaacgaa cagctggttc accacgacat catcgacgct     900
atcgaaaaca tgaagcgtcc gttcaaaggt gactggctgg actgcgcgaa aaaactgtat      960
taa                                                                    963
```

<210> SEQ ID NO 100
<211> LENGTH: 1476
<212> TYPE: DNA
<213> ORGANISM: Escherichia coli

<400> SEQUENCE: 100

```
atggcggtaa cgcaaacagc ccaggcctgt gacctggtca ttttcggcgc gaaaggcgac    60
cttgcgcgtc gtaaattgct gccttccctg tatcaactgg aaaaagccgg tcagctcaac   120
ccggacaccc ggattatcgg cgtagggcgt gctgactggg ataaagcggc atataccaaa   180
gttgtccgcg aggcgctcga aactttcatg aaagaaacca ttgatgaagg tttatgggac   240
accctgagtg cacgtctgga ttttttgtaat ctcgatgtca atgacactgc tgcattcagc   300
cgtctcggcg cgatgctgga tcaaaaaaat cgtatcacca ttaactactt tgccatgccg   360
cccagcactt ttggcgcaat ttgcaaaggg cttggcgagg caaaactgaa tgctaaaccg   420
gcacgcgtag tcatggagaa accgctgggg acgtcgctgg cgacctcgca ggaaatcaat   480
gatcaggttg gcgaatactt cgaggagtgc caggtttacc gtatcgacca ctatcttggt   540
aaagaaacgg tgctgaacct gttggcgctg cgttttgcta actccctgtt tgtgaataac   600
tgggacaatc gcaccattga tcatgttgag attaccgtgg cagaagaagt ggggatcgaa   660
gggcgctggg gctattttga taaagccggt cagatgcgcg acatgatcca gaaccacctg   720
ctgcaaattc tttgcatgat tgcgatgtct ccgccgtctg acctgagcgc agacagcatc   780
cgcgatgaaa aagtgaaagt actgaagtct ctgcgccgca tcgaccgctc caacgtacgc   840
gaaaaaaccg tacgcgggca atatactgcg ggcttcgccc agggcaaaaa agtgccggga   900
tatctggaag aagagggcgc gaacaagagc agcaatacag aaactttcgt ggcgatccgc   960
gtcgacattg ataactggcg ctgggccggt gtgccattct acctgcgtac tggtaaacgt  1020
ctgccgacca aatgttctga agtcgtggtc tatttcaaaa cacctgaact gaatctgttt  1080
aaagaatcgt ggcaggatct gccgcagaat aaactgacta ccgtctgca acctgatgaa  1140
ggcgtggata tccaggtact gaataaagtt cctggccttg accacaaaca taacctgcaa  1200
atcaccaagc tggatctgag ctattcagaa acctttaatc agacgcatct ggcggatgcc  1260
tatgaacgtt tgctgctgga accatgcgt ggtattcagg cactgtttgt acgtcgcgac  1320
gaagtggaag aagcctggaa atgggtagac tccattactg aggcgtgggc gatgacaat  1380
gatgcgccga accgtatca ggccggaacc tggggacccg ttgcctcggt ggcgatgatt  1440
acccgtgatg gtcgttcctg gaatgagttt gagtaa                            1476
```

<210> SEQ ID NO 101
<211> LENGTH: 474
<212> TYPE: PRT
<213> ORGANISM: Escherichia coli

<400> SEQUENCE: 101

```
Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110
```

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Ile Ile Gly Leu Glu Met Gly Thr
                180                 185                 190

Val Tyr His Ala Leu Gly Ser Gln Ile Asp Val Val Glu Met Phe Asp
            195                 200                 205

Gln Val Ile Pro Ala Ala Asp Lys Asp Ile Val Lys Val Phe Thr Lys
210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
450                 455                 460

Asp Leu Pro Asn Pro Lys Ala Lys Lys Lys
465                 470

<210> SEQ ID NO 102
<211> LENGTH: 474
<212> TYPE: PRT
<213> ORGANISM: artificial
<220> FEATURE:
<223> OTHER INFORMATION: Lpd mutant

<400> SEQUENCE: 102

```
Met Ser Thr Glu Ile Lys Thr Gln Val Val Leu Gly Ala Gly Pro
1               5                   10                  15
Ala Gly Tyr Ser Ala Ala Phe Arg Cys Ala Asp Leu Gly Leu Glu Thr
            20                  25                  30
Val Ile Val Glu Arg Tyr Asn Thr Leu Gly Val Cys Leu Asn Val
        35                  40                  45
Gly Cys Ile Pro Ser Lys Ala Leu Leu His Val Ala Lys Val Ile Glu
50                  55                  60
Glu Ala Lys Ala Leu Ala Glu His Gly Ile Val Phe Gly Glu Pro Lys
65                  70                  75                  80
Thr Asp Ile Asp Lys Ile Arg Thr Trp Lys Glu Lys Val Ile Asn Gln
                85                  90                  95
Leu Thr Gly Gly Leu Ala Gly Met Ala Lys Gly Arg Lys Val Lys Val
            100                 105                 110
Val Asn Gly Leu Gly Lys Phe Thr Gly Ala Asn Thr Leu Glu Val Glu
        115                 120                 125
Gly Glu Asn Gly Lys Thr Val Ile Asn Phe Asp Asn Ala Ile Ile Ala
    130                 135                 140
Ala Gly Ser Arg Pro Ile Gln Leu Pro Phe Ile Pro His Glu Asp Pro
145                 150                 155                 160
Arg Ile Trp Asp Ser Thr Asp Ala Leu Glu Leu Lys Glu Val Pro Glu
                165                 170                 175
Arg Leu Leu Val Met Gly Gly Ile Ile Ala Leu Glu Met Ala Thr
            180                 185                 190
Val Tyr His Ala Leu Gly Ser Gln Ile Asp Val Val Arg Lys His
        195                 200                 205
Gln Val Ile Arg Ala Ala Asp Lys Asp Ile Val Lys Val Phe Thr Lys
    210                 215                 220
Arg Ile Ser Lys Lys Phe Asn Leu Met Leu Glu Thr Lys Val Thr Ala
225                 230                 235                 240
Val Glu Ala Lys Glu Asp Gly Ile Tyr Val Thr Met Glu Gly Lys Lys
                245                 250                 255
Ala Pro Ala Glu Pro Gln Arg Tyr Asp Ala Val Leu Val Ala Ile Gly
            260                 265                 270
Arg Val Pro Asn Gly Lys Asn Leu Asp Ala Gly Lys Ala Gly Val Glu
        275                 280                 285
Val Asp Asp Arg Gly Phe Ile Arg Val Asp Lys Gln Leu Arg Thr Asn
    290                 295                 300
Val Pro His Ile Phe Ala Ile Gly Asp Ile Val Gly Gln Pro Met Leu
305                 310                 315                 320
Ala His Lys Gly Val His Glu Gly His Val Ala Ala Glu Val Ile Ala
                325                 330                 335
Gly Lys Lys His Tyr Phe Asp Pro Lys Val Ile Pro Ser Ile Ala Tyr
            340                 345                 350
Thr Glu Pro Glu Val Ala Trp Val Gly Leu Thr Glu Lys Glu Ala Lys
        355                 360                 365
Glu Lys Gly Ile Ser Tyr Glu Thr Ala Thr Phe Pro Trp Ala Ala Ser
    370                 375                 380
Gly Arg Ala Ile Ala Ser Asp Cys Ala Asp Gly Met Thr Lys Leu Ile
385                 390                 395                 400
Phe Asp Lys Glu Ser His Arg Val Ile Gly Gly Ala Ile Val Gly Thr
                405                 410                 415
Asn Gly Gly Glu Leu Leu Gly Glu Ile Gly Leu Ala Ile Glu Met Gly
```

```
            420                 425                 430
Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470
```

<210> SEQ ID NO 103
<211> LENGTH: 1548
<212> TYPE: DNA
<213> ORGANISM: Escherichia coli

<400> SEQUENCE: 103

| | | | | | |
|---|---|---|---|---|---|
| atgacggacc | atacaatgaa | gaaaaacccc | gtaagtatac | cacacaccgt | ctggtacgcc | 60 |
| gacgatatcc | gccgcggaga | acgcgaggcg | gcagatgtgc | tggggctcac | actctatgag | 120 |
| ctgatgcttc | gcgctggcga | ggccgcattc | caggtgtgtc | gttcggcgta | tcctgacgcc | 180 |
| cgccactggc | tggtgctgtg | cggtcatggt | aataacggcg | gcgatggcta | cgtggtcgcg | 240 |
| cgactggcca | aagcggtcgg | cattgaggtc | acgttgttgg | cccaggagag | cgacaaaccg | 300 |
| ttgccggaag | aggccgcgct | ggcacgcgaa | gcatggttaa | acgcgggtgg | cgagatccat | 360 |
| gcttcgaata | ttgtctggcc | cgaatcggta | gatctgattg | ttgatgcgct | gctcggtacc | 420 |
| ggtttgcggc | aagcgccccg | cgaatccatt | agccagttaa | tcgaccacgc | taattcccat | 480 |
| cctgcgccga | ttgtgcggt | tgatatccct | tccggcctgc | tggctgaaac | tggcgctacg | 540 |
| ccaggcgcgg | tgatcaacgc | cgatcacacc | atcacttta | ttgcgctgaa | accaggcttg | 600 |
| ctcactggaa | aagcgcggga | tgttaccgga | caactgcatt | ttgactcact | ggggctggat | 660 |
| agttggctgg | caggtcagga | gacgaaaatt | cagcggtttt | cagcagaaca | actttctcac | 720 |
| tggctaaaac | cgcgtcgccc | gacttcgcat | aaaggcgatc | acgggcggct | ggtaattatc | 780 |
| ggtggcgatc | acggcacggc | gggggctatt | cgtatgacgg | gggaagcggc | gctgcgtgct | 840 |
| ggtgctggtt | tagtccgagt | actgaccccgc | agtgaaaaca | ttgcgccgct | gctgactgca | 900 |
| cgaccggaat | tgatggtgca | tgaactgacg | atggactctc | ttaccgaaag | cctggaatgg | 960 |
| gccgatgtgg | tggtgattgg | tcccggtctg | ggccagcaag | agtgggggaa | aaaagcactg | 1020 |
| caaaaagttg | agaattttcg | caaaccgatg | ttgtgggatg | ccgatgcatt | gaacctgctg | 1080 |
| gcaatcaatc | ccgataagcg | tcacaatcgc | gtgatcacgc | cgcatcctgg | cgaggccgca | 1140 |
| cggttgttag | gctgttccgt | cgctgaaatt | gaaagtgacc | gcttacattg | cgccaaacgt | 1200 |
| ctggtacaac | gttatggcgg | cgtagcggtg | ctgaaaggtg | ccggaaccgt | ggtcgccgcc | 1260 |
| catcctgacg | ctttaggcat | tattgatgcc | ggaaatgcag | gcatggcgag | cggcggcatg | 1320 |
| ggcgatgtgc | tctctggtat | tattggcgca | ttgcttgggc | aaaaactgtc | gccgtatgat | 1380 |
| gcagcctgtg | caggctgtgt | cgcgcacggt | cggcagctg | acgtactggc | ggcgcgtttt | 1440 |
| ggaacgcgcg | ggatgctggc | aaccgatctc | ttttccacgc | tacagcgtat | tgttaacccg | 1500 |
| gaagtgactg | ataaaaacca | tgatgaatcg | agtaattccg | ctcccctga | | 1548 |

<210> SEQ ID NO 104
<211> LENGTH: 50
<212> TYPE: DNA
<213> ORGANISM: artificial
<220> FEATURE:
<223> OTHER INFORMATION: primer deletion xylAB 1

<400> SEQUENCE: 104
acgacatcat ccatcacccg cggcattacc tgattatgga gttcaatatg    50

<210> SEQ ID NO 105
<211> LENGTH: 50
<212> TYPE: DNA
<213> ORGANISM: artificial
<220> FEATURE:
<223> OTHER INFORMATION: primer deletion xylAB 2

<400> SEQUENCE: 105
cccccacccg gtcaggcagg ggataacgtt tacgccatta atggcagaag    50

<210> SEQ ID NO 106
<211> LENGTH: 50
<212> TYPE: DNA
<213> ORGANISM: artificial
<220> FEATURE:
<223> OTHER INFORMATION: primer deletion yjhH 1

<400> SEQUENCE: 106
aatgcgcgaa gttgccgact tcctgattaa taaaggggtc gacgggctgt    50

<210> SEQ ID NO 107
<211> LENGTH: 50
<212> TYPE: DNA
<213> ORGANISM: artificial
<220> FEATURE:
<223> OTHER INFORMATION: primer deletion yfhH 2

<400> SEQUENCE: 107
gtaccgactt aactgtgttg atcatcgtac gcaagtgacc aacgctgtcg    50

<210> SEQ ID NO 108
<211> LENGTH: 50
<212> TYPE: DNA
<213> ORGANISM: artificial
<220> FEATURE:
<223> OTHER INFORMATION: primer deletion yagE 1

<400> SEQUENCE: 108
ggcggcacca acgcccggga aaccatcgaa ctcagccagc acgcgcagca    50

<210> SEQ ID NO 109
<211> LENGTH: 50
<212> TYPE: DNA
<213> ORGANISM: artificial
<220> FEATURE:
<223> OTHER INFORMATION: primer deletion yagE 2

<400> SEQUENCE: 109
agcacggtga agtgcggatg ggcaccttg acggtatgga tcatgctgcg    50

<210> SEQ ID NO 110
<211> LENGTH: 50
<212> TYPE: DNA
<213> ORGANISM: artificial
<220> FEATURE:
<223> OTHER INFORMATION: primer deletion yiaE 1

<400> SEQUENCE: 110
catatttcag gctaaggtga tcgccttatc agtgaatgga gagaagcatg    50

<210> SEQ ID NO 111
<211> LENGTH: 50

```
<212> TYPE: DNA
<213> ORGANISM: artificial
<220> FEATURE:
<223> OTHER INFORMATION: primer deletion yiaE 2

<400> SEQUENCE: 111
tatcgggctt tactctacgc agtcgcggct tagtccgcga cgtgcggatt            50

<210> SEQ ID NO 112
<211> LENGTH: 50
<212> TYPE: DNA
<213> ORGANISM: artificial
<220> FEATURE:
<223> OTHER INFORMATION: primer deletion ycdW 1

<400> SEQUENCE: 112
aacgataagt gcgaataaat ttcgcacaac gcttttcggg agtcagtatg            50

<210> SEQ ID NO 113
<211> LENGTH: 50
<212> TYPE: DNA
<213> ORGANISM: artificial
<220> FEATURE:
<223> OTHER INFORMATION: primer deletion ycdW 2

<400> SEQUENCE: 113
ccaaggatag caggaatcct gatgctttat tagtagccgc gtgcgcggtc            50

<210> SEQ ID NO 114
<211> LENGTH: 100
<212> TYPE: DNA
<213> ORGANISM: artificial
<220> FEATURE:
<223> OTHER INFORMATION: primer deletion ptsG 1

<400> SEQUENCE: 114
atgtttaaga atgcatttgc taacctgcaa aaggtcggta aatcgctgat gctgccggta   60
tccgtactgc ctatcgcagg tgtaggctgg agctgcttcg                        100

<210> SEQ ID NO 115
<211> LENGTH: 100
<212> TYPE: DNA
<213> ORGANISM: artificial
<220> FEATURE:
<223> OTHER INFORMATION: primer deletion ptsG 2

<400> SEQUENCE: 115
ttagtggtta cggatgtact catccatctc ggttttcagg ttatcggatt tagtaccgaa   60
aatcgcctga acaccagaac catatgaata tcctccttag                        100

<210> SEQ ID NO 116
<211> LENGTH: 21
<212> TYPE: DNA
<213> ORGANISM: artificial
<220> FEATURE:
<223> OTHER INFORMATION: RBS120

<400> SEQUENCE: 116
atccggtata ggaggtatag a                                            21

<210> SEQ ID NO 117
<211> LENGTH: 100
<212> TYPE: DNA
<213> ORGANISM: artificial
<220> FEATURE:
```

<223> OTHER INFORMATION: primer deletion udhA 1

<400> SEQUENCE: 117

```
ggtgcgcgcg tcgcagttat cgagcgttat caaaatgttg gcggcggttg cacccactgg      60
ggcaccatcc cgtcgaaagc catatgaata tcctccttag                            100
```

<210> SEQ ID NO 118
<211> LENGTH: 100
<212> TYPE: DNA
<213> ORGANISM: artificial
<220> FEATURE:
<223> OTHER INFORMATION: primer deletion udhA 2

<400> SEQUENCE: 118

```
cccagaatct cttttgtttc ccgatggaac aaaattttca gcgtgcccac gttcatgccg      60
acgatttgtg cgcgtgccag tgtaggctgg agctgcttcg                            100
```

<210> SEQ ID NO 119
<211> LENGTH: 101
<212> TYPE: DNA
<213> ORGANISM: artificial
<220> FEATURE:
<223> OTHER INFORMATION: primer deletion pfkA 1

<400> SEQUENCE: 119

```
gttcctcggt tctgcgcgtt tcccggaatt ccgcgacgag aacatccgcg ccgtggctat      60
cgaaaacctg aaaaaacgtg gtgtaggctg gagctgcttc g                          101
```

<210> SEQ ID NO 120
<211> LENGTH: 102
<212> TYPE: DNA
<213> ORGANISM: artificial
<220> FEATURE:
<223> OTHER INFORMATION: primer deletion pfkA 2

<400> SEQUENCE: 120

```
ggcctgataa gcgaagcgca tcaggcattt ttgcttctgt catcggtttc agggtaaagg      60
aatctgcctt tttccgaaat cacatatgaa tatcctcctt ag                         102
```

<210> SEQ ID NO 121
<211> LENGTH: 83
<212> TYPE: DNA
<213> ORGANISM: artificial
<220> FEATURE:
<223> OTHER INFORMATION: PR01

<400> SEQUENCE: 121

```
acgttaaatc tatcaccgca agggataaat atctaacacc gtgcgtgttg acaattttac      60
ctctggcggt gataatggtt gca                                              83
```

<210> SEQ ID NO 122
<211> LENGTH: 714
<212> TYPE: DNA
<213> ORGANISM: artificial
<220> FEATURE:
<223> OTHER INFORMATION: CI857

<400> SEQUENCE: 122

```
atgagcacaa aaaagaaacc attaacacaa gagcagcttg aggacgcacg tcgccttaaa      60
gcaatttatg aaaaaaagaa aaatgaactt ggcttatccc aggaatctgt cgcagacaag     120
atggggatgg ggcagtcagg cgttggtgct ttatttaatg gcatcaatgc attaaatgct     180
```

```
tataacgccg cattgcttac aaaaattctc aaagttagcg ttgaagaatt tagcccttca    240
atcgccagag aaatctacga gatgtatgaa gcggttagta tgcagccgtc acttagaagt    300
gagtatgagt accctgtttt ttctcatgtt caggcaggga tgttctcacc taagcttaga    360
acctttacca aaggtgatgc ggagagatgg gtaagcacaa ccaaaaaagc cagtgattct    420
gcattctggc ttgaggttga aggtaattcc atgaccgcac caacaggctc caagccaagc    480
tttcctgacg gaatgttaat tctcgttgac cctgagcagg ctgttgagcc aggtgatttc    540
tgcatagcca gacttggggg tgatgagttt accttcaaga aactgatcag ggatagcggt    600
caggtgtttt tacaaccact aaacccacag tacccaatga tcccatgcaa tgagagttgt    660
tccgttgtgg ggaaagttat cgctagtcag tggcctgaag agacgtttgg ctga          714
```

<210> SEQ ID NO 123
<211> LENGTH: 34
<212> TYPE: DNA
<213> ORGANISM: artificial
<220> FEATURE:
<223> OTHER INFORMATION: RBS150

<400> SEQUENCE: 123

```
taccaactaa cgcacgttta agtaggaacc gtat                                 34
```

<210> SEQ ID NO 124
<211> LENGTH: 50
<212> TYPE: DNA
<213> ORGANISM: artificial
<220> FEATURE:
<223> OTHER INFORMATION: replacement gapA by gapN

<400> SEQUENCE: 124

```
acgtgactga ttctaacaaa acattaacac caactggcaa aatttttgtcc               50
```

<210> SEQ ID NO 125
<211> LENGTH: 50
<212> TYPE: DNA
<213> ORGANISM: artificial
<220> FEATURE:
<223> OTHER INFORMATION: replacement gapA by gapN

<400> SEQUENCE: 125

```
aaaaaagagc gaccgaagtc gctcttttta gatcacagtg tcatctcaac                50
```

<210> SEQ ID NO 126
<211> LENGTH: 43
<212> TYPE: DNA
<213> ORGANISM: artificial
<220> FEATURE:
<223> OTHER INFORMATION: ptrc

<400> SEQUENCE: 126

```
gagctgttga caattaatca tccggctcgt ataatgtgtg gaa                       43
```

<210> SEQ ID NO 127
<211> LENGTH: 50
<212> TYPE: DNA
<213> ORGANISM: artificial
<220> FEATURE:
<223> OTHER INFORMATION: primer replacement xylFGH promoter 1

<400> SEQUENCE: 127

```
ctaaaaattg gttacgttta tcgcggtgat tgttacttat taaaactgtc                50
```

```
<210> SEQ ID NO 128
<211> LENGTH: 50
<212> TYPE: DNA
<213> ORGANISM: artificial
<220> FEATURE:
<223> OTHER INFORMATION: primer replacement xylFGH promoter 2

<400> SEQUENCE: 128
tgagtagaat gttctttatt ttcatggtgt agggccttct gtagttagag            50
```

MODIFIED MICROORGANISM FOR THE OPTIMIZED PRODUCTION OF 2,4-DIHYDROXYBUTYRATE

INTRODUCTION

The present invention relates to a genetically modified microorganism for the production of 2,4-dihydroxybutyrate, by metabolic transformation of xylose via the 1,2,4-butanetriol intermediate. The invention also relates to a method for the production of 2,4-dihydroxybutyrate by culturing said genetically modified microorganism in a fermentation medium and recovering 2,4-DHB from said medium.

2,4-dihydroxybutyric acid (i.e. 2,4-DHB or DHB), also known as 2,4-dihydroxybutanoic acid or 2,4-dihydroxybutyrate, is a compound of high economic interest as it can serve as a precursor for the chemical synthesis of 2-hydroxy-4-(methylthio)-butyrate (HMTB), a methionine analogue widely used food additive in animal nutrition, notably in poultry. Indeed, HMTB can be included in animal diets as a low-priced amino acid substitute of methionine, in order to notably increase the meat yield (US2009/318715).

Conventionally, HMTB is produced by chemical synthesis process employing α-hydroxy-γ-butyrolactone (2HBL) in presence of methylmercaptan and of a basic or acidic catalyst. The 2HBL is prepared industrially in a known way from malic acid in three steps (DE19735575A1, AU2004200948A), or from γ-butyrolactone in two steps (WO2008/022953A1). The problems posed by these two routes lies in the difficulty in isolating 2HBL and in a very significant production of salts which have then to be removed. Moreover, petrochemical synthesis of HMTB is not economically viable as it relies on the use of hazardous materials and conditions as well as on expensive materials and reagents.

Recently, it has been shown that 2,4-DHB can be converted into α-hydroxy-γ-butyrolactone (2HBL) in aqueous media by adjusting the appropriate pH (US2013/0204016).

Thus, and even if there is no natural metabolic pathways for the biochemical production of 2,4-dihydroxybutyric acid, synthetic metabolic pathway(s) for DHB production in microorganisms represents an attractive alternative as it alleviates many of the above-mentioned problems. As a matter of fact, metabolic engineering approaches relying on recombinant expression of specific enzymes in microorganisms have recently been developed: WO2012/056318, WO2013/160762, WO2014/009435 and EP14306564.7 notably describe the production of 2,4-DHB by fermentation of glucose in genetically modified microorganisms, via different metabolic pathways. Most of the enzymes identified in these patent applications were obtained either by rational engineering based on structural and mechanistic knowledge of candidate enzymes acting on sterically similar cognate substrates, or by screening of natural enzymes and further improvement by rational design. More specifically, WO2012/056318 has identified three non-naturally occurring enzymes (malate kinase, malate semi-aldehyde dehydrogenase and a DHB dehydrogenase, all being mutated) which can be overexpressed in a microorganism in order to transform the metabolic intermediate (L)-Malate into 2,4-DHB; WO2013/160762 requires the heterogenous expression of various enzymes, some of them being mutated to improve the enzyme activity and/or substrate affinity (malyl-CoA synthetase, or succinyl-CoA: (L)-Malate-CoA transferase, and/or malyl-CoA lyase; malyl-CoA reductase; and DHB dehydrogenase) in order to transform the metabolic intermediate malate, or succinyl-CoA, or glycolyl-CoA into 2,4-DHB; while the method of WO2014/009435 relies on the conversion of the metabolic intermediate (L)-homoserine into 2-oxo-4-hydroxybutyrate (OHB) and the reduction of OHB in 2,4-DHB by recombinantly expressing two mutated enzymes (a homoserine transaminase and a DHB reductase).

The present invention proposes an alternative synthetic pathway for the microbial production of 2,4-dihydroxybutyric acid from the 1,2,4-butanetriol metabolic intermediate, in two single steps requiring successively the oxidation of 1,2,4-butanetriol into 2,4-dihydroxybutanal, followed by the oxidation of 2,4-dihydroxybutanal into 2,4-DHB.

The inventors have indeed surprisingly discovered that the overall production of 2,4-DHB can be greatly improved by genetically engineering the two above reactions in a microorganism capable of converting a carbon source, more particularly xylose, into 1,2,4-butanetriol.

The present invention therefore provides herein an alternative microorganism genetically modified for an optimized production of 2,4-dihydroxybutyrate from xylose. This microorganism, which is genetically engineered to convert xylose into 1,2,4-butanetriol, comprises further genetic modifications in order to:

oxidize 1,2,4-butanetriol into 2,4-dihydroxybutanal, and
oxidize 2,4-dihydroxybutanal into 2,4-DHB.

The invention also relates to a method for the production of 2,4-dihydroxybutyrate by fermentation comprising culturing the microorganism of the invention in a culture medium comprising xylose, and recovering the produced 2,4-DHB from the culture medium.

DETAILED DESCRIPTION OF THE INVENTION

It shall be understood that the following detailed description is not limitative and that various modifications, substitutions, omissions, and changes may be made without departing from the scope of the invention. It shall also be understood that the terminology used herein is for the purpose of describing particular embodiments of the invention, and is not intended to be limiting.

All publications, patents and patent applications cited herein, whether supra or infra, are hereby incorporated by reference in their entirety.

Furthermore, unless otherwise stated, all technical and scientific terms used herein have the same meanings as commonly understood by one of ordinary skill in the art. Conventional microbiological and molecular biological techniques are also those well-known and commonly used in the art. Such techniques are well known to the skilled person in the art and are fully explained fully in the literature (see, for example Sambrook et al., 2012).

Nevertheless, with respect to the use of different terms throughout the current specification, the following definitions more particularly apply.

The singular forms "a", "an", and "the" include herein plural reference unless the context clearly dictates otherwise. Thus, for example, a reference to "a microorganism" includes a plurality of such microorganisms, and a reference to "an endogenous gene" is a reference to one or more endogenous genes, and so forth.

The terms "comprise", "contain", "involve" or "include" or variations such as "comprises", "comprising", "containing", "involved", "includes", "including" are used herein in an inclusive sense, i.e. to specify the presence of the stated features but not to preclude the presence or addition of further features in various embodiments of the invention.

The term "microorganism", as used herein, refers to a living microscopic organism, which may be a single cell or a multicellular organism and which can generally be found in nature. In the context of the present invention, the microorganism is preferably a bacterium, yeast or fungus. More preferably, the microorganism of the invention is selected among Enterobacteriaceae, Bacillaceae, Clostridiaceae, Streptomycetaceae, Corynebacteriaceae and yeast. Even more preferably, the microorganism of the invention is a species of *Escherichia, Klebsiella, Thermoanaerobacterium, Clostridium, Corynebacterium* or *Saccharomyces*. Yet, even more preferably, the microorganism of the invention is selected from *Escherichia coli, Klebsiella pneumoniae, Thermoanaerobacterium thermosaccharolyticum, Clostridium acetobutylicum Corynebacterium glutamicum* and *Saccharomyces cerevisiae*. Most preferably, the microorganism of the invention is *Escherichia coli*.

The term "recombinant microorganism", "genetically modified microorganism", or "genetically engineered microorganism", as used herein, refers to a microorganism as defined above that is not found in nature and therefore genetically differs from its natural counterpart. In other words, it refers to a microorganism that is modified by introduction and/or by deletion and/or by modification of its genetic elements. Such modification can be performed by genetic engineering, by forcing the development and evolution of new metabolic pathways by culturing the microorganism under specific selection pressure, or by combining both methods (see, e.g. WO2005/073364 or WO2008/116852).

A microorganism genetically modified for the production of 2,4-DHB according to the invention therefore means that said microorganism is a recombinant microorganism as defined above that is capable of producing 2,4-DHB. In other words, said microorganism has been genetically modified to allow production of 2,4-DHB.

In the context of the present invention, a microorganism can be genetically modified by modulating the expression level of one or more endogenous genes. By "modulating", it is meant herein that the expression level of said gene is up-regulated, downregulated, or even completely abolished by comparison to its natural expression level. Such modulation can therefore result in an enhancement of the activity of the gene product, or alternatively, in a lower or null activity of the endogenous gene product.

The term "endogenous gene" refers herein to a gene that is naturally present in the microorganism.

An endogenous gene can be overexpressed by introducing heterologous sequences which favour upregulation in addition to endogenous regulatory elements or by substituting those endogenous regulatory elements with such heterologous sequences, or by introducing one or more supplementary copies of the endogenous gene into the chromosome or a plasmid within the microorganism. Endogenous gene activity and/or expression level can also be modified by introducing mutations into their coding sequence to modify the gene product. A deletion of an endogenous gene can also be performed to inhibit totally its expression within the microorganism. Another way to modulate the expression of an endogenous gene is to exchange its promoter (i.e. wild type promoter) with a stronger or weaker promoter to up or down regulate the expression level of this gene. Promoters suitable for such purpose can be homologous or heterologous and are well-known in the art. It is within the skill of the person in the art to select appropriate promoters for modulating the expression of an endogenous gene.

In addition, or alternatively, a microorganism can be genetically modified to express one or more exogenous genes, provided that said genes are introduced into the microorganism with all the regulatory elements necessary for their expression in the host microorganism. The modification or "transformation" of microorganisms with exogenous DNA is a routine task for those skilled in the art. In the context of the present invention, the term "overexpression" or "overexpressing" is also used herein in relation to the expression of exogenous genes in the microorganism.

By "exogenous gene" or "heterologous gene", it is meant herein that said gene is not naturally occurring in the microorganism. In order to express an exogenous gene in a microorganism, such gene can be directly integrated into the microorganism chromosome, or be expressed extra-chromosomally by plasmids or vectors within the microorganism. A variety of plasmids, which differ in respect of their origin of replication and of their copy number in a cell, are well known in the art and can be easily selected by the skilled practitioner for such purpose. Exogenous genes according to the invention are advantageously homologous genes.

In the context of the invention, the term "homologous gene" or "homolog" not only refers to a gene inherited by two species (i.e. microorganism species) by a theoretical common genetic ancestor, but also includes genes which may be genetically unrelated that have, nonetheless, evolved to encode proteins which perform similar functions and/or have similar structure (i.e. functional homolog). Therefore the term "functional homolog" refers herein to a gene that encodes a functionally homologous protein.

Using the information available in databases such as Uniprot (for proteins), Genbank (for genes), or NCBI (for proteins or genes), those skilled in the art can easily determine the sequence of a specific protein and/or gene of a microorganism, and identify based on this sequence the one of equivalent genes, or homologs, in another microorganism. This routine work can be performed by a sequence alignment of a specific gene sequence of a microorganism with gene sequences or the genome of other microorganisms, which can be found in the above mentioned databases. Such sequence alignment can advantageously be performed using the BLAST algorithm developed by Altschul et al. (1990). Once a sequence homology has been established between those sequences, a consensus sequence can be derived and used to design degenerate probes in order to clone the corresponding homolog gene of the related microorganism. These routine methods of molecular biology are well known to those skilled in the art.

It shall be further understood that, in the context of the present invention, should an exogenous gene encoding a protein of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described by Graf et al. (2000), Deml et al. (2001) and Davis & Olsen (2011). Several software have notably been developed for codon optimization determination such as the GeneOptimizer® software (Lifetechnologies) or the OptimumGene™ software of (GenScript). In other words, the exogenous gene encoding a protein of interest is preferably codon-optimized for expression in a specific microorganism.

The microorganism according to the invention can also be genetically modified to increase or decrease the activity of one or more proteins.

Increasing such activity can be obtained by improving the protein catalytic efficiency, by decreasing protein turnover, by decreasing messenger RNA (mRNA) turnover, by increasing transcription of the gene, or by increasing translation of the mRNA.

Improving the protein catalytic efficiency means increasing the kcat and/or decreasing the Km for a given substrate and/or a given cofactor, and/or increasing the Ki for a given inhibitor. kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Mutations can be introduced by site-directed mutagenesis by conventional methods such as Polymerase Chain Reaction (PCR), by random mutagenesis techniques, for example via mutagenic agents (Ultra-Violet rays or chemical agents like nitrosoguanidine (NTG) or ethylmethanesulfonate (EMS)) or DNA shuffling or error-prone PCR. Stabilizing the protein can also be achieved by adding a "tag" peptide sequence either at the N-terminus or the C-terminus of the protein. Such tags are well known in the art, and include, among others, the Glutathione-S-Transferase (GST).

Decreasing mRNA turnover can be achieved by modifying the gene sequence of the 5'-untranslated region (5'-UTR) and/or the coding region, and/or the 3'-UTR (Carrier and Keasling, 1999).

Increasing the transcription of a gene, whether endogenous or exogenous, can be achieved by increasing the number of its copies within the microorganism and/or by using a promoter leading to a higher level of expression of the gene compared to the wild type promoter. In the context of the present invention, the term "overexpression" or "overexpressing" is also used to designate an increase in transcription of a gene in a microorganism.

As indicated above, to increase the number of copies of a gene in the microorganism, said gene can be encoded chromosomally or extra-chromosomally. When the gene of interest is to be encoded on the chromosome, several copies of the gene can be introduced on the chromosome by methods of genetic recombination, which are well-known to in the art (e.g. gene replacement). When the gene is to be encoded extra-chromosomally in the microorganism, it can be carried by different types of plasmid that differ in respect to their origin of replication depending on the microorganism in which they can replicate, and by their copy number in the cell. The microorganism transformed by said plasmid can contain 1 to 5 copies of the plasmid, or about 20 copies of it, or even up to 500 copies of it, depending on the nature of the plasmid. Examples of low copy number plasmids which can replicate in *E. coli* include, without limitation, the pSC101 plasmid (tight replication), the RK2 plasmid (tight replication), as well as the pACYC and pRSF1010 plasmids, while an example of high copy number plasmid which can replicate in *E. coli* is pSK bluescript II.

Promoters which can increase the expression level of a gene are also well-known to the skilled person in the art, and can be homologous (originating from same species) or heterologous (originating from a different species). Examples of such promoters include, without limitation, the promoters Ptrc, Ptac, Plac, and the lambda promoter cI. These promoters can also be induced ("inducible promoters") by a particular compound or by specific external condition like temperature or light.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, to proportionally alter its production rate, and control its activity inside the cell. It is also possible to optimize the strength of a RBS sequence to achieve a targeted translation initiation rate by using the software RBS CALCULATOR (Salis, 2011). It is within the skill of the person in the art to select the RBS sequence based on the nature of the mRNA.

Decreasing the activity of a protein can mean either decreasing its specific catalytic activity by mutating the gene encoding said protein so as to change the corresponding amino acid sequence and/or decreasing concentrations of the protein in the cell by mutating the nucleotidic sequence or by deleting the coding region of said gene.

As used herein, the term "oxidoreductase" refers to an enzyme that is capable of either reducing or oxidizing its substrate reversibly or irreversibly depending on the operating conditions. More particularly, such enzyme acts by catalyzing the transfer of electrons from its substrate (electron donor), to another molecule called the oxidant (electron acceptor). In the context of the present invention, the selected oxidoreductases are oxidizing their respective substrate (1,2,4-butanetriol into 2,4-dihydroxybutanal, and 2,4-dihydroxybutanal into 2,4-DHB), more preferably in an irreversible manner. It is within the skill of the person in the art to adapt the operating conditions so that the oxidoreductases of the invention are oxidizing their substrate.

Oxidoreductases are conventionally classified as EC1 in the Enzyme Commission (EC) number classification of enzymes, which group over 20 subclasses of enzymes (such as EC 1.1 including oxidoreductases that act on the CH—OH group of donors, also known as alcohol oxidoreductases; EC 1.2 including oxidoreductases that act on the aldehyde or oxo group of donors; EC 1.3 including oxidoreductases that act on the CH—CH group of donors, also known as CH—CH oxidoreductases; EC 1.4 including oxidoreductases that act on the CH—NH2 group of donors, and are also known as amino acid oxidoreductases or monoamine oxidases; EC 1.5 including oxidoreductases that act on CH—NH group of donors; EC 1.6 including oxidoreductases that act on NADH or NADPH; EC 1.7 including oxidoreductases that act on other nitrogenous compounds as donors; EC 1.8 including oxidoreductases that act on a sulfur group of donors; EC 1.9 including oxidoreductases that act on a heme group of donors; EC 1.10 including oxidoreductases that act on diphenols and related substances as donors; EC 1.11 including oxidoreductases that act on peroxide as an acceptor, also known as peroxidases; EC 1.12 including oxidoreductases that act on hydrogen as donors; EC 1.13 including oxidoreductases that act on single donors with incorporation of molecular oxygen, also known as oxygenases; EC 1.14 including oxidoreductases that act on paired donors with incorporation of molecular oxygen; EC 1.15 including oxidoreductases that act on superoxide radicals as acceptors; EC 1.16 including oxidoreductases that oxidize metal ions; EC 1.17 including oxidoreductases that act on CH or CH2 groups; EC 1.18 including oxidoreductases that act on iron-sulfur proteins as donors; EC 1.19 including oxidoreductases that act on reduced flavodoxin as a donor; EC 1.20 including oxidoreductases that act on phosphorus or arsenic in donors; EC 1.21 including oxidoreductases that act on X—H and Y—H to form an X—Y bond; and EC 1.97 including other oxidoreductases). Some of these oxidoreductases are capable to use NADP or NAD+ as cofactors, and, as such, are referred as NAD+/NADP+ oxidoreductases.

The term "source of carbon", "carbon source" or "carbon substrate" according to the present invention refers to any carbon source capable of being metabolized by a microorganism and which contains at least one carbon atom. A carbon source may be derived from renewable feed-stock. Renewable feed-stock is defined as raw material required for certain industrial processes that can be regenerated within a brief delay and in sufficient amount to permit its transformation into the desired product. Vegetal biomass, treated or not, is an interesting renewable carbon source. In the context of the present invention, xylose is a carbon source, and a source of carbon other than xylose is advantageously a carbohydrate.

The term "carbohydrate" refers herein to any carbon source capable of being metabolized by a microorganism and containing at least one carbon atom, two atoms of hydrogen and one atom of oxygen. The carbohydrate of the invention is preferably selected from the group consisting of monosaccharides such as glucose, fructose, mannose, galactose and the like, disaccharides such as sucrose, cellobiose, maltose, lactose and the like, oligosaccharides such as raffinose, stacchyose, maltodextrins and the like, polysaccharides such as cellulose, hemicellulose, starch and the like, methanol, formaldehyde and glycerol. According to a preferred embodiment of the invention, the source of carbon other than xylose is advantageously a carbohydrate comprising 3, 6 or 12 carbon atoms, or any combination thereof. In a more preferred embodiment of the invention, the source of carbon other than xylose is selected from glycerol, glucose, galactose, fructose, lactose, maltose, sucrose, and any combination thereof. More preferably, the carbon source other than xylose is selected from glycerol, glucose, sucrose, and any combination thereof and most preferably is glucose.

In a first aspect of the present invention, the present invention is directed to a microorganism genetically modified for the production of 2,4-dihydroxybutyrate by converting xylose into 1,2,4-butanetriol, wherein said microorganism is further genetically modified for:
 i) oxidizing 1,2,4-butanetriol into 2,4-dihydroxybutanal; and
 ii) oxidizing 2,4-dihydroxybutanal into 2,4-dihydroxybutyrate.

More preferably, the oxidizing steps i) and ii) are directed to the exclusive conversion of 1,2,4-butanetriol into 2,4-dihydroxybutanal, and of 2,4-dihydroxybutanal into 2,4-dihydroxybutyrate, respectively. In other words, it is particularly preferred that no metabolic intermediate is produced by the microorganism during the oxidation of 1,2,4-butanetriol into 2,4-dihydroxybutanal, and of 2,4-dihydroxybutanal into 2,4-DHB, in order to optimize the 2,4-DHB production. Such exclusive conversion can be achieved by using the enzymes further described below.

According to a preferred embodiment, the genetic modification i) is an overexpression of at least one gene encoding an oxidoreductase acting on the CH—OH group of donors (EC 1.1 enzyme), and/or the genetic modification ii) is an overexpression of at least one gene encoding an oxidoreductase acting on the aldehyde or oxo group of donors (EC 1.2 enzyme).

Examples of oxidoreductases acting on the CH—OH group of donors include, without limitation, EC 1.1.1 enzymes (oxidoreductases with NAD+ or NADP+ as acceptor, also known as NAD+/NADP+ oxidoreductases), EC 1.1.2 enzymes (oxidoreductases with a cytochrome as acceptor), EC 1.1.3 enzymes (oxidoreductases with oxygen as acceptor), EC 1.1.4 enzymes (oxidoreductases with a disulphide as an acceptor), EC 1.1.5 enzymes (oxidoreductases with a quinone or similar compound as acceptor), EC 1.1.98 enzymes (oxidoreductases with other known acceptors), and EC 1.1.99 enzymes (oxidoreductases with other acceptors).

Examples of oxidoreductases acting on the aldehyde or oxo group of donors include, without limitation, EC 1.2.1 enzymes (oxidoreductases with NAD+ or NADP+ as acceptor, also known as NAD+/NADP+ oxidoreductases), EC 1.2.2 enzymes (oxidoreductases with a cytochrome as acceptor), EC 1.2.3 enzymes (oxidoreductases with oxygen as acceptor), EC 1.2.4 enzymes (oxidoreductases with a disulphide as acceptor), EC 1.2.5 enzymes (oxidoreductases with a quinone or similar compound as acceptor), EC 1.2.7 enzymes (oxidoreductases with an iron-sulfur protein as acceptor), and EC 1.2.99 enzymes (oxidoreductases with other acceptors).

Enzymes displaying the above activities are well-known in the art and can be easily identified by the skilled person in the art, from example from publicly available databases such as BRENDA.

In order to oxidize 1,2,4-butanetriol into 2,4-dihydroxybutanal, the oxidoreductase acting on the CH—OH group of donors (EC 1.1 enzyme) is preferably selected from the group consisting of alcohol dehydrogenases (i.e. aldehyde reductases), aldehyde dehydrogenase, lactaldehyde reductases, glyoxylate reductases, didehydrogluconate reductases, and any combination thereof. More preferably, said EC 1.1 oxidoreductase is an alcohol dehydrogenase (i.e an aldehyde reductase) or a lactaldehyde reductase. Yet, even more preferably, said EC 1.1 oxidoreductase is an NAD+/NADP+ oxidoreductase acting on the CH—OH group of donors (i.e. an EC 1.1.1 enzyme), or an oxidoreductase acting on the CH—OH group of donors with other acceptors (i.e. an EC 1.1.99 enzyme). Most preferably, said EC 1.1 enzyme is an EC 1.1.1 enzyme. It is within the skill of the person in the art to select the EC 1.1 enzymes that are suitable for the purposes of the invention, and identify their corresponding gene sequences.

Particularly preferred oxidoreductases acting on the CH—OH group of donors (EC 1.1 enzymes) are described in Table 1 below according to their sequence identification and accession number in a database: alcohol dehydrogenases include, without limitation, the enzymes of sequence SEQ ID NO:1 to SEQ ID NO:40; lactaldehyde reductases include, without limitation, the enzyme of sequence SEQ ID NO:41; glyoxylate reductases include, without limitation, the enzymes of sequence SEQ ID NO:42 and SEQ ID NO:43, and the didehydrogluconate reductases include, without limitation the enzymes of sequence SEQ ID NO:44 and SEQ ID NO:45.

In a particularly preferred embodiment of the present invention, the oxidoreductase acting on the CH—OH group of donors (EC 1.1 enzyme) is the enzyme of sequence SEQ ID NO:36 or SEQ ID NO:41, in accordance with the conversion metabolic pathway of 1,2,4-butanetriol into 2,4-dihydroxybutanal as described in FIG. 1.

Genes coding for the above-mentioned oxidoreductases are also well-known in the art, and are described in Table 1 below:

genes encoding alcohol dehydrogenases include, without limitation, the *Escherichia coli* genes frmA (also known as adhC), adhP (also known as yddN), yiaY, eutG (also known as yffV), yqhD, yeaE, ydhF, yhdN, ybdR, ybdH, ybjJ, ydjL, ahr, yahK, tas (also known as ygdS), and gldA; the *Clostridium acetutylicum* genes bdhB, bdhA and CA_C3392, the *Saccharomyces cerevisiae* genes ADH1, ADH2, ADH3, ADH4 and bdh1; the *Bacillus subtilis* genes yhdN and bdhA; the *Gluconobacter oxydans* gene GOX1615; the *Arabidopsis thaliana* gene AKR4C9; the *Leishmania donovani* gene A4UTP6; the *Thermoanaerobacterethaolicus* gene adhA; the *Corynebacterium glutamicum* genes butA and budC; the *Klebsiella pneumoniae* gene budC; the *Serratia marcescens* gene slaC; the *Hypocrea jecorina* gene gld2; the *Clostridium butyricum* gene dhaT; the *Citrobacter Freundii* gene dhaT; the *Klebsiella pneumoniae* gene dhaT; and the *Rhodoccus erythropolis* gene encoding the NMDA-dependant alcohol dehydrogenase; and the *Amycolatopsis methanolica* gene encoding the NMDA-dependant alcohol dehydrogenase;

genes encoding a lactaldehyde reductase include, without limitation, the *Escherichia coli* gene fucO;

genes encoding a glyoxylate reductase include, without limitation, the *Escherichia coli* genes ghrA (also known as ycdW) and ghrB (also known as yiaE); and genes encoding a didehydrogluconate reductase include, without limitation, the *Escherichia coli* genes dkgA (also known as yqhE) and dkgB (also known as yafB).

In a particularly preferred embodiment of the present invention, the oxidoreductase acting on the CH—OH group of donors (EC 1.1 enzyme) is encoded by the fucO gene from *Escherichia coli* and/or by the dhaT gene from *Clostridium butyricum, Citrobacter freundii* or *Klebsiella pneumoniae*, i.e. according to the conversion metabolic pathway of 1,2,4-butanetriol into 2,4-dihydroxybutanal as described in FIG. 1.

As indicated above, the microorganism of the invention is also genetically modified for ii) oxidizing 2,4-dihydroxybutanal into 2,4-dihydroxybutyrate. To do so, at least one gene encoding an oxidoreductase acting on the aldehyde or oxo group of donors (EC 1.2 enzyme) can be overexpressed in the microorganism.

Accordingly, the oxidoreductase acting on the aldehyde or oxo group of donors (EC 1.2 enzyme) is preferably selected from the group consisting of aldehyde dehydrogenases, aldehyde oxidases, and any combination thereof. More preferably, said EC 1.2 oxidoreductase is an aldehyde dehydrogenase. Yet, even more preferably, said EC 1.2 oxidoreductase is an NAD+/NADP+ oxidoreductase acting on the aldehyde or oxo group of donors (i.e. an EC 1.2.1 enzyme), or an oxidoreductase acting on the aldehyde or oxo group of donors with oxygen as acceptor (i.e. an EC 1.2.3 enzyme). Most preferably, said EC 1.2 enzyme is an EC 1.2.1 enzyme. It is within the skill of the person in the art to select the EC 1.2 enzymes that are suitable for the purposes of the invention, and identify their corresponding gene sequences.

Particularly preferred oxidoreductases acting on the aldehyde or oxo group of donors (EC 1.2 enzymes) are described in Table 1 below according to their sequence identification and accession number in a database: aldehyde dehydrogenases include, without limitation, the enzymes of sequence SEQ ID NO:46 to SEQ ID NO:60; aldehyde oxidases include, without limitation, the enzyme of sequence SEQ ID NO:61.

In a particularly preferred embodiment of the present invention, the oxidoreductase acting on the aldehyde or oxo group of donors (EC 1.2 enzyme) the enzyme of sequence SEQ ID NO:46, SEQ ID NO:54 or SEQ ID NO:55, in accordance with the conversion metabolic pathway of 2,4-dihydroxybutanal into 2,4-dihydroxybutyrate as described in FIG. 1.

Genes coding for the above-mentioned oxidoreductases are also well-known in the art, and are described in Table 1 below:

genes encoding aldehyde dehydrogenases include, without limitation, the *Escherichia coli* genes puuC, sad, gabD, prr (also known as ydcW), aldA, aldB (also known as yiaX), feaB, and astD; the *Klebsiella pneumoniae* gene KPN_01018; the *Saccharomyces cerevisiae* genes ALD4 and ALD5; the *Pseudomonas putida* gene davD; the *Pseudomonas* sp. gene amnC; and the *Methanocaldococcus jannaschii* gene MJ1411;

genes encoding dioxovalerate dehydrogenases include, without limitation, the *Bacillus licheniformis* gene ycbD; and genes encoding aldehyde oxidases include, without limitation, the *Zea mays* gene A01.

In a particularly preferred embodiment of the present invention, the oxidoreductase acting on the aldehyde or oxo group of donors (EC 1.2 enzyme) is encoded by the aldA, aldB, or puuC gene from *Escherichia coli*, i.e. according to the conversion metabolic pathway of 2,4-dihydroxybutanal into 2,4-dihydroxybutyrate as described in FIG. 1.

It must further be noted that when endogenous genes coding for the above activities are already present in the microorganism of interest, they are advantageously overexpressed in said microorganism. By contrast, when the microorganism does not naturally comprise genes coding for such activities, the microorganism is advantageously transformed with one or more exogenous genes coding for said enzyme(s): said exogenous genes are said to be also overexpressed. As explained above, exogenous genes are preferably synthetic genes that have been codon-optimized for their expression in the microorganism of interest.

In the context of the present invention, the microorganism is capable of converting xylose into 1,2,4-butanetriol. Microorganisms genetically modified for the conversion of xylose into 1,2,4-butanetriol, in particular for an exclusive conversion of xylose into 1,2,4-butanetriol, are well-known in the art, and have notably been described by patent application WO2008/091288 and US2013/0203141, incorporated herein by reference.

Accordingly, in a preferred embodiment, the genetic modification for converting xylose into 1,2,4-butanetriol is an overexpression of at least one of the following genes:

a gene encoding a xylose dehydrogenase, a gene encoding a xylonolactonase, a gene encoding a xylonate dehydratase, a gene encoding a 3-deoxy-D-glycero-pentulosonate (DGP) decarboxylase, a gene encoding a 1,2,4-butanetriol dehydrogenase, any combination thereof.

Genes coding for the above described enzymes are well-known in the art:

genes encoding a xylose dehydrogenase are disclosed in US2013/0203141 and WO2008/091288, incorporated herein by reference, and include without limitation the xdh encoding genes from *Caulobacter crescentus*,

*Haloarcula marismortui, Burkholderia fugorum* LB400 and *Haloferax volcanii* DS2, genes encoding a xylonolactonase include, without limitation, the xylC gene from *Caulobacter crescentus*, genes encoding a D-xylonate dehydratase are disclosed in US2013/0203141 and WO2008/091288, incorporated herein by reference, and include without limitation the yjhG and yagF genes from *E. coli*, genes encoding a 3-deoxy-D-glycero-pentulosonate decarboxylase are disclosed in US2013/0203141 and WO2008/091288, incorporated herein by reference, and include without limitation the mdlC gene from *Pseudomonas putida*, and genes encoding a NADPH dependant 1,2,4-butanetriol dehydrogenase are disclosed in US2013/0203141 and WO2008/091288, incorporated herein by reference, and include without limitation the adhP and yqhD genes from *E. coli*.

In a preferred embodiment, notably when the genetically modified microorganism is *E. coli*:

α) genes encoding xylose dehydrogenases, xylonolactonases, and 3-deoxy-D-glycero-pentulosonate decarboxylases are heterologous genes introduced into the microorganism, and β) genes encoding xylonate dehydratase and 1,2,4-butanetriol dehydrogenases are endogenous genes, and are therefore advantageously overexpressed.

In a particularly preferred embodiment of the present invention, the xylose dehydrogenase is encoded by the xdh gene from *Caulobacter crescentus*, the xylonolactonase is encoded by the xylC gene from *Caulobacter crescentus*, the xylonate dehydratase is encoded by the yjhG and/or yagF genes from *E. coli*, the 3-deoxy-D-glycero-pentulosonate decarboxylase is encoded by the mdlC gene from *Pseudomonas putida*, and the 1,2,4-butanetriol dehydrogenase is encoded by the adhP and/or yqhD genes from *E. coli*, i.e. according to the conversion metabolic pathway of xylose into 1,2,4-butanetriol as described in FIG. 1.

The nucleotide of the above mentioned genes, or the amino acid sequence encoded by said genes, are described in Table 1 below, according to their accession number and version in a database and/or according to their sequence identification.

When endogenous genes coding for the above activities are already present in the microorganism of interest, they are advantageously overexpressed in said microorganism. By contrast, when the microorganism does not naturally comprise genes coding for such activities, the microorganism is advantageously transformed with one or more exogenous genes coding for said enzyme(s): said exogenous genes are said to be also overexpressed. As explained above, exogenous genes are preferably synthetic genes that have been codon-optimized for their expression in the microorganism of interest.

According to a preferred embodiment, the microorganism of the invention is further genetically modified for:

iii) providing reducing power and/or energy for 2,4-dihydroxybutyrate production and microorganism growth from a carbon source other than xylose, and/or iv) at least partially, preferably totally, inhibiting carbon catabolite repression.

The genetic modification iii) as described above is particularly advantageous as it optimizes 2,4-DHB production, by using an alternative carbon source rather than xylose for the provision of reducing power and/or energy, so that the xylose can be exclusively converted into 2,4-dihydroxybutyrate.

In order to provide reducing power and/or energy for 1,2,4-butanetriol production and microorganism growth from a carbon source other than xylose, the microorganism according to the invention is preferably genetically modified by deleting and/or attenuating genes encoding enzymes using xylose or other metabolites that produces a flux that competes with the conversion of xylose into 2,4-dihydroxybutyrate.

Thus, according to a preferred embodiment of the invention, the genetic modification iii) is an attenuation and/or deletion of at least one of the following genes:

a gene encoding a xylose isomerase (e.g. xylA gene from *E. coli*), a gene encoding a xylulose kinase (e.g. xylB gene from *E. coli*), a gene encoding a 3-deoxy-D-glycero-pentulosonate aldolases (e.g. yjhH and/or yagE genes from *E. coli*), a gene encoding a keto-acid dehydrogenase (e.g. yiaE and/or ycdW genes from *E. coli*), and any combination thereof.

These genes as well as methods for deleting or attenuating them are fully disclosed in US2013/0203141, incorporated herein by reference.

The nucleotide of the above mentioned genes, or the amino acid sequence encoded by said genes, are also described in Table 1 below, according to their accession number and version in a database and/or according to their sequence identification.

Should the microorganism of the invention be genetically modified as described above, it is accordingly preferred that the microorganism uses a carbon source other than xylose for providing the reducing power and/or energy necessary for 2,4-DHB production and for the growth of the microorganism. In this regard, it is well known in the art that some microorganisms prefer some specific carbon sources over others. Notably, most naturally occurring microorganisms, among which *Escherichia coli*, prefer using glucose over other sugars even if they are capable of metabolizing an array of monosaccharides (Kim et al., 2010). However, some microorganisms are not capable of co-utilizing glucose and xylose in an effective manner. Indeed, a diauxic fermentation pattern may occur in microorganisms when two sugars are present in the culture medium: this regulatory mechanism is well-known in the art as catabolite repression, and has been reported by Monod in the 1940s, for glucose and lactose. This mechanism has been extensively studied in Enterobacteriaceae. In *E. coli*, it has been notably recognized that catabolite repression occurs as follows: the glucose enters with the aid of glucose specific permease EIICB-glc (encoded by ptsG) into the phosphoenolpyruvate (PEP): carbohydrate phosphotransferase system (PTS); during glucose transport, the level of cyclic AMP (cAMP) is lowered by dephosphorylated EIIAglc (encoded by crr), which in turn limits the availability of the catabolite repressor protein (CRP) and cAMP complex (cAMP-CRP); subsequently, all the genes involved in the catabolism of sugars other than glucose and which are generally regulated by cAMP-CRP are repressed. Catabolite repression by carbohydrates that are not transported by PTS system have also been reported in the literature but are not well understood (Hogema et al., 1997).

Accordingly, in a preferred embodiment, the genetic modification iv) which allows the inhibition of carbon catabolite repression is selected from at least one of the following:

deletion of a gene encoding a glucose permease of the phosphotransferase system, deletion of a gene encoding a phosphocarrier Hpr protein,
expression, preferably from a constitutive or inducible promoter not regulated by cAMP-CRP, of a gene and/or operon involved in a sugar importer system wherein said sugar is a carbon source other than xylose,
expression of a gene encoding a xylose transporter, such as a symporter or an ABC transporter preferably from a constitutive or inducible promoter not regulated by cAMP-CRP,
overexpression of a gene encoding a glucose symporter,
overexpression of a gene encoding a glucose facilitator,
overexpression of a gene encoding a glucokinase,
modulation of the expression of a gene involved in cAMP levels, preferably of a gene encoding adenylate cyclase,
modulation of the expression a gene encoding a CRP and/or a CRP-like protein,
expression of a gene encoding a cAMP-independent CRP protein, preferably from a constitutive or inducible promoter not regulated by cAMP-CRP, and
any combination thereof.

More preferably, for the co-utilisation of xylose and glucose, a deletion of a gene encoding a phophotransferase and/or a phosphocarrier Hpr protein is advantageously combined with an overexpression of a gene encoding a glucose permease or a glucose facilitator, along with an overexpression of a gene encoding a glucokinase.

Genes coding for the above described proteins are well-known in the art:
genes encoding a glucose permease of the phosphotransferase system include, without limitation, the pstG gene from *E. coli*,
genes encoding a phosphocarrier Hpr protein, which is one of two sugar-non-specific protein constituents of the phosphoenolpyruvate:sugar phosphotransferase system (PTS sugar), include, without limitation, the ptsH gene from *E. coli*,
genes/operon involved in a sugar importer system (PTS or other system) include, without limitation, the lacY gene from *E. coli* for the assimilation of lactose, the malFG genes from *E. coli* for the assimilation of maltose, and the scrKYABR or cscBKAR operons respectively from *Salmonella typhimurium* and *E. coli* for the assimilation of sucrose,
genes encoding a xylose transporter include, without limitation, the xylFGH operon from *E. coli*, the xylE and araE genes from *E. coli*,
genes encoding a glucose symporter include, without limitation, the galP gene from *E. coli*,
genes encoding a glucose facilitator include, without limitation, the glf gene from *Zymomonas mobilis*,
genes encoding a glucokinase include, without limitation, the glk gene from *E. coli*,
genes encoding an adenylate cyclase, include, without limitation the cyaA gene from *E. coli*,
genes encoding a CRP and/or a CRP-like protein include, without limitation, the CRP genes from *E. coli* and the ccpA gene from *Bacillus subtilis* and other firmicutes,
genes encoding a cAMP-independent CRP protein have been described by Hogema et al. (1997), and include, without limitation, genes encoding CRP proteins mutated in two regions: from residues 53 to 62 corresponding of the cAMP-binding domain of the CRP protein and from residues 141 to 148 corresponding to a proximal boundary of the DNA-binding domain (Helix-Turn-Helix). Examples of such protein mutants include CRP mutants Asp to His residue 53, Ser to Phe residue 62, Gly to Asp residue 141, Arg to Asp residue 142, Leu to Arg residue 148, and any combination thereof.

More preferably, for the co-utilisation of xylose and glucose in *E. coli*, the ptsG or ptsH gene deletion can be combined with an overexpression of the galP or glf gene along with an overexpression of the glk gene.

The nucleotide sequence of the above mentioned genes, or the amino acid sequence encoded by said genes, are described in Table 1 below, according to their accession number and version in a database and/or according to their sequence identification.

As explained above, when endogenous genes coding for the above activities are already present in the microorganism of interest, they are advantageously overexpressed in said microorganism. If, however, the microorganism does not naturally comprise genes coding for such activities, the microorganism is advantageously transformed with one or more exogenous genes coding for said enzyme(s): said exogenous genes are said to be also overexpressed. As explained above, exogenous genes are preferably synthetic genes that have been codon-optimized for their expression in the microorganism of interest. By contrast, endogenous genes can be deleted or their expression attenuated according to any one of the methods described above.

Carbon sources other than xylose according to the invention are as defined above, and include, without limitation, carbohydrates comprising 3, 6 or 12 carbon atoms, or any combination thereof. Preferably, the sources of carbon other than xylose are selected from the group consisting of glycerol, glucose, galactose, fructose, lactose, maltose, sucrose, and any combination thereof.

Most preferably, the source of carbon other than xylose used in the present invention is glucose.

Alternatively, the source of carbon other than xylose can be sucrose. Accordingly, in a preferred embodiment of the invention, the microorganism comprises further genetic modification(s) to use sucrose as source of carbon other than xylose, as described in WO2012/004247, incorporated herein by reference. To do so, the microorganism preferably comprises functional genes coding for a PTS sucrose utilization system and/or for a non-PTS sucrose utilization system.

A PTS sucrose utilization system is a system for sucrose utilization based on the transport of sucrose by a phosphoenolpyruvate (PEP)-dependent sucrose phosphotransferase system (Sucrose-PTS). A phosphotransferase system couples the transport of a sugar (e.g. sucrose or glucose) with the phosphorylation of the sugar using PEP as phosphate donor. After transport into the cell, the sucrose-phosphate is cleaved into glucose-6-phosphate and fructose by an invertase. Fructose is then phosphorylated into fructose-6-phosphate by a fructokinase. The genes coding for this PTS sucrose utilization system can be controlled by a regulatory protein.

A non-PTS sucrose utilization system is a system for sucrose utilization based on transport of sucrose by a system independent of phosphoenolpyruvate. After transport into the cell, the sucrose is cleaved into glucose and fructose by an invertase. Fructose is then phosphorylated into fructose-6-phosphate by a fructokinase and glucose is phosphorylated into glucose-6-phosphate by a glucokinase. The genes coding for this non-PTS sucrose utilization system can be controlled by a regulatory protein.

In a particularly preferred embodiment of the invention, the microorganism expresses naturally or has been genetically modified to express the genes of the operon scrKYABR from *Salmonella*, i.e. the scrK gene encoding a fructokinase, the scrY gene encoding a porin, the scrA gene encoding the IIBC protein, the scrB gene encoding a sucrose-6-P invertase, and the scrR gene encoding a repressor, and any combination thereof. A conjugative plasmid pUR400 bearing scrKYABR might be used to transform the microorganism. These genes can be expressed in the microorganism alone, in any combination comprising at least two of these genes, or all together in a combination. The gene scrR can preferably be omitted.

In particularly preferred embodiment of the invention, the microorganism expresses naturally or has been genetically modified to express the genes from the *E. coli* strain EC3132, i.e. the operon cscBKAR encoding a sucrose:proton symport transport system (cscB gene), a fructokinase (cscK gene), an invertase (cscA gene) and a sucrose-specific repressor (cscR gene). These genes can be expressed in the microorganism alone, in any combination comprising at least two of these genes, or all together in a combination. The gene cscR can preferably be omitted. Homologous genes from other organisms can also be used.

Yet, in a preferred embodiment, the microorganism of the invention comprises a further genetic modification of at least one gene involved in the production of NADPH as a source of reducing power. Indeed, reducing enzymes such as dehydrogenases are in need of reducing power available in the microorganism, particularly in the form of NADPH. Strategies for increasing NADPH availability in the cell are well known in the art, and have notably been reviewed by Lee et al. (2013) and also described by U.S. Pat. No. 8,088,620, WO2012/055798 and EP14305691.9, herein incorporated by reference.

According to the present invention, the genetic modification for improving the production of NADPH, and therefore its availability in the microorganism, is preferably selected from:

overexpression of a gene or operon encoding a membrane-bound transhydrogenase, deletion or attenuation of a gene encoding a soluble transhydrogenase, overexpression of a gene encoding a NADPH generating glyceraldehyde 3-phosphate dehydrogenase, deletion or attenuation of a gene encoding a phosphoglucose isomerase, deletion or attenuation of a gene encoding a phosphofructokinase, overexpression of a gene encoding a glucose-6-phosphate dehydrogenase, overexpression of a mutant gene encoding a lipoamide dehydrogenase capable of generating NADPH, overexpression of a gene encoding a bi-functional NAD(P)H-hydrate repair enzyme, and any combination thereof.

The deletion or attenuation of a gene encoding a phosphofructokinase is more preferably combined with an overexpression of a gene encoding a glucose-6-phosphate dehydrogenase, in order to increase the flux of NADPH through the pentose phosphate pathway.

More preferably, the genetic modification for improving the production of NADPH is selected from:

overexpression of a gene encoding a membrane-bound transhydrogenase, deletion or attenuation of a gene encoding a phosphoglucose isomerase and/or a soluble transhydrogenase, and overexpression of a gene encoding a NADPH generating glyceraldehyde 3-phosphate dehydrogenase.

Genes coding for the above described proteins are well-known in the art:

genes or operons encoding a membrane-bound transhydrogenase include, without limitation the pntAB operon from *E. coli*, as notably described by WO2012/055798A1, genes encoding a soluble transhydrogenase include, without limitation, the udhA gene from *E. coli*, genes encoding a NADPH generating glyceraldehyde 3-phosphate dehydrogenase include, without limitation, the gapN from *Streptococcus mutans* (as described by Centeno-Leija et al., 2013) which can be used for example to substitute the endogenous gapA gene from *E. coli*, genes encoding a phosphoglucose isomerase include, without limitation the pgi gene from *E. coli*, genes encoding a phosphofructokinase include, without limitation, the pfkA gene from *E. coli* as notably described by WO2005/047498, genes encoding a glucose-6-phosphate dehydrogenase include, without limitation, the zwf gene from *E. coli* as notably described by Lim et al. (2002), mutant genes encoding a lipoamide dehydrogenase capable of generating NADPH include, without limitation, the mutant lpd gene (lpd*) from *E. coli* as notably described by Bocanegra et al. (1993), and genes encoding a bi-functional NAD(P)H-hydrate repair enzyme include, without limitation, the yjeF gene from *E. coli* as notably described by Marbaix et al. (2011).

In *E. coli*, should the pfkA gene be deleted or attenuated, such genetic modification is preferably combined with an overexpression of the zwf gene.

More preferably, the genetic modification for improving the production of NADPH is selected from:

overexpression of a pntAB operon from *E. coli*, deletion of the pfkA gene and/or udhA gene from *E. coli*, and substitution of a gapA from *E. coli* by a gapN gene from *Streptococcus mutans*.

The nucleotide sequence of the above mentioned genes, or the amino acid sequence encoded by said genes, are described in Table 1 below, according to their accession number and version in a database and/or according to their sequence identification.

As explained above, when endogenous genes coding for the above activities are already present in the microorganism of interest, they are advantageously overexpressed in said microorganism. If, however, the microorganism does not naturally comprise genes coding for such activities, the microorganism is advantageously transformed with one or more exogenous genes coding for said enzyme(s): said exogenous genes are said to be also overexpressed. As explained above, exogenous genes are preferably synthetic genes that have been codon-optimized for their expression in the microorganism of interest. By contrast, endogenous genes can be deleted or their expression attenuated according to any one of the methods described above.

TABLE 1

Genes and proteins of the invention

| Enzyme full name(s) | Gene name | Origin (Genus species) | SEQ ID NO | Database | Accession number in the database | Version number in the database |
|---|---|---|---|---|---|---|
| S-(hydroxymethyl) glutathione dehydrogenase-alcohol dehydrogenase class-III | frmA/ adhC | *Escherichia coli* (strain K12) | 1 | UNIPROT | P25437 | ND |
| alcohol dehydrogenase, propanol-preferring | adhP/ yddN | *Escherichia coli* (strain K12) | 2 | UNIPROT | P39451 | ND |
| probable alcohol dehydrogenase | yiaY | *Escherichia coli* (strain K12) | 3 | UNIPROT | P37686 | ND |
| ethanolamine utilization protein EutG | eutG/ yffV | *Escherichia coli* (strain K12) | 4 | UNIPROT | P76553 | ND |
| alcohol dehydrogenase YqhD | yqhD | *Escherichia coli* (strain K12) | 5 | UNIPROT | Q46856 | ND |
| uncharacterized protein YeaE | yeaE | *Escherichia coli* (strain K12) | 6 | UNIPROT | P76234 | ND |
| oxidoreductase YdhF | ydhF | *Escherichia coli* (strain K12) | 7 | UNIPROT | P76187 | ND |
| uncharacterized protein YhdN | yhdN | *Escherichia coli* (strain K12) | 8 | UNIPROT | P36677 | ND |
| uncharacterized zinc-type alcohol dehydrogenase-like protein YbdR | ybdR | *Escherichia coli* (strain K12) | 9 | UNIPROT | P77316 | ND |
| uncharacterized oxidoreductase YbdH | ybdH | *Escherichia coli* (strain K12) | 10 | UNIPROT | P45579 | ND |
| uncharacterized zinc-type alcohol dehydrogenase-like protein YdjJ | ydjJ | *Escherichia coli* (strain K12) | 11 | UNIPROT | P77280 | ND |
| uncharacterized zinc-type alcohol dehydrogenase-like protein YdjL | ydjL | *Escherichia coli* (strain K12) | 12 | UNIPROT | P77539 | ND |
| NADH-dependent butanol dehydrogenase B | bdhB | *Clostridium acetobutylicum* | 13 | UNIPROT | Q04945 | ND |
| NADH-dependent butanol dehydrogenase A | bdhA | *Clostridium acetobutylicum* | 14 | UNIPROT | Q04944 | ND |
| NADH-dependent butanol dehydrogenase | CA_C3392 | *Clostridium acetobutylicum* | 15 | UNIPROT | Q97DT0 | ND |
| alcohol dehydrogenase 1 | ADH1 | *Saccharomyces cerevisiae* | 16 | UNIPROT | P00330 | ND |
| alcohol dehydrogenase 2 | ADH2 | *Saccharomyces cerevisiae* | 17 | UNIPROT | P00331 | ND |
| alcohol dehydrogenase 3 | ADH3 | *Saccharomyces cerevisiae* | 18 | UNIPROT | P07246 | ND |
| alcohol dehydrogenase 4 | ADH4 | *Saccharomyces cerevisiae* | 19 | UNIPROT | P10127 | ND |
| general stress protein 69 | yhdN | *Bacillus subtilis* (strain 168) | 20 | UNIPROT | P80874 | ND |
| putative oxidoreductase | GOX 1615 | *Gluconobacter oxydans* | 21 | UNIPROT | Q5FQJ0 | ND |
| aldehyde reductase Ahr | ahr | *Escherichia coli* (strain K12) | 22 | UNIPROT | P27250 | ND |
| aldo-keto reductase family 4 member C9 | AKR4C9 | *Arabidopsis thaliana* | 23 | UNIPROT | Q0PGJ6 | ND |
| prostaglandin f2-alpha synthase | A4UTP6 | *Leishmania donovani* | 24 | UNIPROT | A4UTP6 | ND |
| aldehyde reductase YahK | yahK | *Escherichia coli* (strain K12) | 25 | UNIPROT | P75691 | ND |
| protein tas | tas/ ygdS | *Escherichia coli* (strain K12) | 26 | UNIPROT | P0A9T4 | ND |
| long-chain primary alcohol dehydrogenase AdhA | adhA | *Thermoanaerobacter ethaolicus* | 27 | UNIPROT | Q9F282 | ND |
| (R,R)-butanediol dehydrogenase | bdhA | *Bacillus subtilis* (strain 168) | 28 | UNIPROT | O34788 | ND |
| (R,R)-butanediol dehydrogenase | bdh1 | *Saccharomyces cerevisiae* | 29 | UNIPROT | P39714 | ND |
| L-2,3-butanediol dehydrogenase/acetoin reductase | butA | *Corynebacterium glutamicum* | 30 | UNIPROT | Q8NMA4 | ND |
| diacetyl reductase [(S)-acetoin forming] | budC | *Klebsiella pneumoniae* | 31 | UNIPROT | Q48436 | ND |
| slaC | slaC | *Serratia marcescens* | 32 | UNIPROT | F8U1P6 | ND |
| glycerol dehydrogenase | gldA | *Escherichia coli* (strain K12) | 33 | UNIPROT | P0A9S5 | ND |
| L-2,3-butanediol dehydrogenase | budC | *Corynebacterium Glutamicum* | 34 | UNIPROT | Q9ZNN8 | ND |

TABLE 1-continued

Genes and proteins of the invention

| Enzyme full name(s) | Gene name | Origin (Genus species) | SEQ ID NO | Database | Accession number in the database | Version number in the database |
|---|---|---|---|---|---|---|
| glycerol 2-dehydrogenase (NADP(+)) | gld2 | *Hypocrea jecorina* | 35 | UNIPROT | Q0GYU4 | ND |
| 1,3-propanediol dehydrogenase | dhaT | *Clostridium butyricum* | 36 | UNIPROT | Q8GEZ6 | ND |
| 1,3-propanediol dehydrogenase | dhaT | *Citrobacter Freundii* | 37 | UNIPROT | P45513 | ND |
| 1,3-propanediol dehydrogenase | dhaT | *Klebsiella pneumoniae* | 38 | UNIPROT | Q59477 | ND |
| NDMA-dependent alcohol dehydrogenase | ND | *Rhodoccus erythropolis* | 39 | UNIPROT | P81747 | ND |
| NDMA-dependent alcohol dehydrogenase | ND | *Amycolatopsis methanolica* | 40 | UNIPROT | P80175 | ND |
| lactaldehyde reductase | fucO | *Escherichia coli* (strain K12) | 41 | UNIPROT | P0A9S1 | ND |
| glyoxylate/hydroxypyruvate reductase A | ghrA/ ycdW | *Escherichia coli* (strain K12) | 42 | UNIPROT | P75913 | ND |
| glyoxylate/hydroxypyruvate reductase B | ghrB/ yiaE | *Escherichia coli* (strain K12) | 43 | UNIPROT | P37666 | ND |
| 2,5-diketo-D-gluconic acid reductase A | dkgA/ yqhE | *Escherichia coli* (strain K12) | 44 | UNIPROT | Q46857 | ND |
| 2,5-diketo-D-gluconic acid reductase B | dkgB/ yafB | *Escherichia coli* (strain K12) | 45 | UNIPROT | P30863 | ND |
| aldehyde dehydrogenase PuuC | puuC | *Escherichia coli* (strain K12) | 46 | UNIPROT | P23883 | ND |
| aldehyde dehydrogenase | KPN_01018 | *Klebsiella pneumoniae* | 47 | UNIPROT | A6T782 | ND |
| potassium-activated aldehyde dehydrogenase, mitochondrial | ALD4 | *Saccharomyces cerevisiae* | 48 | UNIPROT | P46367 | ND |
| aldehyde dehydrogenase 5, mitochondrial | ALD5 | *Saccharomyces cerevisiae* | 49 | UNIPROT | P40047 | ND |
| succinate semialdehyde dehydrogenase [NAD(P)+] Sad | sad | *Escherichia coli* (strain K12) | 50 | UNIPROT | P76149 | ND |
| succinate-semialdehyde dehydrogenase [NADP(+)] GabD | gabD | *Escherichia coli* (strain K12) | 51 | UNIPROT | P25526 | ND |
| gamma-aminobutyraldehyde dehydrogenase | prr/ ydcW | *Escherichia coli* (strain K12) | 52 | UNIPROT | P77674 | ND |
| glutarate-semialdehyde dehydrogenase DavD | davD | *Pseudomonas putida* | 53 | UNIPROT | Q88RC0 | ND |
| lactaldehyde dehydrogenase | aldA | *Escherichia coli* (strain K12) | 54 | UNIPROT | P25553 | ND |
| aldehyde dehydrogenase B | aldB/ yiaX | *Escherichia coli* (strain K12) | 55 | UNIPROT | P37685 | ND |
| lactaldehyde dehydrogenase | MJ1411 | *Methanocaldococcus jannaschii* | 56 | UNIPROT | Q58806 | ND |
| aldehyde dehydrogenase YbcD | ycbD | *Bacillus licheniformis* | 57 | UNIPROT | Q65NX0 | ND |
| 2-aminomuconic 6-semialdehyde dehydrogenase | amnC | *Pseudomonas sp.* | 58 | UNIPROT | Q9KWS5 | ND |
| phenylacetaldehyde dehydrogenase | feaB | *Escherichia coli* (strain K12) | 59 | UNIPROT | P80668 | ND |
| N-succinylglutamate 5-semialdehyde dehydrogenase | astD | *Escherichia coli* (strain K12) | 60 | UNIPROT | P76217 | ND |
| indole-3-acetaldehyde oxidase | AO1 | *Zea mays* (maize) | 61 | UNIPROT | O23887 | ND |
| xylose dehydrogenase | xdh | *Caulobacter crescentus* | 62 | ND | ND | ND |
| | xdh | *Haloarcula marismortui* | ND | Genbank | AAW78223 | AAW78223.1 GI: 58429660 |
| | not available | *Burkholderia fugorum* LB400 | ND | Genbank | GN088955 | GN088955.1 GI: 226882916 |
| | gfo2 | *Haloferax volcanii* DS2 | ND | NCBI | YP_003533786 | YP_003533786.1 GI: 292653888 |
| xylonolactonase (xylolactone hydrolase) | xylC | *Caulobacter crescentus* | 63 | ND | ND | ND |
| D-xylonate dehydratase | yjhG | *Escherichia coli* | 64 | ND | ND | ND |
| Alcohol dehydrogenase | yagF | *Escherichia coli* | 65 | ND | ND | ND |
| (NADPH dependant 1,2,4-butanetriol dehydrogenase; NADPH dependant 1,4-butanediol dehydrogenase) | adhP | *Escherichia coli* | 66 | ND | ND | ND |
| | yqhD | *Escherichia coli* | 67 | ND | ND | ND |
| 3-deoxy-D-glycero-pentulosonic acid decarboxylase | mdlC | *Pseudomonas putida* | 68 | ND | ND | ND |

TABLE 1-continued

Genes and proteins of the invention

| Enzyme full name(s) | Gene name | Origin (Genus species) | SEQ ID NO | Database | Accession number in the database | Version number in the database |
|---|---|---|---|---|---|---|
| (3-deoxy-D-glycero-pentulosonate decarboxylase; benzoylformate decarboxylase; 2-keto acid decarboxylase) | | | | | | |
| D-xylose isomerase | xylA | Escherichia coli | 69 | ND | ND | ND |
| D-xylulose kinase | xylB | Escherichia coli | 70 | ND | ND | ND |
| 3-deoxy-D-glero-pentulosonic acid aldolase | yjhH | Escherichia coli | 71 | ND | ND | ND |
| | yagE | Escherichia coli | 72 | ND | ND | ND |
| keto-acid dehydrogenase | yiaE | Escherichia coli | 73 | ND | ND | ND |
| D-xylulose kinase | ycdW | Escherichia coli | 74 | ND | ND | ND |
| glucose phophotransferase Enzyme IIBC(Glc) (glucose permease) | ptsG | Escherichia coli | 75 | ND | ND | ND |
| EIIA(Glc), phosphocarrier for glucose PTS transport (Carbohydrate repression resistance) | crr | Escherichia coli | 76 | ND | ND | ND |
| histine protein (PTS system histidine phosphocarrier protein HPr, (phosphohistidinoprotein-hexose phosphotransferase) | ptsH (hpr) | Escherichia coli | 77 | ND | ND | ND |
| lactose permease | lacY | Escherichia coli | 78 | ND | ND | ND |
| membrane subunit of the maltose ABC transporter | malF | Escherichia coli | 79 | ND | ND | ND |
| EIIA(Glc), phosphocarrier for glucose PTS transport (Carbohydrate repression resistance) | malG | Escherichia coli | 80 | ND | ND | ND |
| importer of sucrose | scr KYABR | Salmonella typhimurium | 81 | ND | ND | ND |
| sucrose:proton symport transport system | cscBKAR | Escherichia coli | 82 | ND | ND | ND |
| importer of xylose | xylFGH | Escherichia coli | 83 | ND | ND | ND |
| glucose permease (galactose:H+ symporter) | galP | Escherichia coli | 84 | ND | ND | ND |
| glucose facilitator | glf | Zymomonas mobilis | 85 | ND | ND | ND |
| glucokinase | glk | Zymomonas mobilis | 86 | ND | ND | ND |
| importer of xylose | glk | Escherichia coli | 87 | ND | ND | ND |
| adenylate cyclase | cyaA | Escherichia coli | 88 | ND | ND | ND |
| CRP (cAMP receptor protein; cAMP-activated global transcription factor) and mutated CRP (*) | crp | Escherichia coli | 89 | ND | ND | ND |
| | crp* | Escherichia coli | 90 | ND | ND | ND |
| | | | 91 | ND | ND | ND |
| | | | 92 | ND | ND | ND |
| | | | 93 | ND | ND | ND |
| CRP-like protein (catabolite control protein A) | ccpA | Bacillus subtilis | ND | NCBI | NC_000964 (entire genome) | NC_000964.3 GI: 255767013 |
| membrane-bound transhydrogenase (membrane bound proton translocating pyridine nucleotide transhydrogenase) | pntAB | Escherichia coli | 94 | ND | ND | ND |
| soluble pyridine nucleotide transhydrogenase | sthA (udhA) | Escherichia coli | 95 | ND | ND | ND |
| NADP-dependent glyceraldehyde-3-phosphate dehydrogenase | gapN | Streptococcus mutans | 96 | ND | ND | ND |
| NADH generating glyceraldehyde-3-phosphate (Glyceraldehyde 3-phosphate dehydrogenase A) | gapA | Escherichia coli | 97 | ND | ND | ND |
| glucose-6-phosphate isomerase (phosphoglucose isomerase) | pgi | Escherichia coli | 98 | ND | ND | ND |
| phospho-fructokinase (6-phospho-fructokinase-1) | pfkA | Escherichia coli | 99 | ND | ND | ND |
| glucose-6-phosphate 1-dehydrogenase | zwf | Escherichia coli | 100 | ND | ND | ND |
| NADPH generating dihydrolipoamide | lpd | Escherichia coli | 101 | ND | ND | ND |

TABLE 1-continued

Genes and proteins of the invention

| Enzyme full name(s) | Gene name | Origin (Genus species) | SEQ ID NO | Database | Accession number in the database | Version number in the database |
|---|---|---|---|---|---|---|
| dehydrogenase (lipoamide dehydrogenase), and its mutated version (*) | lpd* | *Escherichia coli* | 102 | ND | ND | ND |
| Bifunctional NAD(P)H-hydrate repair enzyme (NAD(P)HX epimerase/ NAD(P)HX dehydratase) | yjeF (nrr) | *Escherichia coli* | 103 | ND | ND | ND |

(ND = non disclosed)

In another aspect, the present invention relates to a method for the production of 2,4-dihydroxybutyrate comprising:
a) culturing the genetically modified microorganism of the invention as described above in a culture medium comprising xylose, under fermentation conditions allowing conversion of xylose into 2,4-dihydroxybutyrate, and
b) recovering the 2,4-dihydroxybutyrate from said culture medium.

Fermentation mediums and sources of carbon are well known in the art. According to the invention, the terms "fermentative process", "fermentation" or "culture" are used interchangeably to refer to the experimental conditions allowing the growth of a given microorganism. The growth of a microorganism is generally performed in fermenters with an appropriate growth medium adapted to the microorganism being used.

An "appropriate culture medium" means herein a medium (e.g., a sterile, liquid media) comprising nutrients essential or beneficial to the maintenance and/or growth of the microorganism such as carbon sources or carbon substrates; nitrogen sources, for example peptone, yeast extracts, meat extracts, malt extracts, urea, ammonium sulfate, ammonium chloride, ammonium nitrate and ammonium phosphate; phosphorus sources, for example monopotassium phosphate or dipotassium phosphate; trace elements (e.g., metal salts) for example magnesium salts, cobalt salts and/or manganese salts; as well as growth factors such as amino acids and vitamins.

According to a preferred embodiment, the culture medium of step a) further comprises a carbon source other than xylose, which is preferably a carbohydrate.

Said carbohydrate can be selected from the group consisting of monosaccharides such as glucose, fructose, mannose, arabinose, galactose and the like, disaccharides such as sucrose, cellobiose, maltose, lactose and the like, oligosaccharides such as raffinose, stacchyose, maltodextrins and the like, polysaccharides such as cellulose, hemicellulose, starch and the like, methanol, formaldehyde and glycerol. Particularly preferred carbohydrates according to the invention comprise 3, 6 or 12 carbon atoms, and are more preferably glycerol, glucose, fructose, galactose, lactose, maltose, sucrose and any combination thereof. Most preferably, the carbohydrate is glucose. Alternatively, said carbohydrate can be sucrose.

In a preferred embodiment of the invention, the carbon source, preferably the carbohydrate, is derived from renewable feed-stock, such as vegetable biomass.

The person skilled in the art can easily determine the culture conditions necessary for growing the microorganism according to the invention. In particular, it is well know that bacteria can be fermented at a temperature comprised between 20° C. and 55° C., preferentially between 25° C. and 40° C. *E. coli* can more particularly be cultured at a temperature comprised between about 30° C. and about 37° C.

The method of the invention can be performed either in a batch process, in a fed-batch process or in a continuous process, and under aerobic, micro-aerobic or anaerobic conditions.

A fermentation "under aerobic conditions" means that oxygen is provided to the culture by dissolving gas into the liquid phase of the culture. This can be achieved by (1) sparging oxygen containing gas (e.g. air) into the liquid phase, or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes, thereby improving the general metabolism of the strain.

Micro-aerobic conditions can be used herein and are defined as culture conditions wherein low percentages of oxygen (e.g. using a mixture of gas containing between 0.1 and 10% of oxygen, completed to 100% with nitrogen) are dissolved into the liquid phase.

By contrast, "anaerobic conditions" are defined as culture conditions wherein no oxygen is provided to the culture medium. Strictly anaerobic conditions can be obtained by sparging an inert gas like nitrogen into the culture medium to remove traces of other gas. Nitrate can be used as an electron acceptor to improve ATP production by the strain and improve its metabolism.

According to a preferred embodiment, the method of the invention further comprises a step c) of purifying the 2,4-DHB of step b). Methods for purifying carboxylic acids and in particular hydroxyacids are well known in the art, and have notably been described in WO2002/090312, WO2002/022544 and WO2012/153042, which are incorporated herein by reference. Preferably, the 2,4-DHB is purified after its recovering in the culture medium by means well known by the man skilled in the art and in particular ion exchange chromatography techniques like ion-exchange resins or fixed or simulated moving bed ion exchange resins.

DRAWINGS

FIG. 1 represents the metabolic pathway for the conversion of D-xylose into 2,4-DHB (*: genes that are optionally deleted or attenuated).

EXAMPLES

The present invention is further defined in the following examples. It should be understood that these examples, while indicating preferred embodiments of the invention, are given by way of illustration only. From above disclosure and these examples, the man skilled in the art can make various changes of the invention to adapt it to various uses and conditions without modifying the essentials means of the invention.

Exemplary genes and enzymes required for constructing microorganisms with these capabilities are described as well as methods for cloning and transformation, monitoring product formation and using the engineered microorganisms for production.

In particular, examples show modified *Escherichia coli* (*E. coli*) strains, but these modifications can easily be performed in other microorganisms of the same family.

*Escherichia coli* belongs to the Enterobacteriaceae family, which comprises members that are Gram-negative, rod-shaped, non-spore forming and are typically 1-5 μm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organism, but other important members of the Enterobacteriaceae family include *Klebsiella*, in particular *Klebsiella terrigena*, *Klebsiella planticola* or *Klebsiella oxytoca*, *Pantoea* and *Salmonella*.

Protocols

Several protocols have been used to construct 2,4-dihydroxybutanoic acid producing strains described in the following examples.

Protocol 1 (Chromosomal modifications by homologous recombination, selection of recombinants and antibiotic cassette excision) and protocol 2 (Transduction of phage P1) used in this invention have been fully described in the patent application WO2013/001055.

Protocol 3: Construction of Recombinant Plasmids

Recombinant DNA technology is well described and known by the man skilled in the art.

Briefly, the DNA fragments are PCR amplified using oligonucleotides (the person skilled in the art is able to design) and MG1655 *E. coli* K-12 or other microorganism genomic DNA as matrix (according to the targeted gene to be amplified). The DNA fragments and selected plasmid are digested with compatible restriction enzymes, ligated and then transformed in competent cells. Transformants are analysed and recombinant plasmids of interest are verified by DNA sequencing.

Example 1: Production of 2,4-DHB from Xylose by Overproduction of Enzymes from a New Pathway in MG1655 *E. coli*—Construction of Strains 1 to 11

*Escherichia coli* strain MG1655 was modified to produce 2,4-dihydroxybutanoic acid (2,4-DHB) from D-xylose using the pathway illustrated in FIG. 1. The work seeks to maximize the carbon flux toward the production of 2,4-DHB and so to remove all the enzymes involved in other xylose consuming pathways or involved in conversion of 2,4-DHB-intermediate-compounds, which represents a loss of product.

In addition to the genes naturally expressed by *E. coli* (yjhG gene of sequence SEQ ID NO:64 and yagF gene of sequence SEQ ID NO:65, encoding for xylonate dehydratases, and adhP gene of sequence SEQ ID NO:66 and yqhD gene of sequence SEQ ID NO:67 encoding alcohol dehydrogenases-NAD(P)H-dependant 1,2,4-butanetriol dehydrogenases), the genes coding for the following enzymes; the xylose dehydrogenase and the xylonolactonase of *Caulobacter crescentus* (xdh [CC0821 on CauloCyc, SEQ ID NO:62] and xylC [CC0820 on CauloCyc, SEQ ID NO:63], respectively), the 3-deoxy-D-glycero-pentulosonate decarboxylase of *Pseudomonas putida* (mdlC gene of sequence SEQ ID NO:68), the alcohol dehydrogenase-NAD(P)+ dependant 2,4-dihydroxy-butanal dehydrogenase of *E. coli* or *Clostridium butyricum* (fucO gene from *E. coli* encoding enzyme of sequence SEQ ID NO:41 or dhaT gene from *C. butyricum* encoding enzyme of sequence SEQ ID NO:36, respectively), and the aldehyde dehydrogenase of *E. coli* (puuC gene from *E. coli* encoding enzyme of sequence SEQ ID NO:46 or aldB gene from *E. coli* encoding enzyme of sequence SEQ ID NO:55) were separately expressed with a Ptrc artificial promoter (sequence given in patent WO 2007/0770441) and their own ribosome binding site, using a pCL1920 plasmid (Lerner & Inouye, 1990). In fact, genes xdh, xylC, mdlC, were first cloned on the pCL1920 plasmid giving the plasmid pDHB0001, and then fucO or dhaT and puuC or aldB were sequentially cloned on the plasmid pDHB0001 giving rise to the 4 combinations, with the resulting plasmids pDHB0002 to pDHB0005, as described in table below.

| Couple of genes cloned into the pDHB0001 plasmid overexpressing xdh, xylC, mdlC genes | | | | |
|---|---|---|---|---|
| | fucO, puuC | fucO, aldB | dhaT, puuC | dhaT, aldB |
| Resulting plasmids | pDHB0002 | pDHB0003 | pDHB0004 | pDHB0005 |

Moreover, in order to block the native xylose catabolic pathway, the genes encoding for the D-xylose isomerase (xylA gene of sequence SEQ ID NO:69) and the D-xylulose kinase (xylB gene of sequence SEQ ID NO:70) were deleted from the *E. coli* MG1655 chromosome using the homologous recombination strategy described by Datsenko & Wanner, 2000, and according to Protocol 1. More precisely, to delete xylAB operon, a PCR product carrying the antibiotic resistance gene together with FRT sites surrounded by sequences homologous to up-stream and downstream regions of xylAB operon, was generated with primers of SEQ ID NO:104 and SEQ ID NO:105 and introduced into *E. coli* MG1655 in which the pKD46 vector was previously transformed. The antibiotic resistant transformants were verified with the appropriate oligonucleotides and the retained strain was named strain 1.

To avoid the degradation of the 3-deoxy-D-glycose pentulosonic acid (DGP), the genes encoding the keto acid dehydrogenases (yiaE gene of sequence SEQ ID NO:73; and ycdW gene of sequence SEQ ID NO:74) and the DGP aldolases (yjhH gene of sequence SEQ ID NO:71; and yagE gene of sequence SEQ ID NO:72) were also deleted using the same homologous recombination strategy. More precisely, to delete yjhH gene (SEQ ID NO:71), a PCR product carrying the antibiotic resistance gene together with FRT sites, surrounded by sequences homologous to up-stream and downstream regions of yjhH gene, was generated with primers of SEQ ID NO:106 and SEQ ID NO:107 and introduced into strain 1 in which the pKD46 vector was previously transformed. The antibiotic resistant transformants were verified with the appropriate oligonucleotides and the retained strain was named strain 2. Then, to delete the yagE gene (SEQ ID NO:72), a PCR product carrying the antibiotic resistance gene together with FRT sites, surrounded by sequences homologous to up-stream and downstream regions of yagE gene (SEQ ID NO:108 and SEQ ID NO:109), was generated and introduced into strain 2 in which the pKD46 vector was previously transformed. The antibiotic resistant transformants were verified with the appropriate oligonucleotides and the retained strain was named strain 3. Next, to delete the yiaE gene (SEQ ID NO:73), a PCR product carrying the antibiotic resistance gene together with FRT sites, surrounded by sequences homologous to up-stream and downstream regions of yiaE gene ( ), was generated with primers of SEQ ID NO:110 and SEQ ID NO:111 and introduced into strain 3 in which the pKD46 vector was previously transformed. The antibiotic resistant transformants were verified with the appropriate oligonucleotides and the retained strain was named strain 4. Finally, to delete the ycdW gene (SEQ ID NO:74), a PCR product carrying the antibiotic resistance gene together with FRT sites, surrounded by sequences homologous to up-stream and downstream regions of the ycdW gene, was generated with primers of SEQ ID NO:112 and SEQ ID NO:113 and introduced into strain 4 in which the pKD46 vector was previously transformed. The antibiotic resistant transformants were verified with the appropriate oligonucleotides and the retained strain was named strain 5.

As the yjhH gene belongs together with yjhG (SEQ ID NO:64) and yjhI to the yjhIHG operon, the sequences homologous to up-stream and downstream regions of yjhH must be chosen as to not alter the expression of surrounding genes. It was the same for yagE gene (SED ID NO:72) which belongs to yagEF operon.

Finally, to suppress the catabolite repression, the glucose phophotransferase enzyme IIBC(Glc) encoded by the ptsG gene (SEQ ID NO:75), was deleted by using the homologous recombination strategy described by Datsenko & Wanner, 2000 (according to Protocol 1) as described in patent application EP 14305691.9, in particular in Example 2 of said document using primers of SEQ ID NO:114 and SEQ ID NO:115. The appropriate PCR product was introduced into strain 5 in which the pKD46 vector was previously transformed. The antibiotic resistant transformants were verified with the appropriate oligonucleotides and the retained strain was named strain 6.

Each time a different antibiotic resistance gene was used among kanamycin, chloramphenicol, gentamycin, tetracycline, blasticidin or spectinomycin. Before using strain 6, the antibiotic cassettes were removed from ΔxylAB, ΔyjhH, ΔyagE, ΔyiaE, ΔycdW modifications using the Flp recombinase as described by Datsenko & Wanner, 2000 (according to Protocol 1), giving rise to strain 7.

Then, each plasmid pDHB0002, pDHB0003, pDHB0004 or pDHB0005 described above was introduced into strain 7, giving rise to strains 8 to 11, as described in table below.

| | plasmid introduced into strain 7 | | | |
|---|---|---|---|---|
| | pDHB0002 | pDHB0003 | pDHB0004 | pDHB0005 |
| Resulting strains | Strain 8 | Strain 9 | Strain 10 | Strain 11 |

Example 2: Improving of the 2,4-Dihydroxy-Butanoic Acid Production by Increasing the NADPH Availability of the Producing Strain—Construction of Strains 12 to 20

The 1,2,4-butanetriol dehydrogenases, encoded by adhP and yqhD are in need of reducing power available in the organism, particularly in form of NADPH, so the genes involved in NADPH production were overexpressed.

The membrane bound proton translocating pyridine nucleotide transhydrogenase encoded by the pntAB operon (SEQ ID NO:94) was overproduced by replacing the endogenous promoter and ribosome binding site of pntA gene of *Escherichia coli* MG1655 by the inducible Ptrc promoter (from the plasmid pTRC99A, Amersham Pharmacia) and the define ribosome binding site RBS120 (from RBS Calculator software), as described in patent application EP 14305691.9 in particular in Example 4 of said document (referred herein as SEQ ID NO:116). The appropriate PCR product described in patent application EP 14305691.9 was introduced into strain 7 in which the pKD46 vector was previously transformed. The antibiotic resistant transformants were verified with the appropriate oligonucleotides and the retained strain was named strain 12.

The soluble pyridine nucleotide transhydrogenase encoded by the sthA gene (previously known as udhA, and of sequence SEQ ID NO:95) was deleted by using the homologous recombination strategy described by Datsenko & Wanner, 2000 (according to Protocol 1) and as described in patent application WO 2012/055798, in particular in Example 2 of said application using primers of SEQ ID NO:117 and SEQ ID NO:118). The appropriate PCR product was introduced into strain 12 in which the pKD46 vector was previously transformed. The antibiotic resistant transformants were verified with the appropriate oligonucleotides and the retained strain was named strain 13.

The phosphofructokinase encoded by the pfkA gene (SEQ ID NO:99) was deleted by using the homologous recombination strategy described by Datsenko & Wanner, 2000 (according to Protocol 1), and as described in patent application EP 14305691.9, in particular in Example 5 of said document using primers of SEQ ID NO:119 and SEQ ID NO:120. The appropriate PCR product was introduced into strain 13 in which the pKD46 vector was previously transformed. The antibiotic resistant transformants were verified with the appropriate oligonucleotides and the retained strain was named strain 14.

The NAD-dependent glyceraldehyde phosphate dehydrogenase encoded by the gapA gene from *Escherichia coli* (SEQ ID NO:97) was replaced by the gapN gene from *Streptococcus mutans* (SEQ ID NO:96) coding for a NADP-dependent glyceraldehyde-3-phosphate dehydrogenase (Centeno-Leija et al., 2013) by using the homologous recombination strategy described by Datsenko & Wanner, 2000 (according to Protocol 1). The substitution of the gapA gene by the gapN gene was done by simultaneous substitution of the gapA promoter and ribosome binding site by the thermoinducible PRO1 promoter (SEQ ID NO:121) and its cognate thermolabile repressor C1857 (SEQ ID NO122) as described in Example 1 of patent application EP 2532751, and the define ribosome binding site RBS150 (from RBS Calculator software, SEQ ID NO:123). More precisely, a PCR product carrying the CI857 gene, the PR01 promoter, the RBS150 ribosome binding site, the gapN gene from *Streptococcus mutans* and the antibiotic resistance gene together with FRT sites, surrounded by sequences homologous to the up-stream and down-stream regions of gapA gene on the chromosome, was generated using primers of SEQ ID NO:124 and SEQ ID NO:125 and introduced into strain 14 in which the pKD46 vector was previously transformed. The antibiotic resistant transformants were verified with the appropriate oligonucleotides and the retained strain was named strain 15.

Before using strain 15, the antibiotic cassettes were removed from the pntAB, udhA, pfkA and gapA loci using the Flp recombinase according to Protocol 1, giving rise to strain 16. Finally, each plasmid pDHB0002, pDHB0003, pDHB0004 or pDHB0005 described above was introduced into strain 16, giving rise to strains 17 to 20, as described in table below.

| | plasmid introduced into strain 16 | | | |
|---|---|---|---|---|
| | pDHB0002 | pDHB0003 | pDHB0004 | pDHB0005 |
| Resulting strains | Strain 17 | Strain 18 | Strain 19 | Strain 20 |

Example 3: Overproducing the Enzyme Involved in Sucrose Metabolism in the 2,4-Dihydroxy-Butanoic Acid Producing *E. coli* Recombinant Strain—Construction of Strains 21 to 26

To avoid catabolite repression when the strain is grown on a mix of sucrose and xylose, the natural promoter of the operon xylFGH coding for the importer of xylose (XylF the periplasmic protein, XylG the ATP binding subunit, XylH the membrane subunit) was replaced by an artificial ones by using the homologous recombination strategy described by Datsenko & Wanner, 2000 (according to Protocol 1). More precisely, a PCR product carrying the Ptrc artificial promoter (SEQ ID NO:126) and the kanamycin resistance gene together with FRT sites, surrounded by sequences homologous to xylF gene and to the up-stream region of xylF gene on the chromosome, was generated using primers of SEQ ID NO:127 and SEQ ID NO:128 and introduced into strain 16 in which the pKD46 vector was previously transformed. The kanamycin resistant transformants were verified with the appropriate oligonucleotides and the retained strain was named strain 21.

Before using strain 21, the antibiotic cassette was removed from xylFGH operon using the Flp recombinase according to Protocol 1, giving rise to strain 22.

To allow growth of *E. coli* on sucrose, the genes encoding the fructokinase, scrK, the porine, scrY, the protein IIBC, scrA, the sucrose-6-phosphate invertase, scrB and the repressor, scrR from the plasmid pUR400 of *Salmonella typhimurium* (Schmidt et al., 1982, SEQ ID NO:81) were cloned under their natural promoters on a pBBR1MCS plasmid (Kovach et al., 1995), giving the plasmid pBD00003.

Finally, the plasmid pBD00003, in combination with one of the plasmids pDHB0002, pDHB0003, pDHB0004 or pDHB0005, were introduced into strain 22, giving rise to strain 23 to strain 26, as described in table below.

| | plasmid introduced into strain 22 (with the plasmid pBDO0003) | | | |
|---|---|---|---|---|
| | pDHB0002 | pDHB0003 | pDHB0004 | pDHB0005 |
| Name of strain | Strain 23 | Strain 24 | Strain 25 | Strain 26 |

Example 4: Microbial Production of 2,4-Dihydroxy-Butanoic Acid

Production strains were evaluated in 500 ml baffled Erlenmeyer flasks using modified M9 medium (Anderson, 1946) that was supplemented with 30 g/l MOPS, 20 g/L D-xylose and 10 g/l glucose and adjusted at pH 6.8. Spectinomycin was added at a concentration of 50 mg·L-1 and tetracycline at 5 mg·L-1 when it was necessary in preculture and culture. A preculture was grown at 37° C. in LB medium (Sigma). After 24 hours of growth, it was used to inoculate a 50 mL culture of modified M9 medium to an OD600 of about 0.2, at 30° C. and 200 rpm. When sugars in the culture medium were exhausted, the culture was centrifuged and the broth analysed for 2,4-dihydroxy-butanoic acid by LC-MS/MS.

The 2,4-dihydroxy-butanoic acid titer was expressed as followed:

$$Titer_{DHB} = \frac{2,4\text{-dihydroxy-butanoic-acid (mg)}}{\text{volume }(L)}$$

TABLE 2

2,4-dihydroxy-butanoic acid (DHB) titer for each strain evaluated in Erlenmeyer flasks.

| Strain | DHB Titer |
|---|---|
| MG1655 | – |
| Strains 8 to 11 | + |
| Strain 17 to 20 | ++ |

The sign (−) means a production of 2,4-DHB inferior to 5 mg/L, while the sign (+) corresponds to a production of 2,4-DHB comprised between 5 and 15 mg/L, and the sign (++) corresponds to a production of 2,4-DHB above 15 mg/L.

A production of 2,4-dihydroxy-butanoic acid was observed for all recombinant strains. The production was enhanced by the genetic modifications performed to increase the NADPH pool in the cell.

The strains 23 to 26 (not presented in table 2) were tested on a mix of xylose and sucrose in the same conditions as described above in example 5, and its 2,4-DHB production was similar to strain 8 to 11.

REFERENCES

Altschul S, Gish W, Miller W, Myers E, Lipman D J, J. Mol. Biol, 1990, 215 (3): 403-410
Anderson, Proc. Natl. Acad. Sci. USA., 1946, 32:120-128.
Bocanegra J, Scrutton N, Perham R, Biochemistry, 1993, 32 (11): 2737-2740.
Carrier T & Keasling J, Biotechnol Prog., 1999, 15 (1): 58-64.

Centeno-Leija S, Utrilla J, Flores N, Rodriguez A, Gosset G, Martinez A, Antonie Van Leeuwenhoek., 2013, 104 (6), 913-924.
Datsenko K A & Wanner B L, Proc Natl Acad Sci USA., 2000, 97: 6640-6645.
Davis J J & Olsen G J., Mol. Biol. Evol., 2011, 28(1):211-221.
Deml L, Bojak A, Steck S, Graf M, Wild J, Schirmbeck R, Wolf H, Wagner R., 2011, J. Virol., 75(22): 10991-11001.
Graf M, Bojak A, Deml L, Bieler K, Wolf H, Wagner R., 2000, J. Virol., 74(22): 10/22-10826
Hogema et al., Molecular microbiology, 1997, 24-857-867.
Kim, J. H. et al., Appl. Microbiol. Biotechnol., 2010, 88, 1077-1085.
Kovach M E, Elzer P H, Hill D S, Robertson G T, Farris M A, Roop R M, Peterson K M., Gene, 1995, 166(1):175-6.
Lee S, McCormick M, Lippard S, Cho U, Nature, 2013, 494: 380-384.
Lerner C. G. and Inouye M., Nucleic Acids Research, 1990, 18(15):4631.
Lim S, Jung Y, Shin H, Lee Y, J Biosci Bioeng., 2002, 93 (6):543-549.
Marbaix A, Noel G, Detroux A, Vertommen D, Schaftingen E, Linster C, J Biol Chem., 2011, 286 (48): 41246-41252.
Salis H, Methods Enzymol., 2011, 498:19-42.
Sambrook et al., Molecular cloning: A laboratory manual 4th edition, Cold Spring Harbor Laboratory Press—Cold Spring Harbor, N.Y., USA, 2012.
Schmidt K, Schupfner M, Schmitt R, J. Bacteriol., 1982, 151: 68-76.
Segel I H, Enzyme kinetics, (1993), John Wiley & Sons, pp. 44-54 and 100-112.

The invention claimed is:

1. A genetically modified *Escherichia* for the production of 2,4-dihydroxybutyrate (2,4-DHB) by converting xylose into 1,2,4-butanetriol, wherein said *Escherichia* is further genetically modified for:
   i) an overexpression of at least one gene encoding EC 1.1.1 enzyme which is NAD(P)+dependent, thereby oxidizing 1,2,4-butanetriol into 2,4-dihydroxybutanal;
   ii) an overexpression of at least one gene encoding EC 1.2.1 enzyme which is NAD(P)+dependent, thereby oxidizing 2,4-dihydroxybutanal into 2,4-dihydroxybutyrate; and
   iii) a deletion and/or attenuation of at least one of the following genes:
      a gene encoding a xylose isomerase,
      a gene encoding a xylulose kinase,
      a gene encoding a 3-deoxy-D-glycero-pentulosonate aldolase,
      a gene encoding a keto-acid dehydrogenase, and
      any combination thereof, and
   wherein said *E. coli* produces at least 5 mg/L of 2,4-DHB.

2. The *Escherichia* according to claim 1, wherein the genetic modification for converting xylose into 1,2,4-butanetriol is an overexpression of at least one of the following genes:
   a gene encoding a xylose dehydrogenase,
   a gene encoding a xylonolactonase,
   a gene encoding a xylonate dehydratase,
   a gene encoding a 3-deoxy-D-glycero-pentulosonate decarboxylase,
   a gene encoding a 1,2,4-butanetriol dehydrogenase, and
   any combination thereof.

3. The *Escherichia* according to claim 1, wherein said *Escherichia* is further genetically modified for:
   iv) at least partially inhibiting carbon catabolite repression.

4. The *Escherichia* according to claim 3, wherein the genetic modification iv) is selected from at least one of the following:
   deletion of a gene encoding a glucose permease of the phosphotransferase system,
   deletion of a gene encoding a phosphocarrier Hpr protein,
   expression of a gene and/or operon involved in a sugar importer system wherein said sugar is a carbon source other than xylose,
   expression of a gene encoding a xylose transporter,
   overexpression of a gene encoding a glucose symporter,
   overexpression of a gene encoding a glucose facilitator,
   overexpression of a gene encoding a glucokinase,
   modulation of the expression of a gene involved in cAMP levels,
   modulation of the expression a gene encoding a CRP and/or a CRP-like protein,
   expression of a gene encoding a cAMP-independent CRP protein, and
   any combination thereof.

5. The *Escherichia* according to claim 1, comprising a further genetic modification of at least one gene involved in the production of NADPH as a source of reducing power.

6. The *Escherichia* of claim 5, wherein said modification is selected from the group consisting of:
   overexpression of a gene or operon encoding a membrane-bound transhydrogenase,
   deletion or attenuation of a gene encoding a soluble transhydrogenase,
   overexpression of a gene encoding a NADPH generating glyceraldehyde 3-phosphate dehydrogenase,
   deletion or attenuation of a gene encoding a phosphoglucose isomerase,
   deletion or attenuation of a gene encoding a phosphofructokinase,
   overexpression of a gene encoding a glucose-6-phosphate dehydrogenase,
   overexpression of a mutant gene encoding a lipoamide dehydrogenase capable of generating NADPH,
   overexpression of a gene encoding a bi-functional NAD (P)H-hydrate repair enzyme, and
   any combination thereof.

7. A method for the production of 2,4-dihydroxybutyrate comprising:
   a) culturing a genetically modified *Escherichia* as defined in claim 1 in a culture medium comprising xylose, under fermentation conditions allowing conversion of xylose into 2,4-dihydroxybutyrate, and
   b) recovering the 2,4-dihydroxybutyrate from said culture medium.

8. The method of claim 7, wherein said culture medium comprises a carbon source other than xylose.

9. The method of claim 8, wherein said carbon source other than xylose is a carbohydrate comprising 3, 6 or 12 carbon atoms.

10. The method of claim 9, wherein said carbon source other than xylose is selected from the group consisting of glycerol, glucose, galactose, fructose, lactose, maltose, sucrose, and any combination thereof.

* * * * *